United States Patent
Xie et al.

(10) Patent No.: US 10,287,337 B2
(45) Date of Patent: May 14, 2019

(54) COMPOSITIONS AND METHODS FOR TREATING ACUTE AND CHRONIC PAIN BY LOCAL ANTAGONISM OF CGRP RECEPTORS, OR COMBINATION WITH SODIUM CHANNEL INHIBITION OR WITH ANTI-INFLAMMATORY AGENTS

(71) Applicant: AfaSci, Inc., Redwood City, CA (US)

(72) Inventors: Xinmin Xie, Burlingame, CA (US); Conrado Pascual, Santa Clara, CA (US); Xi Xie, Cambridge, MA (US); James Xie, Brookline, MA (US)

(73) Assignee: AFASCI, Inc., Redwood City, CA (US)

( * ) Notice: Subject to any disclaimer, the term of this patent is extended or adjusted under 35 U.S.C. 154(b) by 4 days.

(21) Appl. No.: 14/727,589

(22) Filed: Jun. 1, 2015

(65) Prior Publication Data
US 2016/0347810 A1    Dec. 1, 2016

(51) Int. Cl.
| | |
|---|---|
| *A61K 38/00* | (2006.01) |
| *A61P 23/00* | (2006.01) |
| *A61K 38/10* | (2006.01) |
| *A61K 38/04* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 14/575* | (2006.01) |
| *A61K 9/00* | (2006.01) |
| *A61K 45/06* | (2006.01) |
| *A61K 38/23* | (2006.01) |
| *C07K 7/08* | (2006.01) |
| *C07K 14/72* | (2006.01) |

(52) U.S. Cl.
CPC ...... *C07K 14/57527* (2013.01); *A61K 9/0021* (2013.01); *A61K 38/10* (2013.01); *A61K 38/23* (2013.01); *A61K 45/06* (2013.01); *C07K 7/08* (2013.01); *C07K 14/723* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 7,384,930 B2 * | 6/2008 | Chaturvedula | ...... | C07D 487/04 514/212.06 |
| 8,168,592 B2 * | 5/2012 | Gegg, Jr. | ............ | A61K 38/225 424/9.1 |

OTHER PUBLICATIONS

Beck-Sickinger, et al., Peptides for the New Millennium. Springer Netherlands, pp. 222-223 (2002).*
Biondi, Current Pain and Headache Reports 10:167-178 (2006).*
NCBI Database, GenBank Accession No. 1005250A, 1 page (1996).*
Prausntiz et al., Nat. Rev. 3:115-124 (2004).*
Richeimer Pain Medical Group, "Understanding Nociceptive and Neuropathic Pain," available online at http://www.helpforpain.com/arch2000dec.htm, (2000).*
Chakravarty et al., Med. Hypotheses 74:225-231 (2010).*
"Neuroma." Merriam-Webster.com. Merriam-Webster, n.d. Web. Jun. 13, 2016.*
Bell, IM, J. Med. Chem. 57:7838-7858 (2014).*
Michot et al., Eur. J. Pain, 10 pages (2014).*
Rubin et al., "Overview of the Peripheral Nervous System," Merck Manuals, available online at http://www.merckmanuals.com/home/brain,-spinal-cord,-and-nerve-disorders/peripheral-nerve-disorders/overview-of-the-peripheral-nervous-system, 8 pages (Dec. 2015).*
Rubin et al., "Overview of the Cranial Nerves," Merck Manuals, available online at http://www.merckmanuals.com/home/brain,-spinal-cord,-and-nerve-disorders/cranial-nerve-disorders/overview-of-the-cranial-nerves, 5 pages (Dec. 2015).*
Washington Nerve Institute, "Post-Craniotomy Pain and Headache," available online at https://drducicplasticsurgery.com/nerve-surgery/post-craniotomy-pain-headache/, 4 pages (2012).*
Biondi, JAOA, Suppl. 2, 105:S16-S22 (2005).*
Washington Nerve Institute, "Chronic Headache, Migraine, Neuralgia," available online at https://drducicplasticsurgery.com/nerve-surgery/chronic-headache-migraine-neuralgia/, 6 pages at p. 5 (2012).*
Kramer et al., "Vestibular Migraine", available online at http://vestibular.org/migraine-associated-vertigo-mav, 10 pages (2012).*
Russo, Annu. Rev. Pharmacol. Toxicol. 55:533-552 (2015).*
Long, MD, "Migraine Changes Everything—Even Back Pain," available online at http://cdi.edu.au/clarity/migraine_changes_everything.php, 3 pages (2013).*
Carmichael, N., Thesis Paper: The Timecourse for Neurogenic Inflammation and the Effect of Modulatory Agents, available online at https://tspace.library.utoronto.ca/bitstream/1807/11107/1/Carmichael_Nicole_200803_PhD_thesis.pdf, pp. 1-251 (2008) (Year: 2008).*
Frantz et al., "Thermal Injury", Compendium: Continuing Education for Veternarians, Vetlearn.com, pp. E1-E6 (2011) (Year: 2011).*
Adrianne D. Bennett et al., "Alleviation of mechanical and thermal allodynia by CGRP 8-37 in a rodent model of chronic central pain," *PAIN* 86, 2000, pp. 163-175, Elsevier Science B.V., Netherlands.

(Continued)

*Primary Examiner* — James H Alstrum-Acevedo
*Assistant Examiner* — Thea D'Ambrosio
(74) *Attorney, Agent, or Firm* — Annette S. Parent

(57) ABSTRACT

The present invention provides compositions, and methods for local administration of certain peptides or combination with certain small molecules that produce analgesia and anti-inflammation in a mammal. Exemplary polypeptides provide peripheral analgesia and anti-inflammation when administered via local topical, subcutaneous, intradermal, or intranasal administration, to provide analgesia and anti-inflammation. Through antagonism of peripheral CGRP receptors alone, or in combination with inhibition of sensory sodium channels or anti-inflammation, the compositions of the invention provide local therapeutic pain relief with minimal undesired systemic side effects in a subject. Also provided are improved peptide delivery techniques including microneedle unit dose administering apparatus and methods. Also provided are hydrogel formulations for sustained local delivery to a subject of one or more of the compositions according to the invention in a therapeutically effective amount, thereby providing local pain relief and/or reducing associated inflammation.

8 Claims, 26 Drawing Sheets

Specification includes a Sequence Listing.

(56) References Cited

OTHER PUBLICATIONS

L-C Yu et al., "The calcironin gene-related peptide antagonist CGPR 8-37 increases the latency to withdrawal responses bilaterally in rats with unilateral experimental mononeuropathy, an effect reversed by naloxone," *Neuroscience*, 1996, pp. 523-531, vol. 71, No. 2, IBRO, Great Britain.

Long-Chuan Yu et al., "The calcironin gene-related peptide antagonist CGPR 8-37 increases the latency to withdrawal responses bilaterally in rats," *Brain Research*, Brain Research 653, 1994, pp. 223-230, Elsevier Science B.V., Netherlands.

Silvia Benemei et al., "CGRP receptors in the control of pain and inflammation," *Current Opinion in Pharmacology*, 2009, pp. 9-14, Elsevier Ltd., Netherlands.

Henri Doods et al., "CGRP antagonists: unravelling the role of CGRP in migraine," *Trends in Pharmacological Sciences*, 2007, pp. 580-587, vol. 28 No. 11, Elsevier Ltd., Netherlands.

Stewart J. Tepper et al., "Clinical and Preclinical Rationale for CGRP-Receptor Antagonists in the Treatment of Migraine," *Headache Currents*, 2008, pp. 1259-1268, American Headache Society, Cleveland, USA.

Jennifer T. Malon et al., "Involvement of calcitonin gene-related peptide and CCL2 production in CD40-mediated behavioral hypersensitivity in a model of neuropathic pain," *Neuron Glia Biol.*, May 2011, pp. 117-128, Cambridge University Press, Biddeford USA.

Qing Lin et al., "Roles of TRPV and neuropeptidergic receptors in dorsal root reflex-mediated neurogenic inflammation induced by intradermal injection of capsaicin," *Molecular Pain*, Oct. 25, 2007, BioMed Central.

\* cited by examiner

SEQUENCE LISTING

```
<160> NUMBER OF SEQ ID NOS: 44

<210> SEQ ID NO 1
<211> LENGTH: 37
<212> TYPE: PRT
<213> ORGANISM: Artificial Sequence
<220> FEATURE:
<223> OTHER INFORMATION: wild type human calcitonin gene-related peptide
      (CGRP)
<220> FEATURE:
<221> NAME/KEY: MOD_RES
<222> LOCATION: (37)..(37)
<223> OTHER INFORMATION: AMIDATION

<400> SEQUENCE: 1

Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35

<210> SEQ ID NO 2
<211> LENGTH: 9
<212> TYPE: PRT
<213> ORGANISM: Artificial Sequence
<220> FEATURE:
<223> OTHER INFORMATION: isolated polypeptide
<220> FEATURE:
<221> NAME/KEY: MOD_RES
<222> LOCATION: (9)..(9)
<223> OTHER INFORMATION: R3

<400> SEQUENCE: 2

Pro Thr Asn Val Gly Pro Phe Ala Phe
1               5

<210> SEQ ID NO 3
<211> LENGTH: 11
<212> TYPE: PRT
<213> ORGANISM: Artificial Sequence
<220> FEATURE:
```

```
<223> OTHER INFORMATION: peptide
<220> FEATURE:
<221> NAME/KEY: MOD_RES
<222> LOCATION: (1)..(1)
<223> OTHER INFORMATION: R1 and R2
<220> FEATURE:
<221> NAME/KEY: MOD_RES
<222> LOCATION: (11)..(11)
<223> OTHER INFORMATION: R3

<400> SEQUENCE: 3

Phe Val Pro Thr Asn Val Gly Pro Phe Ala Phe
1               5                   10

<210> SEQ ID NO 4
<211> LENGTH: 11
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: R1 and R2
<220> FEATURE:
<221> NAME/KEY: MOD_RES
<222> LOCATION: (11)..(11)
<223> OTHER INFORMATION: R3

<400> SEQUENCE: 4

Phe Ile Pro Thr Asn Val Gly Pro Phe Ala Phe
1               5                   10

<210> SEQ ID NO 5
<211> LENGTH: 12
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: R1 and R2
<220> FEATURE:
<221> NAME/KEY: MOD_RES
<222> LOCATION: (12)..(12)
<223> OTHER INFORMATION: R3

<400> SEQUENCE: 5

Asn Phe Val Pro Thr Asn Val Gly Pro Phe Ala Phe
1               5                   10

<210> SEQ ID NO 6
<211> LENGTH: 11
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: R1 and R2
<220> FEATURE:
<221> NAME/KEY: MOD_RES
<222> LOCATION: (11)..(11)
<223> OTHER INFORMATION: R3

<400> SEQUENCE: 6

Trp Val Pro Thr Asn Val Gly Pro Phe Ala Phe
1               5                   10
```

```
<210> SEQ ID NO 7
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: R1 and R2
<220> FEATURE:
<221> NAME/KEY: MOD_RES
<222> LOCATION: (13)..(13)
<223> OTHER INFORMATION: R3

<400> SEQUENCE: 7

Asp Asn Phe Val Pro Thr Asn Val Gly Pro Phe Ala Phe
1               5                   10

<210> SEQ ID NO 8
<211> LENGTH: 12
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: R1 and R2
<220> FEATURE:
<221> NAME/KEY: MOD_RES
<222> LOCATION: (12)..(12)
<223> OTHER INFORMATION: R3

<400> SEQUENCE: 8

Asn Phe Ile Pro Thr Asn Val Gly Pro Phe Ala Phe
1               5                   10

<210> SEQ ID NO 9
<211> LENGTH: 12
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: R1 and R2
<220> FEATURE:
<221> NAME/KEY: MOD_RES
<222> LOCATION: (12)..(12)
<223> OTHER INFORMATION: R3

<400> SEQUENCE: 9

Asn Phe Leu Pro Thr Asn Val Gly Pro Phe Ala Phe
1               5                   10

<210> SEQ ID NO 10
<211> LENGTH: 12
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: R1 and R2
<220> FEATURE:
<221> NAME/KEY: MOD_RES
<222> LOCATION: (12)..(12)
<223> OTHER INFORMATION: R3

<400> SEQUENCE: 10
```

```
Asn Leu Val Pro Thr Asn Val Gly Pro Phe Ala Phe
1               5                   10
```

<210> SEQ ID NO 11
<211> LENGTH: 12
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: R1 and R2
<220> FEATURE:
<221> NAME/KEY: MOD_RES
<222> LOCATION: (12)..(12)
<223> OTHER INFORMATION: R3

<400> SEQUENCE: 11

```
Asn Phe Phe Pro Thr Asn Val Gly Pro Phe Ala Phe
1               5                   10
```

<210> SEQ ID NO 12
<211> LENGTH: 12
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: R1 and R2
<220> FEATURE:
<221> NAME/KEY: MOD_RES
<222> LOCATION: (12)..(12)
<223> OTHER INFORMATION: R3

<400> SEQUENCE: 12

```
Asn Phe Ala Pro Thr Asn Val Gly Pro Phe Ala Phe
1               5                   10
```

<210> SEQ ID NO 13
<211> LENGTH: 11
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (11)..(11)
<223> OTHER INFORMATION: R3

<400> SEQUENCE: 13

```
Phe Val Pro Thr Asn Val Gly Pro Phe Ala Phe
1               5                   10
```

<210> SEQ ID NO 14
<211> LENGTH: 11
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (11)..(11)
<223> OTHER INFORMATION: R3

<400> SEQUENCE: 14

```
Phe Ile Pro Thr Asn Val Gly Pro Phe Ala Phe
1               5                   10
```

```
<210> SEQ ID NO 15
<211> LENGTH: 12
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (12)..(12)
<223> OTHER INFORMATION: R3

<400> SEQUENCE: 15

Asn Phe Val Pro Thr Asn Val Gly Pro Phe Ala Phe
1               5                   10

<210> SEQ ID NO 16
<211> LENGTH: 11
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (11)..(11)
<223> OTHER INFORMATION: R3

<400> SEQUENCE: 16

Trp Val Pro Thr Asn Val Gly Pro Phe Ala Phe
1               5                   10

<210> SEQ ID NO 17
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (13)..(13)
<223> OTHER INFORMATION: R3

<400> SEQUENCE: 17

Asp Asn Phe Val Pro Thr Asn Val Gly Pro Phe Ala Phe
1               5                   10

<210> SEQ ID NO 18
<211> LENGTH: 12
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (12)..(12)
<223> OTHER INFORMATION: R3

<400> SEQUENCE: 18

Asn Phe Ile Pro Thr Asn Val Gly Pro Phe Ala Phe
1               5                   10

<210> SEQ ID NO 19
<211> LENGTH: 12
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (12)..(12)
```

<223> OTHER INFORMATION: R3

<400> SEQUENCE: 19

Asn Phe Leu Pro Thr Asn Val Gly Pro Phe Ala Phe
1               5                   10

<210> SEQ ID NO 20
<211> LENGTH: 12
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (12)..(12)
<223> OTHER INFORMATION: R3

<400> SEQUENCE: 20

Asn Leu Val Pro Thr Asn Val Gly Pro Phe Ala Phe
1               5                   10

<210> SEQ ID NO 21
<211> LENGTH: 12
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (12)..(12)
<223> OTHER INFORMATION: R3

<400> SEQUENCE: 21

Asn Phe Phe Pro Thr Asn Val Gly Pro Phe Ala Phe
1               5                   10

<210> SEQ ID NO 22
<211> LENGTH: 12
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (12)..(12)
<223> OTHER INFORMATION: R3

<400> SEQUENCE: 22

Asn Phe Ala Pro Thr Asn Val Gly Pro Phe Ala Phe
1               5                   10

<210> SEQ ID NO 23
<211> LENGTH: 11
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: R1 and R2
<220> FEATURE:
<221> NAME/KEY: MOD_RES
<222> LOCATION: (11)..(11)
<223> OTHER INFORMATION: AMIDATION

<400> SEQUENCE: 23

Phe Val Pro Thr Asn Val Gly Pro Phe Ala Phe
1               5                   10

```
<210> SEQ ID NO 24
<211> LENGTH: 11
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: R1 and R2
<220> FEATURE:
<221> NAME/KEY: MOD_RES
<222> LOCATION: (11)..(11)
<223> OTHER INFORMATION: AMIDATION

<400> SEQUENCE: 24

Phe Ile Pro Thr Asn Val Gly Pro Phe Ala Phe
1               5                   10

<210> SEQ ID NO 25
<211> LENGTH: 12
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: R1 and R2
<220> FEATURE:
<221> NAME/KEY: MOD_RES
<222> LOCATION: (12)..(12)
<223> OTHER INFORMATION: AMIDATION

<400> SEQUENCE: 25

Asn Phe Val Pro Thr Asn Val Gly Pro Phe Ala Phe
1               5                   10

<210> SEQ ID NO 26
<211> LENGTH: 11
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: R1 and R2
<220> FEATURE:
<221> NAME/KEY: MOD_RES
<222> LOCATION: (11)..(11)
<223> OTHER INFORMATION: AMIDATION

<400> SEQUENCE: 26

Trp Val Pro Thr Asn Val Gly Pro Phe Ala Phe
1               5                   10

<210> SEQ ID NO 27
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: R1 and R2
<220> FEATURE:
<221> NAME/KEY: MOD_RES
<222> LOCATION: (13)..(13)
<223> OTHER INFORMATION: AMIDATION
```

```
<400> SEQUENCE: 27

Asp Asn Phe Val Pro Thr Asn Val Gly Pro Phe Ala Phe
1               5                   10

<210> SEQ ID NO 28
<211> LENGTH: 12
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: R1 and R2
<220> FEATURE:
<221> NAME/KEY: MOD_RES
<222> LOCATION: (12)..(12)
<223> OTHER INFORMATION: AMIDATION

<400> SEQUENCE: 28

Asn Phe Ile Pro Thr Asn Val Gly Pro Phe Ala Phe
1               5                   10

<210> SEQ ID NO 29
<211> LENGTH: 12
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: R1 and R2
<220> FEATURE:
<221> NAME/KEY: MOD_RES
<222> LOCATION: (12)..(12)
<223> OTHER INFORMATION: AMIDATION

<400> SEQUENCE: 29

Asn Phe Leu Pro Thr Asn Val Gly Pro Phe Ala Phe
1               5                   10

<210> SEQ ID NO 30
<211> LENGTH: 12
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: R1 and R2
<220> FEATURE:
<221> NAME/KEY: MOD_RES
<222> LOCATION: (12)..(12)
<223> OTHER INFORMATION: AMIDATION

<400> SEQUENCE: 30

Asn Leu Val Pro Thr Asn Val Gly Pro Phe Ala Phe
1               5                   10

<210> SEQ ID NO 31
<211> LENGTH: 12
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: R1 and R2
```

```
<220> FEATURE:
<221> NAME/KEY: MOD_RES
<222> LOCATION: (12)..(12)
<223> OTHER INFORMATION: AMIDATION

<400> SEQUENCE: 31

Asn Phe Phe Pro Thr Asn Val Gly Pro Phe Ala Phe
1               5                   10

<210> SEQ ID NO 32
<211> LENGTH: 12
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: R1 and R2
<220> FEATURE:
<221> NAME/KEY: MOD_RES
<222> LOCATION: (12)..(12)
<223> OTHER INFORMATION: AMIDATION

<400> SEQUENCE: 32

Asn Phe Ala Pro Thr Asn Val Gly Pro Phe Ala Phe
1               5                   10

<210> SEQ ID NO 33
<211> LENGTH: 11
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (11)..(11)
<223> OTHER INFORMATION: AMIDATION

<400> SEQUENCE: 33

Phe Val Pro Thr Asn Val Gly Pro Phe Ala Phe
1               5                   10

<210> SEQ ID NO 34
<211> LENGTH: 11
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (11)..(11)
<223> OTHER INFORMATION: AMIDATION

<400> SEQUENCE: 34

Phe Ile Pro Thr Asn Val Gly Pro Phe Ala Phe
1               5                   10

<210> SEQ ID NO 35
<211> LENGTH: 12
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (12)..(12)
<223> OTHER INFORMATION: AMIDATION

<400> SEQUENCE: 35
```

```
Asn Phe Val Pro Thr Asn Val Gly Pro Phe Ala Phe
1               5                   10
```

<210> SEQ ID NO 36
<211> LENGTH: 11
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (11)..(11)
<223> OTHER INFORMATION: AMIDATION

<400> SEQUENCE: 36

```
Trp Val Pro Thr Asn Val Gly Pro Phe Ala Phe
1               5                   10
```

<210> SEQ ID NO 37
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (13)..(13)
<223> OTHER INFORMATION: AMIDATION

<400> SEQUENCE: 37

```
Asp Asn Phe Val Pro Thr Asn Val Gly Pro Phe Ala Phe
1               5                   10
```

<210> SEQ ID NO 38
<211> LENGTH: 12
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (12)..(12)
<223> OTHER INFORMATION: AMIDATION

<400> SEQUENCE: 38

```
Asn Phe Ile Pro Thr Asn Val Gly Pro Phe Ala Phe
1               5                   10
```

<210> SEQ ID NO 39
<211> LENGTH: 12
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (12)..(12)
<223> OTHER INFORMATION: AMIDATION

<400> SEQUENCE: 39

```
Asn Phe Leu Pro Thr Asn Val Gly Pro Phe Ala Phe
1               5                   10
```

<210> SEQ ID NO 40
<211> LENGTH: 12
<212> TYPE: PRT
<213> ORGANISM: Artificial Sequence
<220> FEATURE:
<223> OTHER INFORMATION: peptide
<220> FEATURE:

```
<221> NAME/KEY: MOD_RES
<222> LOCATION: (12)..(12)
<223> OTHER INFORMATION: AMIDATION

<400> SEQUENCE: 40

Asn Leu Val Pro Thr Asn Val Gly Pro Phe Ala Phe
1               5                   10

<210> SEQ ID NO 41
<211> LENGTH: 12
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (12)..(12)
<223> OTHER INFORMATION: AMIDATION

<400> SEQUENCE: 41

Asn Phe Phe Pro Thr Asn Val Gly Pro Phe Ala Phe
1               5                   10

<210> SEQ ID NO 42
<211> LENGTH: 12
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (12)..(12)
<223> OTHER INFORMATION: AMIDATION

<400> SEQUENCE: 42

Asn Phe Ala Pro Thr Asn Val Gly Pro Phe Ala Phe
1               5                   10

<210> SEQ ID NO 43
<211> LENGTH: 30
<212> TYPE: PRT
<213> ORGANISM: Artificial Sequence
<220> FEATURE:
<223> OTHER INFORMATION: AFA-peptide
<220> FEATURE:
<221> NAME/KEY: MOD_RES
<222> LOCATION: (30)..(30)
<223> OTHER INFORMATION: AMIDATION

<400> SEQUENCE: 43

Val Thr His Arg Leu Ala Gly Leu Leu Ser Arg Ser Gly Gly Met Val
1               5                   10                  15

Lys Ser Asn Phe Val Pro Thr Asn Val Gly Ser Lys Ala Phe
            20                  25                  30

<210> SEQ ID NO 44
<211> LENGTH: 11
<212> TYPE: PRT
<213> ORGANISM: Artificial Sequence
<220> FEATURE:
<223> OTHER INFORMATION: AFA-peptide
<220> FEATURE:
<221> NAME/KEY: MOD_RES
<222> LOCATION: (11)..(11)
<223> OTHER INFORMATION: AMIDATION
```

```
<400> SEQUENCE: 44

Tyr Val Pro Thr Ala Val Gly Pro Phe Ala Phe
1               5                   10
```

COMPOSITIONS AND METHODS FOR TREATING ACUTE AND CHRONIC PAIN BY LOCAL ANTAGONISM OF CGRP RECEPTORS, OR COMBINATION WITH SODIUM CHANNEL INHIBITION OR WITH ANTI-INFLAMMATORY AGENTS

STATEMENT OF GOVERNMENT RIGHTS

This invention was made with Government support under Grant 5 R44DA026363-03 awarded by the National Institute on Drug Abuse. The Government has certain rights in this invention.

FIELD OF THE INVENTION

The present invention relates to compositions and methods for treating acute and chronic or persistent pain via a local application of a CGRP receptor antagonist peptide or a combination of a CGRP antagonist and a sodium channel blocker or an anti-inflammatory drug to a patient in need of such treatments.

BACKGROUND OF THE INVENTION

Acute or chronic pain is one of the most widespread and frequent human complaints, as well as one of the most difficult syndromes to treat successfully with drugs or surgery. Some types of acute or chronic pain are particularly related to neuropathic and/or neurogenic inflammation. Such neurogenic inflammation can be triggered by the activation of unmyelinated sensory neurons through noxious stimuli and the subsequent release of neuropeptides such as calcitonin gene-related peptide (CGRP, U.S. Pat. No. 4,549,986) and substance P (SP) from the peripheral nerve endings of these nociceptive neurons (Amara, et al., 1982; Nassini, et al., 2014). Additionally, inflammation activates transient receptor potential vanilloid 1 (TRPV1) on sensory nerves to further liberate CGRP and SP in peripheral tissues and the dorsal horn to cause neurogenic inflammation and pain through activation of their receptors (Trevisan, et al., 2014).

Isoform α-CGRP, a 37 amino acid peptide, is generated from a specific splicing of calcitonin and synthesized in the somata of nociceptive neurons in the dorsal root ganglion (DRG). α-CGRP and β-CGRP can be transported to the peripheral and central nerve endings where it can be released upon intensive activation of those afferents (Boulanger, et al., 1995). CGRP has been found in approximately 50% of C fibers and 35% of Aδ-fibers. When released from nerve terminals, α-CGRP or β-CGRP binds to a heteromeric receptor of calcitonin receptor-like receptor (CALCRL) and receptor activity-modifying protein 1 (RAMP1), and increases nociceptive sensitivity in response to non-noxious mechanical and thermal stimuli under normal conditions.

Under pathological conditions, excessively released CGRP prolongs and enhances vasodilatation and plasma extravasation initiated by inflammatory mediators such as histamine, prostaglandins (e.g., PGE2), and cytokines. Thus, excessive CGRP produces thermal hyperalgesia and mechanical allodynia, a condition in which pain is induced by otherwise non-noxious stimuli, and plays a critical role in development of neurogenic inflammatory and chronic pain. For example, CGRP released from the C-fibers projecting from the trigeminal ganglion to the cerebral meninges (outer brain liner) has been suggested to play a crucial role in the pathophysiology of headaches, particularly migraines. TRPV1 agonist capsaicin evokes a concentration-dependent increase in CGRP release in rat trigeminal ganglia slices. These observations suggest that CGRP release with associated neurogenic dural vasodilation may be important in the generation of migraine pain. Furthermore, overexpression of CGRP has been found in migraine and temporomandibular joint (TMJ) disorder.

In preclinical research, using a gene knockout approach, mice lacking CGRP display an attenuated response to chemical-induced pain and inflammation. Using antisense sequence to knock down CGRP specifically in sensory neurons produced a reduction of CGRP levels, and also a decrease in the behavioral hyperalgesia that resulted from capsaicin treatment (Tzabazis et al., 2007). The N-terminal amino acids 1-7 are required for receptor activation and signal transduction, whereas the remainder (amino acids 8-37) of CGRP is necessary for receptor binding. Thus, a polypeptide that contains only amino acids 8-37 of CGRP (CGRP8-37) can act as a CGRP receptor antagonist. Intravenous (i.v.) of a variety of anti-CGRP antibodies and i.v. or intrathecal (i.t.) administration of human CGRP 8-37, a 31 amino acid fragment of CGRP that lacks seven N-terminal amino acids has been found to significantly attenuate chemical (e.g., capsaicin or acetic acid as well as CGRP)-induced hypersensitivity via blockade of CGRP receptors (Plourde, et al., 1997, and U.S. Pat. No. 6,268,474; WO 2007048026 A2; WO 2007048026 A2; WO 2009/109911; US 20110054150 A1).

In clinical studies, migraine therapeutics sumatriptan and donitriptan have been demonstrated to inhibit CGRP release as well as to prevent or attenuate associated neurogenic inflammation. CGRP-mediated neurogenic dural vasodilation is blocked by dihydroergotamine, triptans, and opioids, all of which have demonstrated clinical efficacy against migraines. The systemic administration of CGRP receptor antagonists CGRP 8-37, BIBN4096 and MK-0974 were under investigation in clinical trials, and initial results indicated that BIBN4096, MK-0974, MK-3207 and BI 44370 alleviated acute migraine headache (Troconiz, et al., 2006; Farinelli, et al., 2009; Nieber, 2009; Edvinsson and Warfvinge, 2013; Hostetler, et al., 2013).

Both preclinical data and clinical evidence obtained using a systemic approach of antagonism of CGRP suggest the site of action is via a central mechanism (Troconiz, et al., 2006; Edvinsson and Warfvinge, 2013; Hostetler, et al., 2013). Systemic antagonism of CGRP often produced undesirable side effects leading to suspension of clinical trials of small molecule CGRP antagonists (Benemei, et al., 2009; Edvinsson and Warfvinge, 2013).

Nerve or tissue injury, trauma or inflammation triggers release of neuropeptides including CGRP from afferent nerve endings, and in turn CGRP enhances nociceptive neuronal activity. Therefore, local injection (e.g., cutaneous injection) of voltage-gated sodium (Na) channel blockers such as lidocaine or bupivacaine have long been used to inhibit local pain sensitivity, such as that following surgery. However their action usually lasts for only a few hours and mainly relieves acute nociceptive pain. The naturally occurring sodium channel blocker saxitoxin in animals such as fish and crabs has been shown to be much more potent in blocking sodium currents in rat DRG neurons than lidocaine. However, because of undesired systemic side effects, saxitoxin cannot be administered systemically. Local administration of saxitoxin has not been trialed in clinic. In clinical trials, scalp injections of botulotoxin A (Botox) have been shown to be effective as a local treatment for migraine, presumably by blocking release of pronociception chemicals including CGRP from nociceptive afferents. Although this procedure may provide peripheral therapy for migraine, Botox also paralyzes skeletal muscles, which may lead to unwanted side-effects (except for its currently approved local cosmetic use).

The pathophysiology of excessive CGRP has now been recognized as a key contributing factor in acute or chronic pain with known or uncertain etiology in humans, such as postoperative pain (surgical or incision pain), neuromas, migraines, radiation pain, diabetic neuropathic pain, primary erythromelalgia and secondary erythromelalgia (resulting from a variety of disorders or toxications), and complex regional pain syndrome, etc. (Herbert and Holzer, 2002).

Current systemic pharmacological therapeutics for migraine and neuropathic pain include the triptans (serotonin 5-HT1B/1D agonists, e.g. sumatriptan), non-steroidal anti-inflammatory drugs (NSAIDs, e.g. tramadol), anti-convulsants (e.g. carbamazepine and lamotrigine), antidepressants (e.g. amitryptiline and duloxetine), narcotics (e.g. oxycodone) and anti-neuropathic pain drugs (gabapentin and pregabaline). However, none of these treatment options provides acceptable systemic pain relief for more than 50% of the treated patients. In addition, all of these drugs are known to have undesirable systemic side effects (Uhl, et al., 2014). Therefore, there is a need for compounds are more effective and safer analgesics and/or anti-inflammatories. In addition, there is a need for improved means of delivering such drugs to the body to reduce systemic side effects and avoid toxicity. The present invention provides such compounds.

BRIEF SUMMARY OF THE INVENTION

The present invention provides safe and effective analgesics and anti-inflammatory agents. Also provided are pharmaceutical formulations incorporating these compounds, and methods of using the compounds and formulations to treat pain, injury and other conditions in a subject in need of such treatment. There is also provided a delivery device for safe and effective delivery of the compounds or formulations of the invention, which is charged with a composition or formulation of the invention.

In one embodiment, the invention provides compositions mitigating local and, at least to an extent, systemic acute or chronic pain including, but not limited to, acute or chronic pain with known or uncertain etiology in humans, such as postoperative pain (surgical or incision pain), neuromas, migraines, tension headache, burn pain, radiation pain, diabetic neuropathic pain, primary erythromelalgia and secondary erythromelalgia, and complex regional pain syndrome, etc. (Herbert and Holzer, 2002).

In an exemplary embodiment, the invention provides a pharmaceutical formulation comprising a therapeutically effective amount (e.g., a pain relieving and/or anti-inflammatory effective amount) of an active AFA-peptide or CGRP 8-37, alone, or in combination with another pain relieving and/or anti-inflammatory agent (e.g., sodium channel blockers, e.g., lidocaine, bupivacaine or saxitoxin). In various embodiments, the formulation provides peripheral antagonism of CGRP receptors and blockade of sodium channels yielding local therapeutic pain relief without significant undesirable local or systemic side effects in a mammal. An exemplary formulation according to the invention further comprises an anti-inflammatory composition, a NSAID composition, or both.

Also provided are improved techniques and methods for local delivery to a subject of a therapeutically effective amount of one or more of the pain-relieving compositions as described herein to provide local pain relief and, in various embodiments, to reduce associated neurogenic inflammation in a mammal. In various embodiments, these methods also yield reduced undesirable systemic side effects.

Another object of the invention is a method for treating local neurogenic pain in the form of burn pain, radiation-induced pain, postoperative pain, a neuroma, a migraine or tension headache in a subject in need of such treatment. In an exemplary embodiment, the treatment includes local topical application or injection of a pain relieving composition according to the invention at or near a site of pain. In various embodiments, the invention includes administering to a subject a topical application, or intradermal injection of a composition according to the invention at a specific area, e.g., at a so called 'trigger point' or acupuncture point. Exemplary points include the nape of the neck just above the brain stem or temporalis.

In an exemplary embodiment, the invention provides apparatus and compositions for time release delivery of a composition of the invention using a hydrogel of a composition of the invention for local relief of peripheral pain or the relief of a migraine or tension headache.

In various embodiments, the invention comprises an apparatus for timed, sustained pain relief wherein the apparatus comprises a plurality of intradermal injection microneedles connected to at least one time release reservoir of a therapeutic composition according to the present invention. In an exemplary embodiment, all or a portion of each of the microneedles is bio-absorbable and/or bio-dissolvable (U.S. Pat. No. 20040199103 A1), though metal microneedles can also be used in the present invention, e.g., with the anti-CGRP peptides or combination with other said reagents (U.S. Pat. No. 6,908,453 B2).

In one embodiment, the invention provides a unit dose sustained release patch apparatus including a plurality of intradermal injection microneedles connected to at least one time release reservoir of a therapeutic composition according to the present invention. An exemplary apparatus is one adapted to treating pain located at one or more of elbow, shoulder, neck, hip, back, or sciatica by delivering a sustained pain relieving dose of the composition intradermally by injection at a site local or proximal to the pain origin.

Another object of the present invention is to provide a unit dose of a pain relieving composition according to the invention through intranasal administration in suitable carrier vehicle to treat a migraine, tension headache, trigeminal neuralgia, tooth ache or root canal pain in patients in need at or near a site of pain.

Other objects, aspects and advantages of the present invention will become apparent from the following detailed description, taken in conjunction with the accompanying drawings, illustrated by way of example of the principles of the invention.

BRIEF DESCRIPTION OF THE DRAWINGS

FIG. 3A. A multi-line graph of the rat thermal pain assessment showing: (i) baseline thermal pain threshold measurements taken pre-SNI operation in, (ii) the pre-treatment thermal pain threshold measurements are taken three weeks post-SNI operation and (iii) treated thermal threshold pain measurements are taken between 0.5-6 hours after local intradermal injection of CGRP 8-37 (0.1, 10, and 30 µM, 50 µL), lidocaine (Sigma, 1.5%, 50 µL) or vehicle (50 µL) into SNI ipsilateral hindpaw (n=8 for each treatment). FIG. 3B. A multi-line graph of the rat mechanical pain assessment from the same cohort of SNI rats showing: (i) baseline mechanical pain threshold measurements taken pre-SNI operation in, (ii) mechanical threshold pain measurements are taken five weeks post-SNI operation and (iii) treated thermal pain threshold measurements are taken between 0.5-6 hours after local intradermal injection of CGRP 8-37, lidocaine or vehicle into SNI ipsilateral paws.

FIG. 4A. A multi-line graph of the rat thermal pain assessment showing: (i) baseline thermal pain threshold measurements taken pre-SNI operation in, (ii) the pre-treatment thermal pain threshold measurement are taken three weeks post-SNI operation and (iii) treated thermal threshold pain measurements are taken between 0.5-6 hours after local intradermal injection of AFA-peptide-3 into SNI ipsilateral paw (0.3, 1, and 10 µM, 50 µL, n=8 for each treatment). FIG. 4B. A multi-line graph of the rat mechanical pain threshold assessment from the same cohort of SNI rats showing: (i) baseline mechanical pain threshold measurements taken pre-SNI operation in, (ii) mechanical pain threshold measurements are taken three weeks post-SNI operation and (iii) treated thermal threshold pain measurements are taken between 0.5-6 hours after local intradermal injection of AFA-peptide-3 into SNI ipsilateral paws.

FIG. 5A. A multi-line graph of the rat thermal pain threshold assessment showing: (i) baseline thermal pain threshold measurements taken pre-SNI operation in, (ii) the pre-treatment thermal threshold pain measurements are taken three and a half weeks post-SNI operation and (iii) treated thermal pain threshold measurements are taken 2 hours after local intradermal injection of AFA-peptide-3 into SNI ipsilateral paws daily (1 µM, 50 µL) and repeated for consecutive 10 days. AFA-peptide-3 produced consistent analgesia compared to the vehicle and did not induce tolerance. FIG. 5B. A multi-line graph of the rat mechanical pain threshold assessment from the same cohort of SNI rats showing: (i) baseline mechanical pain threshold measurements taken pre-SNI operation in, (ii) mechanical pain threshold measurements are taken three and a half weeks post-SNI operation and (iii) treated thermal pain threshold measurements are taken 2 hours after local intradermal injection of AFA-peptide-3 into SNI ipsilateral paws daily (1 µM, 50 µL) and repeated for consecutive 10 days. AFA-peptide-3 produced consistent analgesia compared to the vehicle without induction of tolerance.

FIG. 6A. A bar graph of rat thermal pain assessment data showing: (i) baseline thermal pain threshold measurements taken pre-SNI operation, (ii) the pre-treatment thermal pain threshold measurements are taken two weeks after SNI operation and (iii) treated thermal pain threshold measurements are taken hourly from three groups during the initial one to seven hours post dosing and then at 24 hours after intradermal administration of (1) a therapeutically effective amount of CGRP 8-37, (2) a negative starch control, and (3) a positive therapeutic control (gabapentin, 100 mg/kg, i.p.). All treatments were made two weeks following the SNI operation. FIG. 6B. A bar graph of rat mechanical pain threshold assessment data from the same cohort of animals as A showing: (i) baseline mechanical pain threshold measurements pre-SNI operation, (ii) pre-treatment mechanical pain threshold measurements taken two weeks after the SNI administration and (iii) treated mechanical pain threshold measurements taken hourly from three groups during the initial—one to seven hours post dosing and then at 24 hours after intradermal administration of (1) a therapeutic effective amount of CGRP 8-37, (2) a negative starch control, and (3) a positive therapeutic control (gabapentin, i.p.). All treatments were made two weeks following the SNI operation.

FIG. 8A. A sketch illustrates the tibial neuroma transposition surgery on the left side of the rat. FIG. 8B. Local intradermal application of AFA-peptide 3 (0.3 and 1 µM) around the neuroma. The neuroma tenderness is measured using 50% threshold of mechanical allodynia response (using von Frey hair method) was collected at baseline (day 0, D0 pre-operation), and post-operation (PO) D7, D14, and on D21, at 1, 2, 3 and 4 hours after the peptide injection, and on D22.

FIG. 9A. A bar graph of rat thermal pain assessment data showing: (i) baseline thermal threshold pain measurements pre-STZ injection (ip), (ii) pre-treatment thermal threshold pain measurements taken two weeks after STZ administration and (iii) treated thermal pain threshold measurements taken one hour after intradermal administration of a vehicle control or a therapeutic amount of CGRP 8-37 dosed two weeks after the STZ injection. FIG. 9B. A bar graph of rat mechanical pain threshold assessment data from the same cohort of animals as A showing: (i) baseline mechanical pain threshold measurements pre-STZ injection, (ii) pre-treatment mechanical pain threshold measurements taken two weeks after STZ administration (ip), and (iii) mechanical pain threshold measurements taken one hour after intradermal administration of a vehicle control or a therapeutic amount of CGRP 8-37 dosed two weeks after STZ injection.

FIG. 11A. AFA-peptide-3 and CGRP 8-37 produce little effects on a-delta fiber mediated thermal pain threshold in a UVB radiation-induced pain in rats. FIG. 11B. AFA-peptide-3 and CGRP 8-37 increase C-fiber mediated chemical pain threshold in the same UVB radiation-induced neurogenic inflammatory pain in rats.

FIG. 12A. A bar graph of A-delta fiber-mediated pain assessments showing: I.N. administered AFA-peptide 3 significantly prolongs paw withdrawal latencies induced by A-delta fiber-mediated pain, while CGRP 8-37 treatment had insignificant analgesic effects compared to vehicle. FIG. 12B. A bar graph of C-fiber-mediated pain assessment data showing: I.N. administered AFA-peptide 3 or CGRP 8-37 significantly prolonged paw withdrawal latencies induced by C-fiber-mediated pain compared to vehicle.

DETAILED DESCRIPTION OF THE INVENTION

Introduction

Figure 1A:
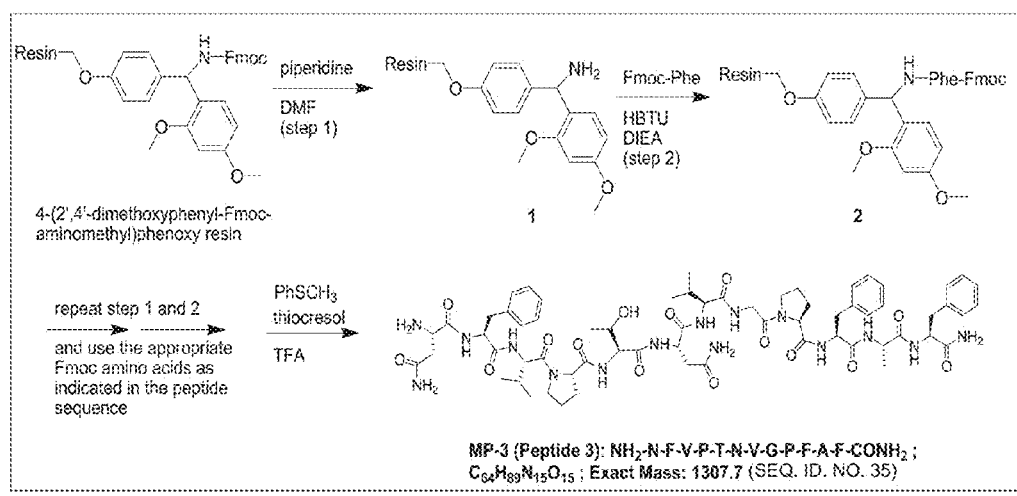
FIG. 1A. A scheme of the representative synthesis of AFA-peptide 3 (MP-3), and FIG. 1B. Five examples of newly designed and synthesized CGRP antagonist peptides AFA-peptide 1, 2, 3, 4 and 5 (also coded as MP 1, 2, 3, 4 and 5).

Calcitonin Gene-Related Peptide (CGRP) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to the CGRP receptor which is a heterodimer consisting of the G-protein coupled calcitonin-like receptor (CLR) in association with the single transmembrane protein known as receptor activity modifying protein 1 ($RAMP_1$). CGRP receptors are predominantly coupled to the activation of adenylyl cyclase and have been identified and pharmacologically evaluated in several tissues and cells, including those of brain, cardiovascular, endothelial, and smooth muscle origin.

CGRP is a potent neuromodulator that has been implicated in the pathology of cerebrovascular disorders such as migraine and cluster headache. In clinical studies, elevated levels of CGRP in the jugular vein were found to occur during migraine attacks (Goadsby, et al. (1990) Ann. Neurol. 28, 183-187), salivary levels of CGRP are elevated in migraine subjects between (Bellamy, et al. (2006) Headache 46, 24-33) and during attacks (Cady, et al. (2009) Headache 49, 1258-1266), and CGRP itself has been shown to trigger migrainous headache (Lassen, et al. (2002) Cephalalgia 22, 54-61). In clinical trials, the CGRP receptor antagonist BIBN4096BS has been shown to be effective in treating acute attacks of migraine (Olesen, et al. (2004) New Engl. J. Med. 350, 1104-1110) and was able to prevent headache induced by CGRP infusion in a control group (Petersen et al. (2005) Clin. Pharmacol. Ther. 77, 202-213). The orally bioavailable CGRP receptor antagonist telcagepant has also shown antimigraine effectiveness in phase III clinical trials (Ho et al. (2008) Lancet 372, 2115-2123; Connor et al. (2009) Neurology 73, 970-977).

CGRP-mediated activation of the trigeminovascular system may play a key role in migraine pathogenesis. Additionally, CGRP activates receptors on the smooth muscle of intracranial vessels, leading to increased vasodilation, which is thought to contribute to headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al. (1988) Ann. Neurol. 23, 193-196). Electrical stimulation of the dura mater in rats increased the diameter of the middle meningeal artery, an effect that was blocked by prior administration of CGRP (8-37), a peptide CGRP receptor antagonist (Williamson et al. (1997) Cephalalgia 17, 525-531). Trigeminal ganglion stimulation increased facial blood flow in the rat, which was inhibited by CGRP (8-37) (Escott et al. (1995) Brain Res. 669, 93-99). Electrical stimulation of the trigeminal ganglion in marmoset produced an increase in facial blood flow that could be blocked by the non-peptide CGRP receptor antagonist BIBN4096BS (Doods et al. (2000) Br. J. Pharmacol. 129, 420-423). Thus the vascular effects of CGRP may be attenuated, prevented or reversed by a CGRP receptor antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al. (2000) Ann. Neurol. 47, 614-624). A CGRP antagonist may be beneficial in attenuating, preventing or reversing the effects of neuronal sensitization.

The ability of the compounds of the present invention to act as CGRP receptor antagonists makes them useful pharmacological agents for disorders that involve CGRP in humans and animals, but particularly in humans. Such disorders include migraine and cluster headache (Doods (2001) Curr. Opin. Invest. Drugs 2, 1261-1268; Edvinsson et al. (1994) Cephalalgia 14, 320-327); chronic tension type headache (Ashina et al. (2000) Neurology 14, 1335-1340); pain (Yu et al. (1998) Eur. J. Pharmacol. 347, 275-282); chronic pain (Hulsebosch et al. (2000) Pain 86, 163-175); neurogenic inflammation and inflammatory pain (Holzer (1988) Neuroscience 24, 739-768; Delay-Goyet et al. (1992) Acta Physiol. Scanda. 146, 537-538; Salmon et al. (2001) Nature Neurosci. 4, 357-358); eye pain (May et al. (2002) Cephalalgia 22, 195-196), tooth pain (Awawdeh et al. (2002) Int. Endocrin. J. 35, 30-36), non-insulin dependent diabetes mellitus (Molina et al. (1990) Diabetes 39, 260-265); vascular disorders; inflammation (Zhang et al. (2001)

Pain 89, 265); arthritis, bronchial hyperreactivity, asthma, (Foster et al. (1992) *Ann. NY Acad. Sci.* 657, 397-404; Schini et al. (1994) *Am. J. Physiol.* 267, H2483-H2490; Zheng et al. (1993) *J. Virol.* 67, 5786-5791); shock, sepsis (Beer et al. (2002) *Crit. Care Med.* 30, 1794-1798); opiate withdrawal syndrome (Salmon et al. (2001) *Nature Neurosci.* 4, 357-358); morphine tolerance (Menard et al. (1996) *J. Neurosci.* 16, 2342-2351); hot flashes in men and women (Chen et al. (1993) *Lancet* 342, 49; Spetz et al. (2001) *J. Urology* 166, 1720-1723); allergic dermatitis (Wallengren (2000) *Contact Dermatitis* 43, 137-143); psoriasis; encephalitis, brain trauma, ischaemia, stroke, epilepsy, and neurodegenerative diseases (Rohrenbeck et al. (1999) *Neurobiol. Dis.* 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al. (2002) *J. Membr. Biol.* 189, 225); obesity (Walker et al. (2010) *Endocrinology* 151, 4257-4269); inflammatory bowel disease, irritable bowel syndrome, (Hoffman et al. (2002) *Scand. J. Gastroenterol.* 37, 414-422) and cystitis. Of particular importance is the acute or prophylactic treatment of headache, including migraine and cluster headache.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

In describing the present invention, the following terms will be employed, and are defined as indicated below.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

The term "subject" includes human and animal subjects. In certain embodiments, a subject is a mammal. In certain such embodiments, a subject is a human.

A "polypeptide" is an amino acid sequence comprising a plurality of consecutive polymerized amino acid residues e.g., at least 10 consecutive polymerized amino acid residues. In many instances, a polypeptide comprises a polymerized amino acid residue sequence that is a transcription factor or a domain or portion or fragment thereof. Additionally, the polypeptide may comprise: (i) a localization domain; (ii) an activation domain; (iii) a repression domain; (iv) an oligomerization domain; (v) a protein-protein interaction domain; (vi) a DNA-binding domain; or the like. The polypeptide optionally comprises modified amino acid residues, naturally occurring amino acid residues not encoded by a codon, non-naturally occurring amino acid residues.

"Protein" refers to an amino acid sequence, oligopeptide, peptide, polypeptide or portions thereof whether naturally occurring or synthetic.

A "fragment" of a polypeptide refers to a contiguous stretch of amino acids from any portion of the CGRP polypeptide. A fragment may be of any length that is less than the length of the reference polypeptide.

A "variant" of a CGRP polypeptide refers to a polypeptide having one or more amino acid substitutions, deletions, or insertions relative to the reference polypeptide.

A "recombinant polypeptide" is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild-type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such enrichment is not the result of a natural response of a wild-type plant. Alternatively, or additionally, the isolated polypeptide is separated from other cellular components with which it is typically associated, e.g., by any of the various protein purification methods herein.

"Homology" refers to sequence similarity between a reference sequence and at least a fragment of a newly sequenced clone insert or its encoded amino acid sequence.

"Identity" or "similarity" refers to sequence similarity between two polynucleotide sequences or between two polypeptide sequences, with identity being a more strict comparison. The phrases "percent identity" and "% identity" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value there between. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical, matching or corresponding nucleotides at positions shared by the polynucleotide sequences. A degree of identity of polypeptide sequences is a function of the number of identical amino acids at corresponding positions shared by the polypeptide sequences. A degree of homology or similarity of polypeptide sequences is a function of the number of amino acids at corresponding positions shared by the polypeptide sequences.

"Alignment" refers to a number of nucleotide bases or amino acid residue sequences aligned by lengthwise comparison so that components in common (i.e., nucleotide bases or amino acid residues at corresponding positions) may be visually and readily identified. The fraction or percentage of components in common is related to the homology or identity between the sequences. An alignment may suitably be determined by means of computer programs known in the art, such as MACVECTOR software (1999) (Accelrys, Inc., San Diego, Calif.), and the European Molecular Biology Open Software Suite (EMBOSS) Needle program (Rice, P., et al. 2000)

A "conserved domain" or "conserved region" as used herein refers to a region within heterogeneous polynucleotide or polypeptide sequences where there is a relatively high degree of sequence identity or homology between the distinct sequences. With respect to polynucleotides encoding presently disclosed polypeptides, a conserved domain is preferably at least nine base pairs (bp) in length. Protein sequences, including transcription factor sequences, that possess or encode for conserved domains that have a minimum percentage identity and have comparable biological activity to the present polypeptide sequences, thus being members of the same clade of transcription factor polypeptides, are encompassed by the instant disclosure. Reduced or eliminated expression of a polypeptide that comprises, for example, a conserved domain having DNA-binding, activation or nuclear localization activity, results in the transformed plant having similar improved traits as other transformed plants having reduced or eliminated expression of other members of the same clade of transcription factor polypeptides.

A fragment or domain can be referred to as outside a conserved domain, outside a consensus sequence, or outside a consensus DNA-binding site that is known to exist or that exists for a particular polypeptide class, family, or subfamily. In this case, the fragment or domain will not include the exact amino acids of a consensus sequence or consensus DNA-binding site of a transcription factor class, family or sub-family, or the exact amino acids of a particular transcription factor consensus sequence or consensus DNA-binding site. Furthermore, a particular fragment, region, or domain of a polypeptide, or a polynucleotide encoding a polypeptide, can be "outside a conserved domain" if all the amino acids of the fragment, region, or domain fall outside of a defined conserved domain(s) for a polypeptide or protein. Sequences having lesser degrees of identity but comparable biological activity are considered to be equivalents.

As one of ordinary skill in the art recognizes, conserved domains may be identified as regions or domains of identity to a specific consensus sequence. Thus, by using alignment methods well known in the art, the conserved domains of the plant polypeptides may be determined.

A "conservative" amino acid substitution refers to the substitution of an amino acid in a polypeptide with another amino acid having similar properties, such as size or charge. In certain embodiments, a polypeptide comprising a conservative amino acid substitution maintains at least one activity of the unsubstituted polypeptide. A conservative amino acid substitution may encompass non-naturally occurring amino acid residues, which are typically incorporated by chemical peptide synthesis rather than by synthesis in biological systems. These include, but are not limited to, peptidomimetics and other reversed or inverted forms of amino acid moieties.

Naturally occurring residues may be divided into classes based on common side chain properties: 1) hydrophobic: norleucine, Met, Ala, Val, Leu, Ile; 2) neutral hydrophilic: Cys, Ser, Thr, Asn, Gln; 3) acidic: Asp, Glu; 4) basic: His, Lys, Arg; 5) residues that influence chain orientation: Gly, Pro; and 6) aromatic: Trp, Tyr, Phe.

For example, non-conservative substitutions may involve the exchange of a member of one of these classes for a member from another class. Such substituted residues may be introduced into regions of a human CGRP polypeptide. In various embodiments, a hydrophobic amino acid is substituted by another hydrophobic amino acid, or a hydrophilic amino acid is substituted for another hydrophilic amino acid, at a desired location in the sequence. Alternatively, a hydrophobic amino acid may be substituted for a hydrophilic amino acid and vice-versa. Exemplary locations for such substitutions are at the N-terminus and/or the C-terminus.

More than one such substitution may be made. Positions inward from the termini may be substituted in addition to one or more of the termini or instead of the termini (e.g., C-1, C-2, C-3, C-4, C-5 . . . C-X; and/or N-1, N-2, N-3, N-4, N-5 . . . N-Y), in which X and Y are integers representing positions in the sequence inward of the respective terminus.

Substitutions of naturally occurring amino acids for non-naturally occurring amino acids may also be made. Exemplary non-naturally occurring acids include homo-amino acids, and amino acids substituted at one or more position with one or more substituted or unsubstituted alkyl, substituted or unsubstituted heteroalkyl, substituted or unsubstituted aryl, substituted or unsubstituted heteroaryl, substituted or unsubstituted cycloalkyl, substituted or unsubstituted acyl, nitro, cyano, hydroxy, amino, halo, carboxyl, carbonyl or azido residue. Exemplary locations for such modifications include the nitrogen atom of the N-terminus and the carboxyl carbon of the C-terminus, however, carbons within the amino acid backbone can also be modified, as can the aromatic rings of aromatic amino acids (e.g., phenylalanine).

In making substitutions, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein, in certain instances, is understood in the art. Kyte et al., *J. Mol. Biol.*, 157:105-131 (1982). It is known that in certain instances, certain amino acids may be substituted for other amino acids having a similar hydropathic index or score and still retain a similar biological activity. In making changes based upon the hydropathic index, in certain embodiments, the substitution of amino acids whose hydropathic indices are within ±0.2 is included. In certain embodiments, those which are within ±0.1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±0.1); glutamate (+3.0±0.1); serine (+0.3); asparagine (+0.2); glutamine (+0.2); glycine (0); threonine (−0.4); proline (−0.5±0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±0.2 is included, in certain embodiments, those which are within ±1 are included, and in certain embodiments, those within ±0.5 are included. One may also identify epitopes from primary amino acid sequences on the basis of hydrophilicity.

A skilled artisan is able to determine suitable variants of a polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, in certain embodiments, one skilled in the art can review structure-function studies identifying residues in similar polypeptides that are important for activity or structure. In view of such a comparison, in certain embodiments, one can predict the importance of amino acid residues in a protein that correspond to amino acid residues which are important for activity or structure in similar proteins. In certain embodiments, one skilled in the art may opt for chemically similar amino acid substitutions for such predicted important amino acid residues.

In certain embodiments, one skilled in the art can also analyze the three-dimensional structure and amino acid sequence in relation to that structure in similar polypeptides. In certain embodiments, in view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules. Moreover, in certain embodiments, one skilled in the art may generate test variants containing a single amino acid substitution at each desired amino acid residue. In certain embodiments, the variants can then be screened using activity assays known to those skilled in the art. In certain embodiments, such variants could be used to gather information about suitable variants. For example, in certain embodiments, if one discovered that a change to a particular amino acid residue resulted in destroyed, undesirably reduced, or unsuitable activity, variants with such a change may be avoided. In other words, in certain embodiments, based on information gathered from such routine experiments, one skilled in the art can readily determine the amino acids where further substitutions should be avoided either alone or in combination with other mutations.

A number of scientific publications have been devoted to the prediction of secondary structure. See, e.g., Moult J., *Curr. Op. in Biotech.*, 7(4):422-427 (1996), Chou et al., *Biochemistry*, 13(2):222-245 (1974); Chou et al., *Biochemistry*, 113(2):211-222 (1974); Chou et al., *Adv. Enzymol. Relat. Areas Mol. Biol.*, 47:45-148 (1978); Chou et al., *Ann. Rev. Biochem.*, 47:251-276 and Chou et al., *Biophys. J.*, 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The growth of the protein structural database (PDB) has provided enhanced predictability of secondary structure, including the potential number of folds within a polypeptide's structure. See, e.g., Holm et al., *Nucl. Acid. Res.*, 27(1):244-247 (1999). It has been suggested (Brenner et al., *Curr. Op. Struct. Biol.*, 7(3):369-376 (1997)) that there are a limited number of folds in a given polypeptide or protein and that once a critical number of structures have been resolved, structural prediction will become dramatically more accurate.

Additional methods of predicting secondary structure include "threading" (see, e.g., Jones, D., *Curr. Opin. Struct. Biol.*, 7(3):377-87 (1997); Sippl et al., *Structure*, 4(1):15-19 (1996)), "profile analysis" (see, e.g., Bowie et al., *Science*, 253:164-170 (1991); Gribskov et al., *Meth. Enzym.*, 183: 146-159 (1990); Gribskov et al., *Proc. Nat. Acad. Sci.*, 84(13):4355-4358 (1987)), and "evolutionary linkage" (see, e.g., Holm et al., *Nucl. Acid. Res.*, 27(1):244-247 (1999), and Brenner et al., *Curr. Op. Struct. Biol.*, 7(3):369-376 (1997)).

"Percent identity" or "% identity," with reference to nucleic acid sequences, refers to the percentage of identical nucleotides between at least two polynucleotide sequences aligned using the Basic Local Alignment Search Tool (BLAST) engine. See Tatusova et al. (1999) *FEMS Microbiol Lett.* 174:247-250. The BLAST engine (version 2.2.10) is provided to the public by the National Center for Biotechnology Information (NCBI), Bethesda, Md. To align two polynucleotide sequences, the "Blast 2 Sequences" tool can be used.

As used herein, the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, the terms "treat," and "prevent" as well as words stemming therefrom, do not necessarily imply 100% or complete treatment or prevention. Rather, there are varying degrees of treatment or prevention of which one of ordinary skill in the art recognizes as having a potential benefit or therapeutic effect. In this respect, the methods of the present invention can provide any amount of any level of treatment or prevention of a disease or medical condition in a mammal. Furthermore, the treatment or prevention provided by the method can include treatment or prevention of one or more conditions or symptoms of the disease or medical condition. For example, with regard to methods of treating pain, the method in some embodiments, achieves a diminution in or elimination of pain in a subject. Also, for purposes herein, "prevention" can encompass delaying the onset of the disease, or a symptom or condition thereof. The term "treating" includes prophylaxis of the specific disorder or condition, or alleviation of the symptoms associated with a specific disorder or condition and/or preventing or eliminating said symptoms. For example, as used herein the term "treating migraine" refers in general to producing a diminution or alleviation of pain associated with migraine.

As used herein an "effective" amount or a "therapeutically effective amount" of the isolated CGRP polypeptide of the invention refers to a nontoxic but sufficient amount of the peptide to provide the desired effect. For example one desired effect would be the prevention or treatment pain and/or inflammation. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route, e.g., subcutaneous, intramuscular, intraspinal, or intravenous.

The term "isolated" as used herein means having been removed from its natural environment. In some embodiments, the analog is made through recombinant methods and the analog is isolated from the host cell. The term "isolated," relates to the isolation of a molecule or compound in a form that is substantially free of contaminants normally associated with the molecule or compound in a native or natural environment and means having been increased in purity as a result of being separated from other components of the original composition.

The term "isolated polypeptide" is used herein to describe a polypeptide which can synthesized and/or has been separated from other compounds including, but not limited to nucleic acid molecules, lipids and carbohydrates. An "isolated polypeptide may be found in a pharmaceutical formulation also including a pharmaceutically acceptable diluent.

The term "agent" refers to a chemical compound, a mixture of chemical compounds, a biological macromolecule, or an extract made from biological materials.

A "therapeutic agent" refers to an agent that may be administered in vivo to bring about a therapeutic and/or prophylactic/preventative effect.

A "therapeutic polypeptide" refers to polypeptide that may be administered in vivo to bring about a therapeutic and/or prophylactic/preventative effect.

The terms "isolated nucleic acid" and "isolated polynucleotide" are used interchangeably and refer to a polynucleotide of genomic, cDNA, or synthetic origin or some combination thereof. An "isolated polynucleotide" (1) is not associated with all or a portion of a polynucleotide in which the "isolated polynucleotide" is found in nature, (2) is linked to a polynucleotide to which it is not linked in nature, or (3) does not occur in nature as part of a larger sequence.

"Compound of the invention," as used herein refers to the compounds discussed herein, pharmaceutically acceptable salts and prodrugs of these compounds.

"Biological medium," as used herein refers to both in vitro and in vivo biological milieus. Exemplary in vitro "biological media" include, but are not limited to, cell culture or extracts thereof, tissue culture or extracts thereof, homogenates or extracts thereof, biopsied material obtained from a mammal or extracts thereof; and blood, saliva, urine, feces, semen, tears, or other body fluids or extracts thereof. In vivo applications are generally performed in mammals, preferably humans.

"Somatic" pain, as described above, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

"Inhibiting" and "blocking," are used interchangeably herein to refer to the partial or full blockade of a voltage sodium gated channel by a compound of the invention, which leads to a decrease in ion flux either into or out of a cell in which a voltage-gated sodium channel is found.

The compounds of the invention being antagonists of the CGRP receptor, are useful in the treatment of a range of disorders. The treatment of pain, particularly neuropathic pain and/or inflammatory pain, is an exemplary use.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organized projection to the spinal cord, the location of the stimuli. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitization in the periphery, locally around the injury and centrally where the nociceptors terminate. These effects lead to a heightened sensation of pain. In acute pain these mechanisms can be useful, in promoting protective behaviors which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), posttraumatic pain, renal colic, cancer pain and back pain. Cancer pain may be chronic pain such as tumor related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, *Ann Pharmacother.*, 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

Idiopathic pain is pain of unknown origin, for example, phantom limb pain. Neuropathic pain is generally caused by injury or infection of the peripheral sensory nerves. It includes, but is not limited to pain from peripheral nerve trauma, herpes virus infection, diabetes mellitus, causalgia, plexus avulsion, neuroma, limb amputation and vasculitis. Neuropathic pain is also caused by nerve damage from chronic alcoholism, human immunodeficiency virus infection, hypothyroidism, uremia, or vitamin deficiencies.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
heart and vascular pain, including pain caused by angina, myocardical infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders; and
orofacial pain, including dental pain, otic pain, burning mouth syndrome and temporomandibular myofascial pain.

As set forth herein, the compositions, pharmaceutical formulations, methods and devices of the present invention are of use to treat and/or prevent one, more than one or all of the types of pain described hereinabove.

Where substituent groups are specified by their conventional chemical formulae, written from left to right, they equally encompass the chemically identical substituents, which would result from writing the structure from right to left, e.g., —CH$_2$O— is preferably intended to also recite —OCH$_2$—.

The term "alkyl," by itself or as part of another substituent, means, unless otherwise stated, a straight- or branched-chain, or cyclic hydrocarbon radical, or combination thereof, which may be fully saturated, mono- or polyunsaturated and can include mono-, di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, also preferably include those derivatives of alkyl defined in more detail below, such as "heteroalkyl." Alkyl groups that are limited to hydrocarbon groups are termed "homoalkyl". The term "alkyl", as used herein refers to alkyl, alkenyl and alkynyl moieties, each of which can be mono-, di- or polyvalent species. Alkyl groups are preferably substituted, e.g., with one or more group referred to hereinbelow as an "alkyl group substituent."

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight- or branched-chain, or cyclic alkyl radical consisting of the stated number of carbon atoms and at least one heteroatom selected from the group consisting of B, O, N, Si and S, wherein the heteroatom may optionally be oxidized and the nitrogen atom may optionally be quantized. The heteroatom(s) may be placed at any internal position of the heteroalkyl group or at a terminus of the chain, e.g., the position through which the alkyl group is attached to the remainder of the molecule. Examples of "heteroalkyl" groups include, but are not limited to, —CH$_2$—CH$_2$—O—CH$_3$, —CH$_2$—CH$_2$—NH—CH$_3$, —CH$_2$—CH$_2$—N (CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, and —CH═CH—N(CH$_3$)—CH$_3$. Two or more heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent refers to a substituted or unsubstituted divalent heteroalkyl radical, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents —C(O)$_2$R'— and, preferably, —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings, one or more of which is optionally a cycloalkyl or heterocycloalkyl), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of "aryl group substituents" described below.

For brevity, the term "aryl" when used in combination with other terms (e.g., aryloxy, arylthioxy, arylalkyl) preferably includes both homoaryl and heteroaryl rings as defined above. Thus, the term "arylalkyl" optionally includes those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', ═O, ═NR', ═N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR""—C(NR'R"R'")═NR'", —NR""—C(NR'R")═NR'", —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl in a number ranging from zero to (2 m'+1), where m' is the total number of carbon atoms in such radical. R', R", R'", R"" and R""' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'", R"" and R""' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" includes groups with carbon atoms bound to groups other than hydrogen, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: —R', —OR', ═O, ═NR', ═N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR""—C(NR'R"R'")═NR'", —NR""—C(NR'R")═NR'", —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$) alkoxy, and fluoro(C$_1$-C$_4$)alkyl, in a number ranging from zero to the total number of open valences on the aromatic ring system; and where R', R", R'", R"" and R""' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'", R"" and R""' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R"')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

As used herein, the term "heteroatom" includes oxygen (O), nitrogen (N), sulfur (S) and silicon (Si).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclyl groups.

The term "salt(s)" includes salts of the compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts.

When the compound prepared by a method of the invention is a pharmacological agent, the salt is preferably a pharmaceutically acceptable salt. Examples of pharmaceutically acceptable salts are presented hereinabove, and are generally known in the art. See, for example, Wermuth, C., PHARMACEUTICAL SALTS: PROPERTIES, SELECTION AND USE—A HANDBOOK, Verlag Helvetica Chimica Acta (2002)

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds that are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

As used herein, and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise NO, NO$_2$, —ONO, or —ONO$_2$ moieties. The term "prodrug" is accorded a meaning herein such that prodrugs do not encompass the parent compound of the prodrug. When used to describe a compound of the invention, the term "prodrug" may also to be interpreted to exclude other compounds of the invention.

As used herein, and unless otherwise indicated, the terms "biohydrolyzable carbamate," "biohydrolyzable carbonate," "biohydrolyzable ureide" and "biohydrolyzable phosphate" mean a carbamate, carbonate, ureide and phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, and unless otherwise indicated, the term "biohydrolyzable ester" means an ester of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters.

As used herein, and unless otherwise indicated, the term "biohydrolyzable amide" means an amide of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable amides include, but are not limited to, lower alkyl amides, α-amino acid amides, alkoxyacyl amides, and alkylaminoalkylcarbonyl amides.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

As used herein, and unless otherwise indicated, a composition that is "substantially free" of a compound means that the composition contains less than about 20% by weight, more preferably less than about 10% by weight, even more preferably less than about 5% by weight, and most preferably less than about 3% by weight of the compound.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

EXEMPLARY EMBODIMENTS

Compositions

Calcitonin gene-related peptide (CGRP) is a 37-amino acid neuropeptide produced by tissue specific processing of the calcitonin gene and is the major product in neural tissues. CGRP is released by motor neurons where it exerts both short and long term effects on skeletal muscle fibers. In addition, sensory neurons release CGRP to the surrounding vasculature where it is partly responsible for local vasodilation following muscle contraction. CGRP acts through G protein-coupled receptors whose presence and changes in function modulate the peptide's effects in various tissues.

The sequence of full-length, wild type human CGRP is set forth in SEQ. ID. NO.: 1:

```
ACDTATCVTHRLAGLLSRSGGVVKNNFVPTNVGSKAF-NH2

(Disulfide bridge: 2-7),
``` equivalently displayed as:

```
H-Ala-Cys-Asp-Thr-Ala-Thr-Cys-Val-Thr-His-Arg-Leu-

Ala-Gly-Leu-Leu-Ser-Arg-Ser-Gly-Gly-Val-Val-Lys-

Asn-Asn-Phe-Val-Pro-Thr-Asn-Val-Gly-Ser-Lys-Ala-

Phe-NH2 (Disulfide bridge: 2-7).
```

Both representations of this sequence are referred to herein as SEQ. ID. NO.: 1.

In an exemplary embodiment, the invention provides an isolated polypeptide that comprises a sequence having at least 90% sequence identity with amino acids 8-37 of wild type human CGRP. Wild type human CGRP is set forth in SEQ. ID. NO.: 1.

In various embodiments, the invention provides an isolated polypeptide of the formula:

$$R^1R^2N\text{-}X^a\text{-}(X^b)_n\text{-}(X^c)\text{-}PTNVGPFAF\text{-}CR^3, \quad \text{(SEQ. ID. NO. 2)}$$

in which $R^1$ and $R^2$ are independently selected from H, substituted or unsubstituted alkyl, substituted or unsubstituted aryl, substituted or unsubstituted heteroaryl, substituted or unsubstituted heterocycloalkyl, and acyl. $X^a$, $X^b$ and $X^c$ are independently selected from naturally occurring or non-naturally occurring amino acids. In various embodiments, the amino acid is an alpha amino acid. The index n is an integer selected from 0, 1, 2, 3, 4, 5, 6 7, 8, 9, 10 or greater. When n is two or greater, the amino acid at position $X^b$ is an oligopeptide. $R^3$ is $BR^4R^5$, CN, $CF_3$, acyl, $-SO_2NR^4R^5$, $-NR^4R^5$, $-OR^4$, $-S(O)_2R^4$, $-C(O)R^4$, $-COOR^4$, $-CONR^4R^5$, $-S(O)_2OR^4$, $-OC(O)R^4$, $-C(O)NR^4R^5$, $-NR^4C(O)R^5$, $-NR^4SO_2R^5$ and $-NO_2$.

In various embodiments, $X^a$, $X^b$ and $X^c$ are independently selected from F, N, L, D, V, W, A, and I. In various embodiments, $X^a$ is selected from F, N, W, and D. In various embodiments, $X^b$ is present or absent and, when present, is selected from F, I, N, L and V. In various embodiments, $X^c$ is selected from A, F, V, L, and I. In an exemplary embodiment, the index n is 2, and the oligopeptide at this position is a dipeptide and is NF.

$R^4$ and $R^5$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. Optionally, $R^4$ and $R^5$, together with the atoms to which they are bonded, are joined to form a 5- to 7-membered ring which is a member selected from substituted or unsubstituted cycloalkyl, substituted or unsubstituted heterocycloalkyl, substituted or unsubstituted aryl and substituted or unsubstituted heteroaryl.

Optionally, two or more of $R^1$, $R^2$, $R^3$, $R^4$ and $R^5$ together with the atoms to which they are bonded, are joined to form a ring system which is a member selected from substituted or unsubstituted cycloalkyl, substituted or unsubstituted heterocycloalkyl, substituted or unsubstituted aryl and substituted or unsubstituted heteroaryl.

In various embodiments, the invention provides peptides according to the formulae:

```
(SEQ. ID. NO.: 3):
R¹R²N-F-V-P-T-N-V-G-P-F-A-F-CR³;

(SEQ. ID. NO.: 4):
R¹R²N-F-I-P-T-N-V-G-P-F-A-F-CR³;

(SEQ. ID. NO.: 5):
R¹R²N-N-F-V-P-T-N-V-G-P-F-A-F-CR³;

(SEQ. ID. NO.: 6):
R¹R²N-W-V-P-T-N-V-G-P-F-A-F-CR³;

(SEQ. ID. NO.: 7):
R¹R²N-D-N-F-V-P-T-N-V-G-P-F-A-F-CR³;

(SEQ. ID. NO.: 8):
R¹R²N-N-F-I-P-T-N-V-G-P-F-A-F-CR³;

(SEQ. ID. NO.: 9):
R¹R²N-N-F-L-P-T-N-V-G-P-F-A-F-CR³;

(SEQ. ID. NO.: 10):
R¹R²N-N-L-V-P-T-N-V-G-P-F-A-F-CR³;
```

-continued (SEQ. ID. NO.: 11):
$R^1R^2$N-N-F-F-P-T-N-V-G-P-F-A-F-$CR^3$;
or (SEQ. ID. NO.: 12):
$R^1R^2$N-N-F-A-P-T-N-V-G-P-F-A-F-$CR^3$.

In various embodiments, the peptides of the invention are of the formula:

(SEQ. ID. NO.: 13):
$NH_2$-F-V-P-T-N-V-G-P-F-A-F-$CR^3$;

(SEQ. ID. NO.: 14):
$NH_2$-F-I-P-T-N-V-G-P-F-A-F-$CR^3$;

(SEQ. ID. NO.: 15):
$NH_2$-N-F-V-P-T-N-V-G-P-F-A-F-$CR^3$;

(SEQ. ID. NO.: 16):
$NH_2$-W-V-P-T-N-V-G-P-F-A-F-$CR^3$;

(SEQ. ID. NO.: 17):
$NH_2$-D-N-F-V-P-T-N-V-G-P-F-A-F-$CR^3$;

(SEQ. ID. NO.: 18):
$NH_2$-N-F-I-P-T-N-V-G-P-F-A-F-$CR^3$;

(SEQ. ID. NO.: 19):
$NH_2$-N-F-L-P-T-N-V-G-P-F-A-F-$CR^3$;

(SEQ. ID. NO.: 20):
$NH_2$-N-L-V-P-T-N-V-G-P-F-A-F-$CR^3$;

(SEQ. ID. NO.: 21):
$NH_2$-N-F-F-P-T-N-V-G-P-F-A-F-$CR^3$;
or (SEQ. ID. NO.: 22):
$NH_2$-N-F-A-P-T-N-V-G-P-F-A-F-$CR^3$.

In various embodiments, the peptides of the invention have a formula selected from:

(SEQ. ID. NO.: 23):
$R^1R^2$N-F-V-P-T-N-V-G-P-F-A-F-$CONH_2$;

(SEQ. ID. NO.: 24):
$R^1R^2$N-F-I-P-T-N-V-G-P-F-A-F-$CONH_2$;

(SEQ. ID. NO.: 25):
$R^1R^2$N-N-F-V-P-T-N-V-G-P-F-A-F-$CONH_2$;

(SEQ. ID. NO.: 26):
$R^1R^2$N-W-V-P-T-N-V-G-P-F-A-F-$CONH_2$;

(SEQ. ID. NO.: 27):
$R^1R^2$N-D-N-F-V-P-T-N-V-G-P-F-A-F-$CONH_2$;

(SEQ. ID. NO.: 28):
$R^1R^2$N-N-F-I-P-T-N-V-G-P-F-A-F-$CONH_2$;

(SEQ. ID. NO.: 29):
$R^1R^2$N-N-F-L-P-T-N-V-G-P-F-A-F-$CONH_2$;

(SEQ. ID. NO.: 30):
$R^1R^2$N-N-L-V-P-T-N-V-G-P-F-A-F-$CONH_2$;

(SEQ. ID. NO.: 31):
$R^1R^2$N-N-F-F-P-T-N-V-G-P-F-A-F-$CONH_2$;
and (SEQ. ID. NO.: 32):
$R^1R^2$N-N-F-A-P-T-N-V-G-P-F-A-F-$CONH_2$.

In still further embodiments, the peptides of the invention have a formula selected from:

(MP-1; SEQ. ID. NO.: 33):
$NH_2$-F-V-P-T-N-V-G-P-F-A-F-$CONH_2$;

(MP-2; SEQ. ID. NO.: 34):
$NH_2$-F-I-P-T-N-V-G-P-F-A-F-$CONH_2$;

(MP-3; SEQ. ID. NO.: 35):
$NH_2$-N-F-V-P-T-N-V-G-P-F-A-F-$CONH_2$;

(MP-4; SEQ. ID. NO.: 36):
$NH_2$-W-V-P-T-N-V-G-P-F-A-F-$CONH_2$;

(MP-5; SEQ. ID. NO.: 37):
$NH_2$-D-N-F-V-P-T-N-V-G-P-F-A-F-$CONH_2$;

(MP-6; SEQ. ID. NO.: 38):
$NH_2$-N-F-I-P-T-N-V-G-P-F-A-F-$CONH_2$;

(MP-7; SEQ. ID. NO.: 39):
$NH_2$-N-F-L-P-T-N-V-G-P-F-A-F-$CONH_2$;

(MP-8; SEQ. ID. NO.: 40):
$NH_2$-N-L-V-P-T-N-V-G-P-F-A-F-$CONH_2$;

(MP-9; SEQ. ID. NO.: 41):
$NH_2$-N-F-F-P-T-N-V-G-P-F-A-F-$CONH_2$;
and (MP-10; SEQ. ID. NO.: 42):
$NH_2$-N-F-A-P-T-N-V-G-P-F-A-F-$CONH_2$.

In an exemplary embodiment, the invention is a compound described in the Examples.

Also within the scope of the present invention are compounds of the invention that are poly- or multi-valent species, including, for example, species such as dimers, trimers, tetramers and higher homologs of the compounds of the invention or reactive analogues thereof. The poly- and multi-valent species can be assembled from a single species or more than one species of the invention. For example, a dimeric construct can be "homo-dimeric" or "heterodimeric." Moreover, poly- and multi-valent constructs in which a compound of the invention or a reactive analogue thereof, can be attached to an oligomeric or polymeric framework (e.g., polylysine, dextran, hydroxyethyl starch and the like) are within the scope of the present invention. The framework is preferably polyfunctional (i.e., having an array of reactive sites for attaching compounds of the invention). Moreover, the framework can be derivatized with a single species of the invention or more than one species of the invention.

Moreover, the present invention includes compounds within a motif described herein, which are functionalized to afford compounds having water-solubility that is enhanced relative to analogous compounds that are not similarly functionalized. Thus, any of the substituents set forth herein can be replaced with analogous radicals that have enhanced water solubility. For example, it is within the scope of the invention to, for example, replace a hydroxyl group with a diol, or an amine with a quaternary amine, hydroxy amine or similar more water-soluble moiety. In a preferred embodiment, additional water solubility is imparted by substitution at a site not essential for the activity towards the ion channel of the compounds set forth herein with a moiety that enhances the water solubility of the parent compounds. Methods of enhancing the water-solubility of organic compounds are known in the art. Such methods include, but are not limited to, functionalizing an organic nucleus with a permanently charged moiety, e.g., quaternary ammonium, or a group that is charged at a physiologically relevant pH, e.g. carboxylic acid, amine. Other methods include, appending to the organic nucleus hydroxyl- or amine-containing groups, e.g. alcohols, polyols, polyethers, and the like. Representative examples include, but are not limited to, polylysine, polyethyleneimine, poly(ethyleneglycol) and poly(propylene glycol). Suitable functionalization chemistries and strategies for these compounds are known in the art. See, for example, Dunn, R. L., et al., Eds. *Polymeric Drugs and Drug Delivery Systems*, ACS Symposium Series Vol. 469, American Chemical Society, Wash., D. C. 1991.

The routes below, including those mentioned in the Examples synthesizing the compounds of the invention. The skilled person will appreciate that the compounds of the invention, and intermediates thereof, could be made by methods other than those specifically described herein, for example by adaptation of the described methods or by modification of methods known in the art. Examples of suitable guides to synthesis, functional group interconversions, use of protecting groups, etc., are: "Comprehensive Organic Transformations" by RC Larock, VCH Publishers Inc. (1989); Advanced Organic Chemistry" by J. March, Wiley Interscience (1985); "Designing Organic Synthesis" by S Warren, Wiley Interscience (1978); "Organic Synthesis—The Disconnection Approach" by S Warren, Wiley Interscience (1982); "Guidebook to Organic Synthesis" by R K Mackie and D M Smith, Longman (1982); "Protective Groups in Organic Synthesis" by T W Greene and P G M Wuts, John Wiley and Sons, Inc. (1999); "Protecting Groups" by P J, Kocienski, Georg Thieme Verlag (1994); and any updated versions of said standard works.

A number of experimental models in the rat are appropriate for assessing the in vivo efficacy of the compounds of the invention. For example, the neuropathic pain model produced by the tight ligation of spinal nerves, described by Kim et al., *Pain*, 50: 355-363 (1992), can be used to experimentally determine the effect of the compounds of the invention in an in vivo model of pain. Mechanical sensitivity can also be assessed using a procedure described by Chaplan et al., *J. Neurosci. Methods*, 53: 55-63 (1994). Other assays of use are known to those of skill in the art.

Pharmaceutical Formulations

In an exemplary embodiment, the invention provides a pharmaceutical formulation including a compound of the invention described herein, and one or more pharmaceutically acceptable diluents, carriers, vehicles, excipients, etc. The invention also encompasses a pharmaceutical composition which comprises an inert carrier and the compound of the invention, or a pharmaceutically acceptable salt thereof.

The invention is also directed to medicaments or pharmaceutical compositions for treating diseases or disorders in which CGRP is involved, such as migraine, which comprise a compound of the invention, or a pharmaceutically acceptable salt thereof, and a pharmaceutically acceptable carrier.

The compounds of the present invention may be used in conjunction with other agents to treat pain, inflammation or other diseases or conditions. For example, in one embodiment, a compounds of the invention is combined with an anti-migraine agent, such as ergotamine and dihydroergotamine, or other serotonin agonists, especially a 5-HT$_{1B/1D}$ agonist, for example sumatriptan, naratriptan, zolmitriptan, eletriptan, almotriptan, frovatriptan, donitriptan, and rizatriptan, a 5-HT$_{1D}$ agonist such as PNU-142633 and a 5-HT$_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; dexamethasone, or glucocorticoids. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrin precursor; anti-anxiety agents such as diazepam, alprazolam, chlordiazepoxide and chlorazepate; serotonin 5HT$_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocornine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with antiemetics.

In an embodiment of the invention the present compounds are used in conjunction with an anti-migraine agent, such as: ergotamine or dihydroergotamine; a 5-$HT_1$ agonist, especially a 5-$HT_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., subcutaneous, intramuscular, intraperitoneal, intravenous, intrathecal, intracerebroventricular, intracisternal injection or infusion, subcutaneous injection, or implant), by inhalation spray, nasal, vaginal, rectal, sublingual, buccal or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The compounds of the present invention can be prepared and administered in a wide variety of oral, parenteral and topical dosage forms. Thus, the compounds of the present invention can be administered by injection, that is, subcutaneously, intracutaneously, intramuscularly, intravenously, intraduodenally, subdural, epidural, or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and either a compound described herein, or a pharmaceutically acceptable salt of a compound described herein.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Methods

The invention also provides method of using the compounds to treat and/or prevent a disease or condition in a subject in need of such treatment. In an exemplary embodiment, the compound of the invention is used to ameliorate or prevent pain.

In an exemplary embodiment, the condition treated by administration of a therapeutically useful amount of a compound of the invention is pain. Various types of pain can be treated by the compounds of the invention including, without limitation, acute pain, chronic pain, visceral pain, inflammatory pain and neuropathic pain. Exemplary embodiments of this method are described in greater detail herein.

The compounds, compositions and methods of the present invention are of particular use in treating pain, including both inflammatory and neuropathic pain. Exemplary forms of pain treated by a compound of the invention include, postoperative pain, osteoarthritis pain, pain associated with metastatic cancer, neuropathy secondary to metastatic inflammation, trigeminal neuralgia, glossopharangyl neuralgia, adiposis dolorosa, burn pain, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, pain following stroke, thalamic lesions, radiculopathy, and other forms of neuralgic, neuropathic and idiopathic pain syndromes.

In various embodiments, the invention provides a method of local injection of one or more of an analgesic and/or anti-inflammatory therapeutic composition of the invention into the dermis layer of the skin. Injection may be made using a conventional metal needle or through a plurality of microneedles. In an exemplary embodiment, the administration is via a skin patch, wherein the pharmaceutical skin patch has several layers. For example, one layer of the pharmaceutical skin patch may comprise an adhesive portion to anchor the patch to the patient's skin, or a separate layer with an adhesive portion may be placed over the patch to hold it in place during administration of the therapeutic. An exemplary skin patch of use in the invention comprises a plurality of microneedles that contain a therapeutically effective amount of an active polypeptide of the invention (e.g., CGRP 8-37) in a carrier vehicle composition that is suitable for intradermal administration. An exemplary patch includes the compound of the invention in one or more reservoir layers or reservoir wells in an amount sufficient to supply a therapeutically effective amount of the composition to one or more microneedles of the patch.

Thus, in one embodiment, the invention provides a method of local intradermal administration according of a compound of the invention. In an exemplary embodiment, the compound is administered in conjunction with a therapeutically effective amount of one or more members selected from the group comprising a steroid, a NSAID or sodium channel blocker. Exemplary steroids include dexamethasone, the NSAID is ibuprofen, and the sodium channel blocker is lidocaine or bupivacaine or saxitoxin. In various embodiments, the sodium channel blocker is lidocaine, bupivacaine or saxitoxin, or a derivative thereof. The injection, or the skin patch may independently comprise one or more of said members in combination with the effective amount of the composition of the invention in a carrier vehicle in the same or separate portion of said patch.

In various embodiments, the local intradermal administration is made by injection at the peripheral site of sensory nerve endings in a patient experiencing pain or an inflammatory condition that is in need of therapeutic treatment.

Exemplary types of pain treatable by a method of the invention include, without limitation, incision pain, postoperative pain, surgical wound pain, neuroma, osteoarthritic, arthritis joint, low back, posttraumatic, and neuropathic pain, and diabetic neuropathy. In an exemplary embodiment, the pain is neurogenic inflammatory pain. Exemplary forms of neurogenic inflammatory pain include migraine pain, tension headache pain, burn pain, radiation pain, erythromelalgia, and complex regional pain syndrome, or cancer pain.

The ability of the compounds of the present invention to act as CGRP receptor antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; obesity; inflammatory bowel disease, irritable bowel syndrome, cystitis; chronic pancreatitis, and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the aforementioned diseases, disorders and conditions in combination with other agents.

The invention also encompasses a method of treating headache in a mammalian subject in need of such treatment, which comprises administering to the patient a therapeutically effective amount of a compound of the invention, or a pharmaceutically acceptable salt thereof. In a specific embodiment of the invention, the headache is migraine headache.

The invention also encompasses the use of a compound of the invention, or a pharmaceutically acceptable salt thereof, and a pharmaceutically acceptable carrier, for the manufacture of a medicament for the treatment of headache. In a specific embodiment of the invention, the headache is migraine headache.

In an exemplary embodiment, the invention provides the use of the compound of the invention described herein, in the manufacture of a medicament for the treatment of a disease or condition for which antagonism of a CGRP receptor is indicated, e.g., pain. In an exemplary embodiment, the invention provides the use of the compound of the invention, in the manufacture of a medicament for the treatment of a disease or condition for which antagonism of a CGRP receptor is indicated, e.g., pain. In an exemplary embodiment, the invention provides the use of a compound of the invention in the manufacture of a medicament for the treatment of a disease or condition for which a CGRP receptor antagonist is indicated, preferably pain.

In an exemplary embodiment, the invention provides a method of antagonizing a CGRP receptor in a subject or a biological media. This method comprises administering to a subject or biological media an amount of a compound of the invention sufficient to modulate said activity. Methods of detecting and amplifying antagonism of CGRP receptors are generally known in the art. A representative method is set forth herein.

The methods provided in this embodiment of the invention are useful for the diagnosis of conditions that can be treated by antagonizing CGRP receptors, or for determining if a patient will be responsive to therapeutic agents, which act by antagonizing a CGRP receptor.

The utility of the compounds in accordance with the present invention as antagonists of CGRP receptor activity may be demonstrated by methodology known in the art. See, e.g., Example 2 and Example 3.

In antagonizing CGRP and treatment of the above conditions, in various embodiments, the compounds utilized in the method of the invention are administered at the initial dosage of about 0.001 mg/kg to about 1000 mg/kg daily. A daily dose range of about 0.1 mg/kg to about 100 mg/kg is more typical. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day, if desired.

Devices

A further embodiment of the present invention provides improved devices for delivering locally to a subject one or more of the anti-pain compositions according to the invention as described above in a therapeutic amount effective to provide local pain relief and to reduce associated inflammatory pain in a mammal while reducing undesired systemic side-effects.

An exemplary embodiment of the invention provides a safer, more effective and more convenient system for delivering anti-pain compositions as therapeutics for localized or systemic neuropathic pain. A still further embodiment of the present invention provides a device for treating local or peripheral pain by one or more intradermal injections of one or more pain relieving compositions according to the invention at or near the site of pain.

Another embodiment of the invention provides a device for treating local neurogenic pain, in the form of a migraine or tension headache in patient in need thereof by local injection of one or more pain relieving compositions according to the invention at or near a site of pain. A particularly preferred object of the invention comprises a device for intradermal injection of a composition according to the invention on the neck of a patient, which is preferably at the back of the neck or at the nape of the neck.

An exemplary embodiment of the invention provides apparatus and compositions for a time released intradermal injection of one or more therapeutic compositions according to the present invention to provide a mammal with local relief of peripheral pain or relief from a migraine or tension headache.

A yet further embodiment of the invention comprises an apparatus for sustained pain relief wherein the apparatus comprises a plurality of layers with at least one outer sealing layer, at least one optional middle substrate layer as a storage receptacle for one or more pharmaceutical compositions according to the invention and at least one bottom layer comprising a plurality of intradermal injection microneedles that are connected to or include within the core of the microneedles at least one time release supply of a pain relieving therapeutic composition according to the present invention. An exemplary embodiment of the present invention comprises a unit dose pharmaceutical as described above in a microneedle patch made of either bio-absorbable, bio-dissolvable or both bio-absorbable and bio-dissolvable safe materials (Know U.S. Pat. No. 8,062,573)(Chong et al., 2013).

In various embodiments, the present invention provides a unit dose sustained release patch apparatus that is a pharmaceutical dermis injection patch including a plurality of intradermal injection microneedles, e.g., fabricated in whole or in part from plastic, metal, bio-absorbable or bio-dissolvable portions that may be optionally connected to at least one time release supply substrate layer of an anti-pain therapeutic composition according to the present invention. An exemplary apparatus is adapted to treating pain located at one or more of hands, elbow, shoulder, neck, legs, hip, or back, by delivering a sustained pain relieving dose of the composition(s) intradermally by injection at a site local or proximal to the pain origin.

The outer barrier of skin is the corneal layer or stratum corneum (outer skin layer cuticle), between 10-20 µm thick and this layer is a major barrier against penetration of compositions and limits drug delivery. The epidermis and dermis are typically 50-100 µm and 1-2 mm in thickness, respectively. Both nerve and vascular supplies are found in the dermis layer. The therapeutic composition delivery apparatus according to the invention is adapted to comprise microneedles capable of penetrating both of the outer layers of skin and to provide effective and efficient delivery to the inner dermis layer. In one embodiment, the apparatus is further adapted as a unit dose apparatus that is a timed or sustained delivery vehicle for steadily delivering a therapeutically effective amount of one or more composition according to the invention directly to the dermis layer where nerves ending are located. In a further preferred embodiment, the pharmaceutical dermis injection patch is a disposable patch and a portion of which is one or more of bio-absorbable, bio-dissolvable or bio-degradable.

In an exemplary embodiment, a compound of the invention is loaded in to the device. The device optionally is charged with at least a second therapeutic agent, e.g., an analgesic or anti-inflammatory. The devices of the invention are of use in methods for delivering therapeutic substances will be employed according to the applications. For example, transdermally (TD) or intradermally (ID) for chronic pain with intact skin; topical application to inflammatory skin (with an increased permeability) and incision or wound; conventional metal injection locally to deeper tissues (for example to treat neuroma).

In accordance with the unit dose anti-pain and anti-inflammatory therapeutic apparatus of the invention, administration to the intradermal spaces of the skin can be achieved using a needle injection, microneedle-based injection and infusion systems, or any other needle-less or needle-free ballistic injection of fluids or powders into the intradermal space. Mantoux-type intradermal injection, enhanced ionotophoresis through microdevices, laser illumination at clinical safe-doses using a laser device, and direct deposition of fluid, solids, or other dosing forms, including but not limited to hydrogel, or nanoparticles into the intradermal spaces for sustained release are of use in the invention. Preferably, micro-projection array technologies are used to create small channels in the stratum corneum of the skin down to the dermis layer into which one or more therapeutic compositions is administered. Because of their small size, 1-10 μm in tip diameter, 100-2,000 μm in length, this technology may be referred to as microneedles or microneedle arrays. A number of different microneedle array technologies for drug delivery have been described in the art. The silicon fabrication techniques widely used in making microchips have often been utilized to create very precise microneedles. More preferably, the present invention utilizes microneedle patches that are composed of biocompatible fast dissolving, nontoxic needles that possess the structural integrity to be inserted into the skin, yet allow the needles to dissolve upon contact with the interstitial fluid and finally portions are safely removed or are otherwise eliminated from the body.

Unless otherwise specified, the term "intradermal space" as used herein refers to the skin compartment known as the dermis that is located beneath the epidermis. The dermis includes the papillary dermis and the reticular dermis. Typically, intradermal administration involves depositing an agent into the skin at a depth of from about 0.2 mm to about 2 mm.

An exemplary embodiment of the invention provides a unit dose of a pain relieving composition according to the invention contained in a delivery device of the invention, which delivers the compound through local intranasal administration. In an exemplary embodiment, the compound is dissolved in a suitable carrier vehicle. Such devices are of use to treat a migraine, tension headache or trigeminal neuralgia in patients in need at or near a site of pain.

In a preferred embodiment, the invention provides therapeutic pharmaceutical skin patches for injecting one or more of an anti-pain or anti-inflammatory therapeutic composition into the dermis layer of the skin through a plurality of microneedles. An exemplary pharmaceutical skin patch has a plurality of layers, e.g., one layer of the pharmaceutical skin patch may comprise an adhesive portion to anchor the patch to the patient's skin. Alternatively, a separate layer with an adhesive portion may be placed over the patch to hold it in place during administration of the therapeutic. An exemplary pharmaceutical skin patch comprises a plurality of microneedles that may contain in a portion of one or more of the plurality of microneedles a therapeutically effective amount of an active polypeptide of the invention in a carrier vehicle composition that is suitable for intradermal administration by injection. An exemplary patch is configured for injection at the peripheral site of sensory nerve endings in a patient. An exemplary patch includes one or more reservoir layers or reservoir wells of the supplying an effective amount of the composition to one or more microneedles of the patch, wherein the supply of the pharmaceutical composition of said skin patch comprise a therapeutic effective amount of a composition for treating a patient experiencing pain or an inflammatory condition.

An exemplary pharmaceutical skin patch further comprises a therapeutically effective amount of a second analgesic or anti-inflammatory agent, e.g., one or more members selected from the group comprising a steroid, a NSAID or sodium channel blocker. In an exemplary pharmaceutical skin patch, the steroid is dexamethasone, the NSAID is ibuprofen, and the sodium channel blocker is either lidocaine or saxitoxin. An exemplary patch comprises a unit dose of the therapeutic composition located in a layer of the skin patch, within one or more of the plurality of microneedles, or both.

The following examples are offered to illustrate, but not to limit, the claimed invention.

Example 1. Synthesis of Peptides

In the examples below, unless otherwise stated, temperatures are given in degrees Celsius ° C.); operations were carried out at room or ambient temperature (typically a range of from about 18-25° C.; evaporation of solvent was carried out using a rotary evaporator under reduced pressure (typically, 4.5-30 mmHg) with a bath temperature of up to 60° C.; the course of reactions was typically followed by TLC and reaction times are provided for illustration only; melting points are uncorrected. The following conventional abbreviations are also used: mp (melting point), L (liter(s)), mL (milliliters), mmol (millimoles), g (grams), mg (milligrams), min (minutes), LC-MS (liquid chromatography-mass spectrometry) and h (hours), PS (polystyrene), DIE (diisopropylethylamine). $^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The mass spectra (MS) were recorded using either electrospray ionization (ESI) or atmospheric pressure chemical ionization (APCI). The following abbreviations have been used for common solvents: CDCl$_3$, deuterochloroform; d$_6$-DMSO, deuterodimethylsulphoxide; CD$_3$OD, deuteromethanol; D$_2$O deuterated water; THF, tetrahydrofuran. LCMS indicates liquid chromatography mass spectrometry (R$_t$=retention time). Six methods are used, these are shown below:

Synthesis

AFA-CGRP Antagonist Peptides (AFA-Peptides) Compositions

For references, the sequence of natural human CGRP 1-37 is Ala-Cys-Asp-Thr-Ala-Thr-Cys-Val-Thr-His-Arg-Leu-Ala-Gly-Leu-Leu-Ser-Arg-Ser-Gly-Gly-Val-Val-Lys-Asn-Asn-Phe-Val-Pro-Thr-Asn-Val-Gly-Ser-Lys-Ala-Phe-NH$_2$. SEQ. TD. NO.: 1.

The human CGRP 8-37 is a segment of human CGRP 1-37, which sequence is Val-Thr-His-Arg-Leu-Ala-Gly- Leu-Leu-Ser-Arg-Ser-Gly-Gly-Met-Val-Lys-Ser-Asn-Phe-Val-Pro-Thr-Asn-Val-Gly-Ser-Lys-Ala-Phe-NH2 (Chiba et al., 1989). SEQ: ID. NO.:43.

The CGRP 27-37 is a segment of human CGRP 1-37, which sequence is Tyr-Val-Pro-Thr-Ala-Val-Gly-Pro-Phe-Ala-Phe-NH2 (Rist et al., 1999). SEQ. ID. NO.:44.

These three peptides are our starting point. We modified the C-terminal region of CGRP (Rist et al., 1999) by synthesizing a series of undeca- and dodeca-peptides containing the C-terminal region of CGRP but with several modifications. The representative synthesis of AFA-CGRP receptor antagonist peptides 3 (AFA-peptide 3, also coded as MP 3) was illustrated in FIG. 1A. In brief, 4-(2',4'-dimethoxyphenyl-Fmoc-aminomethyl)phenoxy resin was used as the starting material to provide the C-terminus peptides capping with amino ($NH_2$) function. Removal of the Fmoc protecting group of the resin with piperidine in DMF provided resin 1 (step 1), which was used immediately by the coupling of Fmoc-Phe, O-(benzotriazol-1-yl)-N,N,N',N'-tetramethyluronium hexafluorophosphate (HBTU), and diisopropylethylamine (step 2) using a microwave peptide synthesizer. The resulting phenylalanine attached resin 2 was treated similarly as that described in steps 1 and 2 but altering the amino acid residues as that described in the peptide sequence AFA-peptide 3 (MP-3). The peptide was cleaved from the resin using thioanisole and thiocresol in TFA to give AFA-peptide 3. Similarly other four AFA-peptides, MP-1, MP-2, MP-4, and MP-5 were synthesized (FIG. 1B).

Figure 1B:
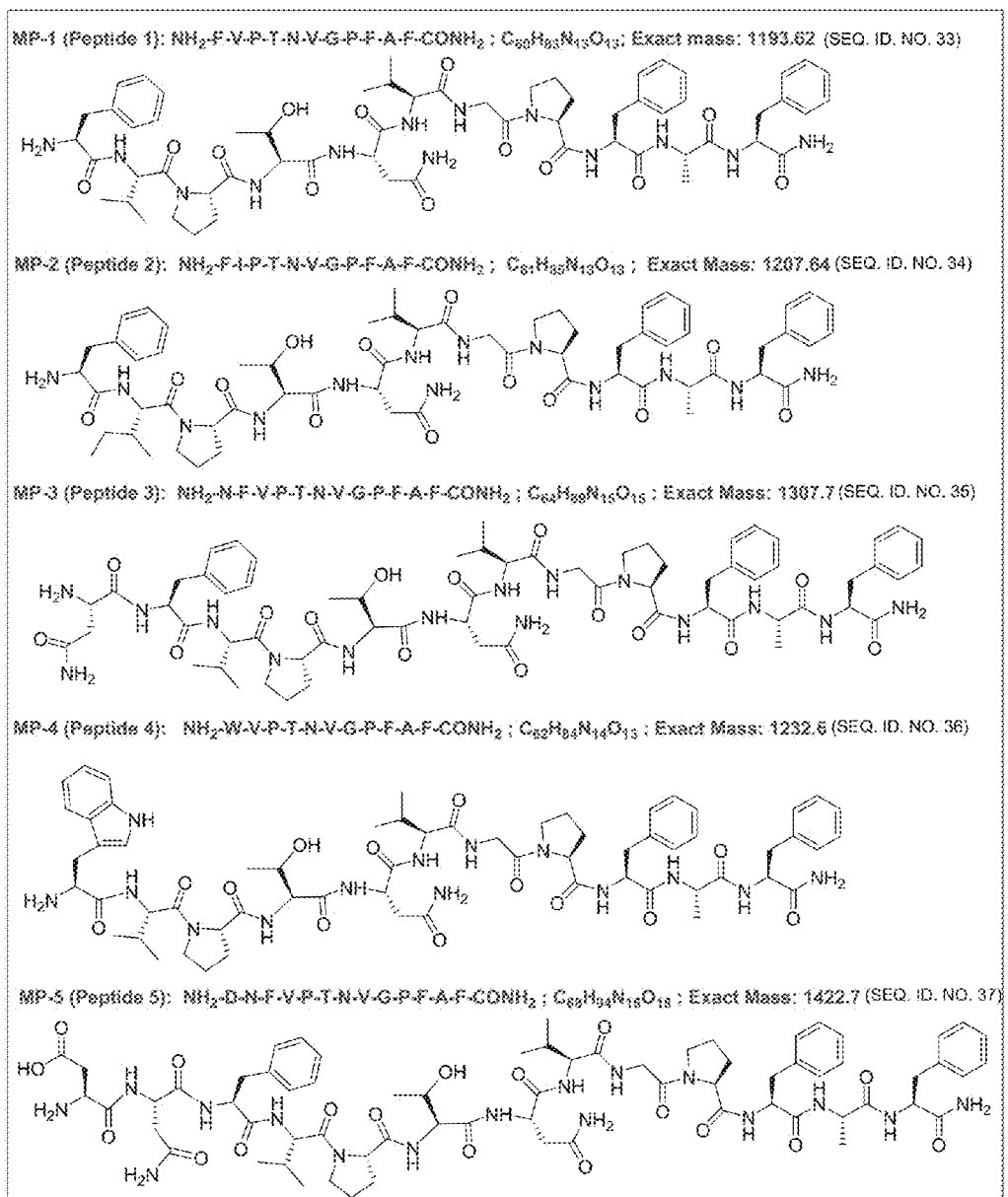

FIG. 1A showing representative synthesis of AFA-CGRP receptor antagonist peptides 3 (AFA-peptide 3, MP 3). Similarly other four new AFA-peptides, MP-1, MP-2, MP-4, and MP-5 were synthesized and are shown in FIG. 1B. The sequences of the five representative AFA-peptides are:

```
(1) AFA-Peptide 1 (MP-1):
                              (SEQ. ID. NO. 33)
NH2-F-V-P-T-N-V-G-P-F-A-F-CONH2.

(2) AFA-Peptide 2 (MP-2):
                              (SEQ. ID. NO. 34)
NH2-F-I-P-T-N-V-G-P-F-A-F-CONH2.

(3) AFA-Peptide 3 (MP-3):
                              (SEQ. ID. NO. 35)
NH2-N-F-V-P-T-N-V-G-P-F-A-F-CONH2.

(4) AFA-Peptide 4 (MP-4):
                              (SEQ. NO. ID. 36)
NH2-W-V-P-T-N-V-G-P-F-A-F-CONH2.

(5) AFA-Peptide 5 (MP-5):
                              (SEQ. NO. 37)
NH2-D-N-F-V-P-T-N-V-G-P-F-A-F-CONH2.
```

The linear amide peptides were synthesized using a CEM microwave peptide synthesizer (CEM Inc., Matthews, N.C.) starting from 4-(2',4'-dimethoxyphenyl-Fmoc-aminomethyl)-phenoxy resin by a sequence of reactions: (1) removal of the Fmoc protecting group with 20% piperidine in DMF; (2) coupling with Fmoc-amino acid, HBTU, and diisopropylethylamine (DIEA) in DMF (ninhydrin reagent was used to verify that the amino group was reacted, if not the same treatment of Fmoc amino acid, HBTU and DIEA was repeat); (3) removal of the Fmoc (by treating the resin with 20% piperidine in DMF twice to ensure that the Fmoc group is removed; the formations of by-products, 9-methylenefluorene and 9-(N-piperidylmethyl)fluorine were measured using mass spectrometry) and coupling of the subsequent amino acids in the sequence using the same reagents and procedure as described above; and (4) the C-terminus amino capped peptide was cleaved with a solution of 5% thioanisole and 5% thiocresol in 90% trifluoroacetic acid (TFA), and irradiated under a microwave reactor (20 W, 38° C.) for 40 min.

Synthesis of $NH_2$-Asn-Phe-Val-Pro-Thr-Asn-Val-Gly-Pro-Phe-Ala-Phe-$CONH_2$. (SEQ. ID. NO. 35).

A solution of 1.0 g (0.52 mmol) of 4-(2',4'-dimethoxyphenyl-Fmoc-aminomethyl)-phenoxy resin in 20% piperidine and DMF (20 mL) was subjected to the microwave irradiation (50 W, 15 min, 75° C.). The reaction mixture was filtered and washed with DMF (10 ml each, 5 times). The standard procedure for coupling of amino acids is followed. A solution of Fmoc-Phe-OH (1.56 mmol, 3 equiv.) and HBTU (1.40 mmol, 2.7 equiv.) in dry DMF (13 mL) containing 4.2% DIEA was added to the resin. The mixture was subjected to the microwave irradiation (25 W, 20 min, 75° C.) with stirring. The reaction mixture was filtered and washed with DMF (10 mL each, 5 times). Similar deprotection of Fmoc and coupling with Fmoc-amino acid were repeated until the desired sequence is obtained. The standard procedure for cleavage of the peptide from resin is followed. The above resin was washed with dichloromethane (20 mL) and mixed with 15 mL of a cleavage cocktail solution consists of 5% thioanisole and 5% thiocresol in 90% trifluoroacetic acid (TFA). The mixture was irradiated under a microwave reactor (20 W, 38° C.) for 40 min. The reaction mixture was filtered into a 100 mL flask and diluted with 100 mL of cold diethyl ether to precipitate out the desired peptide. The solid peptide was collected by centrifugation (2,500 rpm) and washed three times with cold diethyl ether to give a white solid (0.25 g; 41% yield). It was subjected to a HPLC using a preparative column (Phenomenex-Jupiter C18) and eluting with a gradient mixture of 40% methanol/water to 100% methanol over 40 min with a 10 ml/min flow rate. The fractions containing the desired product were combined and lyophilized to yield (SEQ. ID. NO. 35) $NH_2$—Asn-Phe-Val-Pro-Thr-Asn-Val-Gly-Pro-Phe-Ala-Phe-$CONH_2$ as a white solid.

Syntheses of (SEQ. ID. NO. 33) $NH_2$-F-V-P-T-N-V-G-P-F-A-F-$CONH_2$ (MP-1), (SEQ. ID. NO. 34) $NH_2$-F-I-P-T-N-V-G-P-F-A-F-$CONH_2$ (MP-2), (SEQ. ID. NO. 36) $NH_2$-W-V-P-T-N-V-G-P-F-A-F-$CONH_2$ (MP-4), and (SEQ. ID. NO. 37) $NH_2$-D-N-F-V-P-T-N-V-G-P-F-A-F-$CONH_2$ (MP-5).

(SEQ. ID. NO. 33) $NH_2$-F-V-P-T-N-V-G-P-F-A-F-$CONH_2$ (MP-1), (SEQ. ID. NO. 34) $NH_2$-F-I-P-T-N-V-G-P-F-A-F-$CONH_2$ (MP-2), (SEQ. ID. NO. 36) $NH_2$-W-V-P-T-N-V-G-P-F-A-F-$CONH_2$ (MP-4), and (SEQ. ID. NO. 37) $NH_2$-D-N-F-V-P-T-N-V-G-P-F-A-F-$CONH_2$ (MP-5) were synthesized similarly using a synthetic method similar to the aforementioned procedure of MP-3. Hence, from 1.0 g (0.52 mmol) of the 4-(2',4'-dimethoxyphenyl-fmoc-aminomethyl)-phenoxy resin, 13 mg of (SEQ. ID. NO. 33) $NH_2$-F-V-P-T-N-V-G-P-F-A-F-$CONH_2$ (MP-1) as a white solid was obtained after HPLC purification. From 0.7 g (0.364 mmol) of the 4-(2',4'-dimethoxyphenyl-fmoc-aminomethyl)-phenoxy resin, 36 mg of (SEQ. ID. NO. 34) $NH_2$-F-I-P-T-N-V-G-P-F-A-F-$CONH_2$ (MP-2) was obtained as a white solid. From 0.7 g (0.364 mmol) of the 4-(2',4'-dimethoxyphenyl-fmoc-aminomethyl)-phenoxy resin, 13 mg of (SEQ. ID. NO. 36) $NH_2$—W-V-P-T-N-V-G-P-F-A-F-$CONH_2$ (MP-4) was obtained as a white solid. From 1.0 g (0.7 mmol) of the 4-(2',4'-dimethoxyphenyl-fmoc-aminomethyl)-phenoxy resin, 16 mg of (SEQ. ID. NO. 37) $NH_2$-D-N-F-V-P-T-N-V-G-P-F-A-F-$CONH_2$ (MP-5) was obtained as a white solid.

Figure 2A:
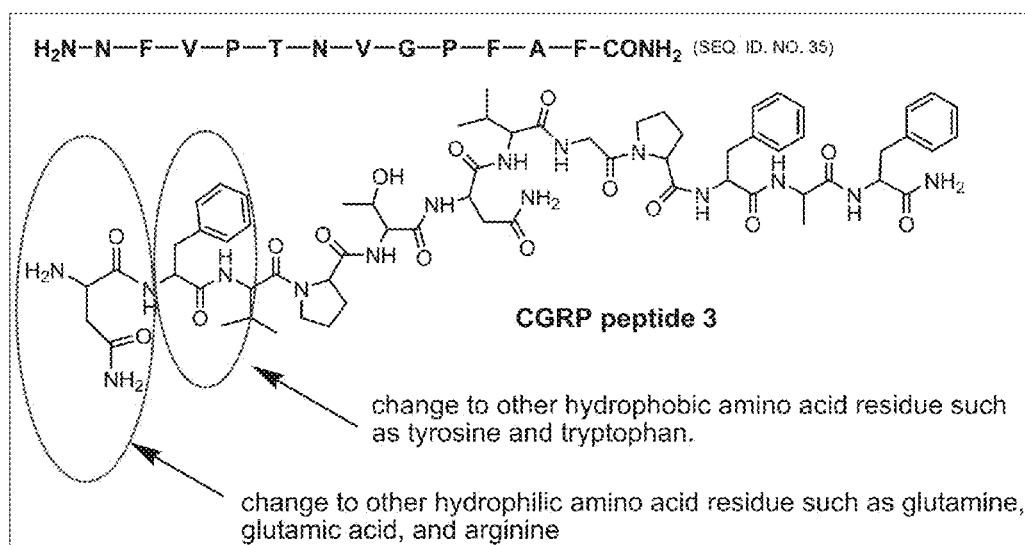
FIG. 2A. The representative substitutions of AFA-peptide 3 and, FIG. 2B and FIG. 2C five samples of synthesized AFA-peptide 3 analogs (AFA-peptide 6, 7, 8, 9 and 10).
Figure 2B:
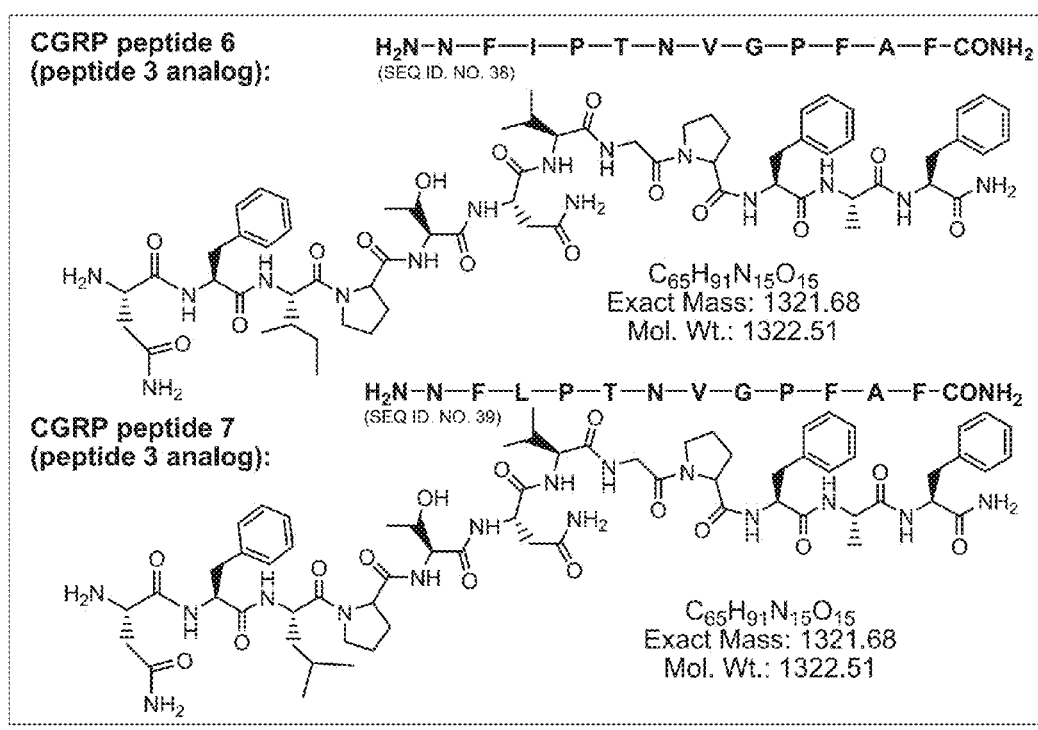
Figure 2C:
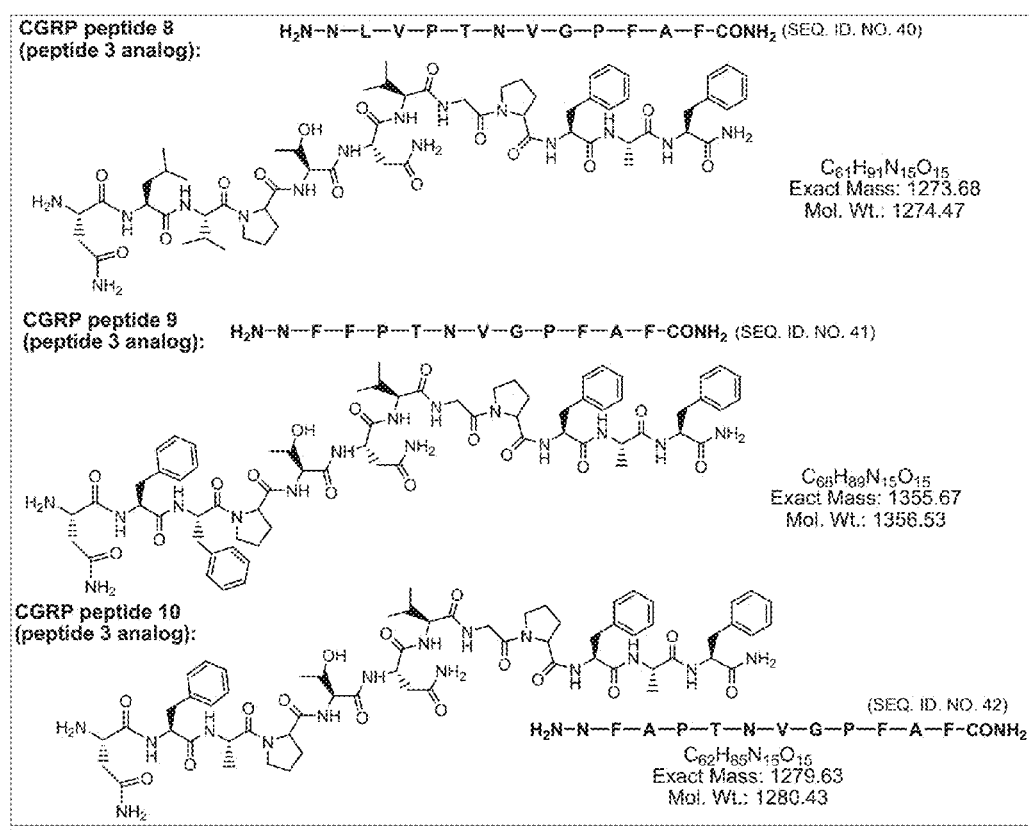

Since the Peptide-3 was found the most potent in binding assay and in vivo analgesic test (see below), a series of analogs of Peptide-3, peptide-6 to peptide-10, were further synthesized. Modifications of MP-3 were made by changing the amino acid residues 11 and 12 to other hydrophobic and hydrophilic amino acid, respectively, as illustrated in FIG. 2A. Residues 11 can be changed to tyrosine and tryptophan containing aromatic function as that of phenylalanine. Residue 12 can be modified by the replacement with glutamine, glutamic acid and arginine containing hydrophilic side chains. All peptides were purified by HPLC and characterized by mass spectrometry. Embodiment of the present invention is exemplified in five representative analogs of Peptide 3 (FIG. 2B) and their sequences are:

```
AFA-Peptide 6 (MP-6):
                              (SEQ. ID. NO. 38)
NH2-N-F-I-P-T-N-V-G-P-F-A-F-CONH2.

AFA-Peptide 7 (MP-7):
                              (SEQ. ID. NO. 39)
NH2-N-F-L-P-T-N-V-G-P-F-A-F-CONH2.

AFA-Peptide 8 (MP-8):
                              (SEQ. ID. NO. 40)
NH2-N-L-V-P-T-N-V-G-P-F-A-F-CONH2.

AFA-Peptide 9 (MP-9):
                              (SEQ. ID. NO. 41)
NH2-N-F-F-P-T-N-V-G-P-F-A-F-CONH2.

AFA-Peptide 10 (MP-10):.
                              (SEQ. ID. NO. 42)
NH2-N-F-A-P-T-N-V-G-P-F-A-F-CONH2.
```

Example 2. Binding Assay

Native Receptor Binding Assay:

The binding of $^{125}$I-CGRP to receptors in SK-N-MC cell membranes is carried out essentially as described (Edvinsson et al. (2001) *Eur. J. Pharmacol.* 415, 39-44). Briefly, membranes (25 µg) were incubated in 1 mL of binding buffer [10 mM HEPES, pH 7.4, 5 mM $MgCl_2$ and 0.2% bovine serum albumin (BSA)] containing 10 pM. $^{125}$I-CGRP and antagonist. After incubation at room temperature for 3 h, the assay is terminated by filtration through GFB glass fiber filter plates (PerkinElmer) blocked with 0.5% polyethyleneimine for 3 h. The filters are washed three times with ice-cold assay buffer (10 mM HEPES, pH 7.4 and 5 mM $MgCl_2$), then the plates are air dried. Scintillation fluid (50 µL) is added and the radioactivity is counted on a Topcount (Packard Instrument). Data analysis is carried out by using Prism and the K, is determined by using the Cheng-Prusoff equation (Cheng & Prusoff (1973) *Biochem. Pharmacol.* 22, 3099-3108).

Recombinant Receptor:

Human Calcitonin-like (CL) receptor (Genbank accession number L76380) is subcloned into the expression vector pIREShyg2 (BD Biosciences Clontech) as a 5'NheI and 3' PmeI fragment. Human RAMP1 (Genbank accession number AJ001014) is subcloned into the expression vector pIRESpuro2 (BD Biosciences Clontech) as a 5'NheI and 3'NotI fragment. HEK 293 cells (human embryonic kidney cells; ATCC #CRL-1573) are cultured in DMEM with 4.5 g/L glucose, 1 mM sodium pyruvate and 2 mM glutamine supplemented with 10% fetal bovine serum (FBS), 100 units/mL penicillin and 100 µg/mL streptomycin, and maintained at 37° C. and 95% humidity. Cells are subcultured by treatment with 0.25% trypsin with 0.1% EDTA in HBSS. Stable cell line generation is accomplished by co-transfecting 10 µg of DNA with 30 µg Lipofectamine 2000 (Invitrogen) in 75 $cm^2$ flasks. CL receptor and RAMP1 expression constructs are co-transfected in the cells in equal amounts. Twenty-four hours after transfection the cells are diluted and selective medium (growth medium+300 µg/mL hygromycin and 1 µg/mL puromycin) is added the following day. A clonal cell line is generated by single cell deposition utilizing a FACS Vantage SE (Becton Dickinson). Growth medium is adjusted to 150 µg/mL hygromycin and 0.5 µg/mL puromycin for cell propagation.

Recombinant Receptor Binding Assay:

Cells expressing recombinant human CL receptor/RAMP1 are washed with PBS and harvested in harvest buffer containing 50 mM HEPES, 1 mM EDTA and Complete® protease inhibitors (Roche). The cell suspension is disrupted with a laboratory homogenizer and centrifuged at 48,000 g to isolate membranes. The pellets are resuspended in harvest buffer plus 250 mM sucrose and stored at −70° C. For binding assays, 20 µg of membranes are incubated in 1 mL binding buffer (10 mM HEPES, pH 7.4, 5 mM $MgCl_2$, and 0.2% BSA) for 3 h at room temperature containing 10 µM $^{125}$I-hCGRP (GE Healthcare) and antagonist. The assay is terminated by filtration through 96-well GFB glass fiber filter plates (PerkinElmer) blocked with 0.05% polyethyleneimine. The filters are washed 3 times with ice-cold assay buffer (10 mM HEPES, pH 7.4, and 5 mM $MgCl_2$). Scintillation fluid was added and the plates were counted on a Topcount (Packard). Non-specific binding was determined and the data analysis was carried out with the apparent dissociation constant (K) determined by using a non-linear least squares fitting the bound CPM data to the equation below:

Recombinant Receptor Functional Assay:

Cells are resuspended in DMEM/F12 (Hyclone) supplemented with 1 g/L BSA and 300 µM isobutyl-methylxanthine. Cells are then plated in a 384-well plate (Proxiplate Plus 384; 509052761; Perkin-Elmer) at a density of 2,000 cells/well and incubated with antagonist for 30 min at 37° C. Human alpha-CGRP is then added to the cells at a final concentration of 1.2 nM and incubated an additional 20 min at 37° C. Following agonist stimulation, the cells were processed for cAMP determination using the two-step procedure according to the manufacturer's recommended protocol (HTRF cAMP dynamic 2 assay kit; 62AM4PEC; Cisbio). Raw data were transformed into concentration of cAMP using a standard curve then dose response curves were plotted and inflection point (IP) values were determined.

Both human calcitonin CGRP1 (CGRP1) membrane and [125I]-CGRP were purchased from Perkin Elmer (Waltham, Mass.). CGRP1 membrane was homogenized in the assay buffer (50 mM Tris-HCl pH 7.4, 5 mM $MgCl_2$, 0.5% BSA, 0.05% Tween20). The CGRP1 membranes were incubated with the test compounds in the presence of 0.24 nM of [125I]-CGRP. After 1 h of incubation, at room temperature, samples were filtered, using a Tomtec cell harvester, through glass fiber filters that had been presoaked in 0.05% polyethyleneimine and washed with the cold Tris buffer (50 mM Tris-HCl pH7.4). Filters were counted on a betaplate reader (Wallac). Nonspecific binding was determined by using 1 µM of rat CGRP peptide. IC50 values and hillslope values were determined by using the program Graphpad/PRISM. ki values were calculated using the Cheng Prusoff transformation (Cheng, et al., 1973): ki=IC50/(1+L/kd) where, L is radioligand concentration and kd is the binding affinity of the radiolig and, as determined previously by saturation analysis. Table 1 shows the binding affinity of CGRP and representative CGRP antagonist peptides on CGRP receptors. The novel AFA-peptides 3, 7, 9, and 10 have higher affinities than conventional CGRP 27-37 and CGRP 8-37.

TABLE 1

Binding affinity of CGRP and representative CGRP antagonist peptides on CGRP receptors

| Compound | Hill slope | Ki (nM) |
|---|---|---|
| CGRP | 0.80 ± 0.07 | 8.9 ± 1.0 |
| CGRP 27-37 | 1.62 ± 0.25 | 697.4 ± 51.0 |
| CGRP 8-37 | 1.21 ± 0.20 | 59.8 ± 0.4 |
| AFA-peptide 3 | 1.20 ± 0.02 | 33.3 ± 0.4 |
| AFA- peptide 6 | 1.13 ± 0.13 | 63.7 ± 11.8 |
| AFA- peptide 7 | 1.03 ± 0.15 | 54.8 ± 17.2 |
| AFA- peptide 8 | 0.88 ± 0.18 | 315.3 ± 77.8 |
| AFA- peptide 9 | 1.07 ± 0.05 | 49.6 ± 11.2 |
| AFA- peptide 10 | 1.07 ± 0.01 | 33.4 ± 4.1 |

Experiments were performed in duplicate or triplicate and repeated twice. Data are presented as Mean±SD.

Example 3. Pharmacological Evaluations

Embodiment studies were utilized to examine whether peripheral antagonism of CGRP receptors with CGRP 8-37 or an active AFA-peptide could attenuate acute and chronic pain caused by a variety of disorders. Transdermal or cutaneous analgesia produced by CGRP 8-37, an AFA-peptide, or a combination of a therapeutic, including, but not limited to lidocaine, saxitoxin, dexamethasone, ibuprofen, and via a selected delivery method as appropriate for a specific pain model and test, were detailed in specific examples. All studies were performed in male rats (Sprague-Dawley, 200-280 g, Harlan), and each experimental group had n=6-8 rats. All drug solutions were freshly prepared in the vehicle containing 0.5% hydroxyl propyl cellulose and 2% DMSO, unless specified otherwise.

Embodiments contemplated are therapeutic methods utilizing one or more of the therapeutic composition as described above. On such therapeutic method is a method for treating pain or an inflammatory condition in a patient in need of such treatment, which method comprises administering a therapeutically effective amount of the composition according to the invention by intradermal administration at the peripheral site of sensory nerve endings and their surrounding tissues. A preferred administration of, but not limited to using standard metal needles, microneedle patches, intranasal spray or topical application with known topical skin formulations (described above).

Example 4. Spared Nerve Injury-Induced Neuropathic Pain Model

The spared nerve injury (SNI), a mononeuropathic pain model (Decosterd and Woolf, 2000) was used to assess the anti-CGRP receptor antagonist peripheral effects in both thermal and mechanical pain thresholds. Of the three branches of the sciatic nerve the tibial and common peroneal nerves were cut and ligated leaving the sural nerve intact. Pre-surgery baselines (BL, 100%) of the thermal and mechanical pain thresholds of the ipsilateral hindpaws were measured using the Hargreaves thermal stimulator (6.0 A with a surface temperature of 30° C.; Hargreaves et al., 1988) and von Frey hair monofilaments (up-down method, Chaplan et al., 1994). One week post-surgery, the SNI rats experienced an around 50% reduction in thermal pain thresholds (paw withdrawal latencies reducing to 8 s from pre-injury~16 s), indicating hyperalgesia. The rats also exhibited extreme mechanical allodynia indicated by a 75-90% reduction in mechanical threshold compared to the baseline. These pain conditions lasted for 6-8 weeks, modeling chronic neuropathic pain. All drug testing was conducted with this post-SNI period.

Figure 3A:
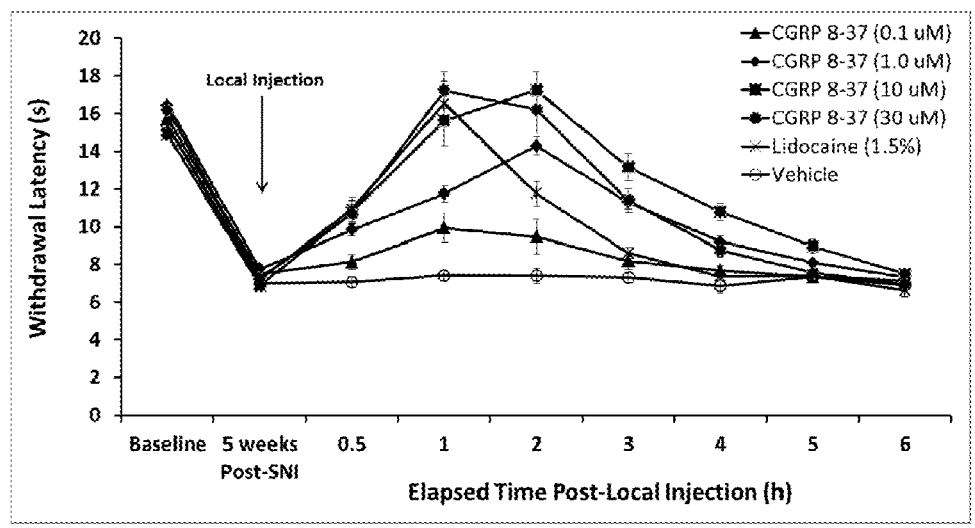
FIG. 3A and FIG. 3B. CGRP 8-37 via local intradermal injection reduces rat spared nerve injury (SNI)-induced neuropathic pain in a dose-related manner.
Figure 3B:
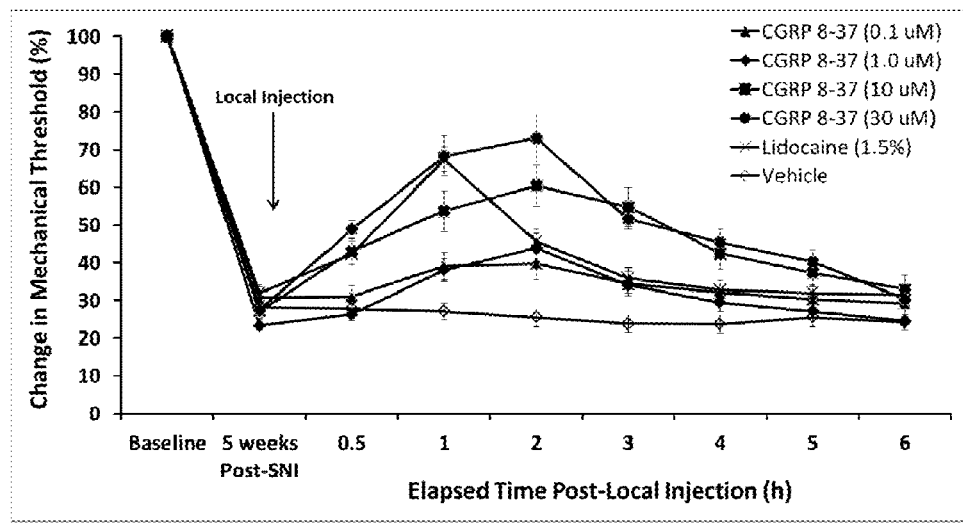

Anti-CGRP Peptides Transdermally Delivered by a Standard Needle Injection Reduce Rat Spared Nerve Injury-Induced Neuropathic Pain To first test whether a local peripheral application of an anti-CGRP receptor peptide can treat neuropathic pain in the SNI model, local intradermal injection of the conventional CGRP antagonist peptide CGRP 8-37 (0.1, 1, 10 and 30 µM, each 50 µL), lidocaine (1.5%, as positive control) or the vehicle (50 µL) was made in the left ipsilateral hindpaw (the SNI side) using a metal needle under a brief and light anesthesia condition (with 2.5% isoflurane). The rat recovered from anesthesia within a few minutes and the thermal and mechanical pain thresholds were determined at 0.5, 1, 2, 3, 4, 5 and 6 hour after the treatment using the methods described above. Local injection of CGRP 8-37 reduced SNI-induced neuropathic pain as indicated by both thermal and mechanical pain threshold measurements compared to the control group. CGRP 8-37 produced analgesic effects, particularly on hyperalgesia are in a dose-related manner. Lidocaine produced positive control while the vehicle as the negative control (FIG. 3A and FIG. 3B, p<0.05 vs vehicle, n=8 per group).

Figure 4A:
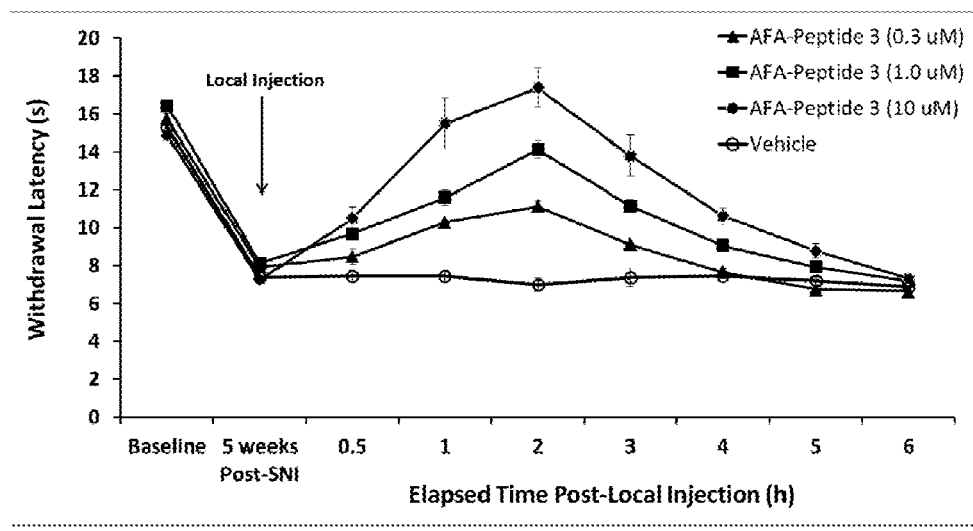
FIG. 4A and FIG. 4B. AFA-peptide 3 via local intradermal injection reduces rat spared nerve injury-induced neuropathic pain in a dose-related manner.
Figure 4B:
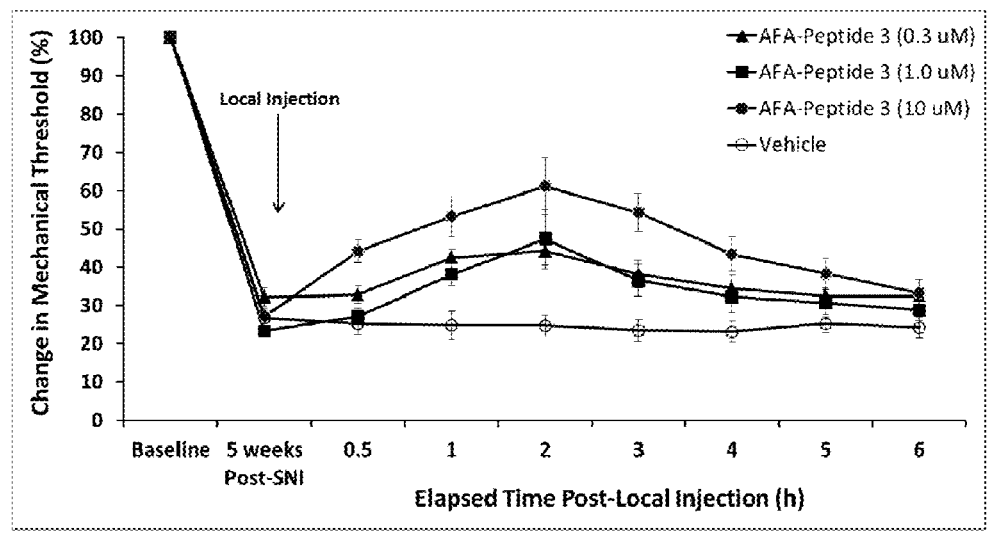

Using the same test protocol in a different cohort of SNI rats, novel AFA-peptide 3 (0.1, 1 and 3 µM, each 50 µL) or the vehicle (50 µL) was injected into the ipsilateral hindpaws under a brief and light anesthesia condition (with 2.5% isoflurane). The thermal and mechanical pain thresholds were determined at 0.5, 1, 2, 3, 4, 5 and 6 hour after the treatment. AFA-peptide 3 produced analgesic effects, particularly on thermal pain in a dose-related manner while in the vehicle group the neuropathic pain was persistent (FIG. 4A and FIG. 4B, p<0.05 vs vehicle, n=8 per group).

Figure 5A:
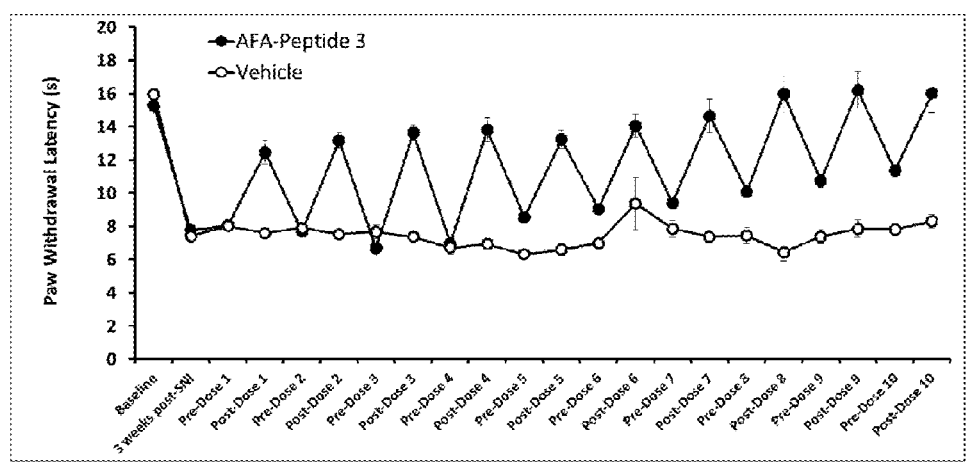
FIG. 5A and FIG. 5B. Repetitive local intradermal injections of AFA-peptide-3 produce consistent analgesia in rat spared nerve injury-induced neuropathic pain without development of tolerance.
Figure 5B:
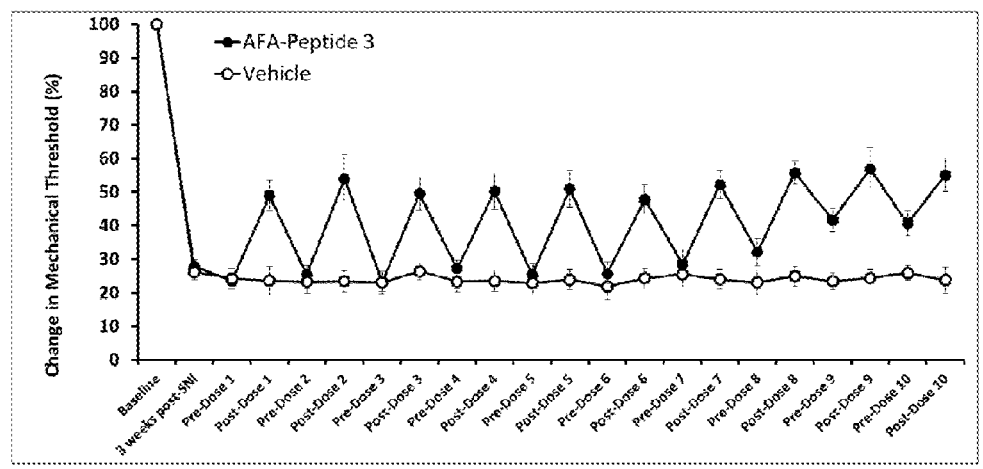

Furthermore, daily repeated injections of AFA-peptide 3 (1 µM, 50 µL) in the same cohort of SNI rats used for dose-response study above for consecutive 10 days, the peptide produced consistent analgesic effects (p<0.01 vs vehicle) and apparently did not cause tolerance, while the control vehicle group remained neuropathic pain state throughout the entire experiment (FIG. 5A and FIG. 5B, n=8 per group).

Anti-CGRP Peptide Delivered by Microneedles Reduces Spared Nerve Injury-Induced Neuropathic Pain Embodiments contemplated are therapeutic methods utilizing one or more of the therapeutic composition as described above. On such therapeutic method is a method for treating pain or an inflammatory condition in a patient in need of such treatment, which method comprises administering a therapeutically effective amount of the composition according to the invention by intradermal administration at the peripheral site of sensory nerve endings. Since a neuropathic pain condition often affects a wide area of the body. A preferred intradermal administration is wherein intradermal injection is made using a multiple microneedle patch incorporating CGRP 8-37 or an active AFA-peptide and even more preferred is such a method wherein the microneedle patch incorporates a therapeutic composition comprising an effective amount of both CGRP 8-37 or an active AFA-peptide and a sodium channel blocker.

Microneedles patches containing either vehicle as control (starch materials) or CGRP 8-37 (11.3 µg/patch, 44 needles/ patch, 750-1,500 µm needle length) were applied to the ipsilateral hindpaws (for 20 minutes) of lightly anesthetized (2.5% isoflurane) rats to determine whether microneedles delivery of a CGRP receptors receptor, such as CGRP 8-37 could attenuate the neuropathic pain. In this specific example, gabapentin, a clinical drug for the treatment of neuropathic pain (Sigma, 100 mg/kg, intraperitoneal injection, i.p.) was used a benchmarker. Thermal pain thresholds were tested one hour after the treatment.

Figure 6A:
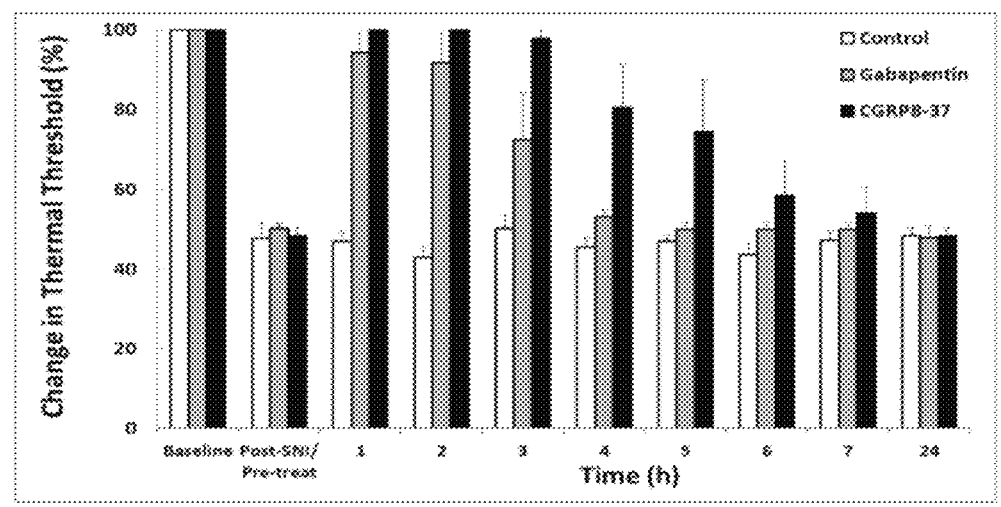
FIG. 6A and FIG. 6B. Local intradermal application of CGRP 8-37 via microneedle delivery reduces spared nerve injury (SNI)-induced neuropathic pain in rats.

Of the three treatments in the same cohort of animals, the paws that received CGRP 8-37 treatment exhibited a full reversal to baseline thermal threshold values around 1 hour post-microneedle application and lasted up to 5 hours (n=8, p<0.01). As expected, the control microneedles had no any observable analgesic effects. Gabapentin produced a significant antihyperalgesic effect that peaked at 1 hour post-i.p. injection but only lasted for 3 hours (FIG. 6A).

Figure 6B:
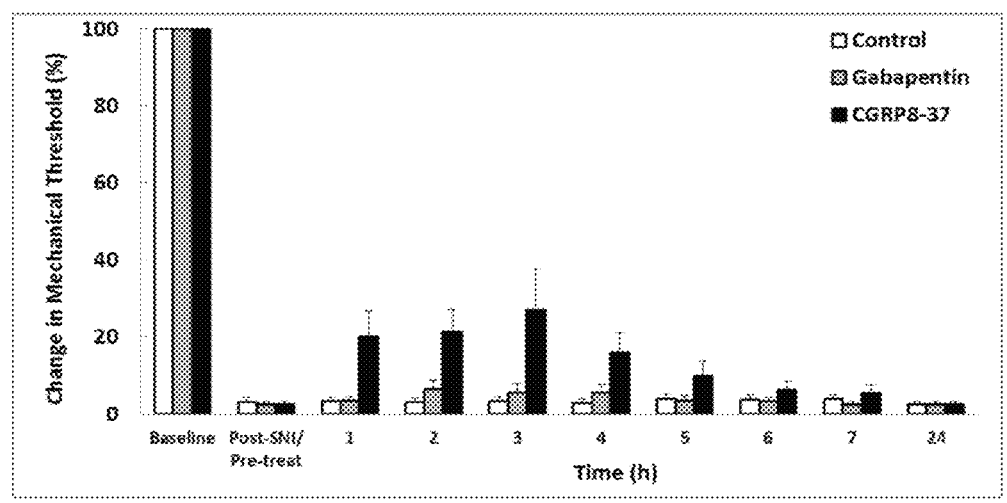
Figure 7A:
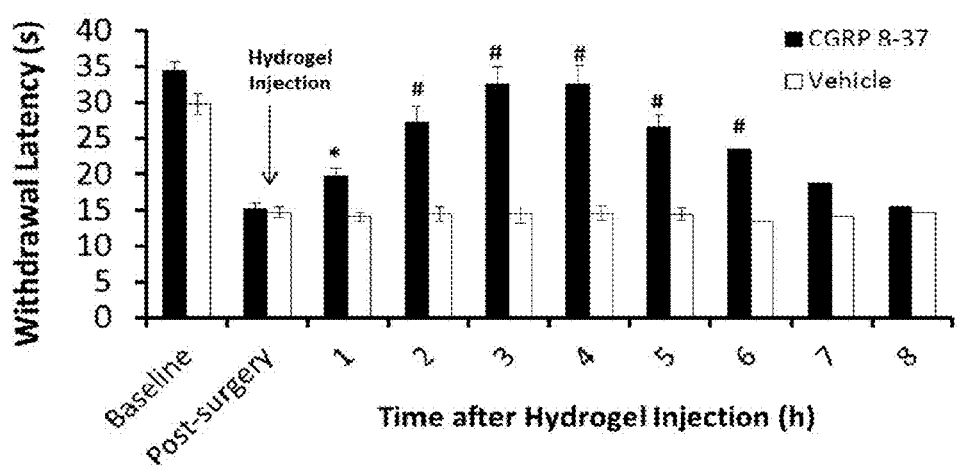
FIG. 7A and FIG. 7B. Local intradermal injection of CGRP 8-37 formulated in hydrogel (1 µM, 100 µL) to the nerve injury site reduces thermal (FIG. 7A) and mechanical pain (FIG. 7B) in the spared nerve injury model in rats.
Figure 7B:
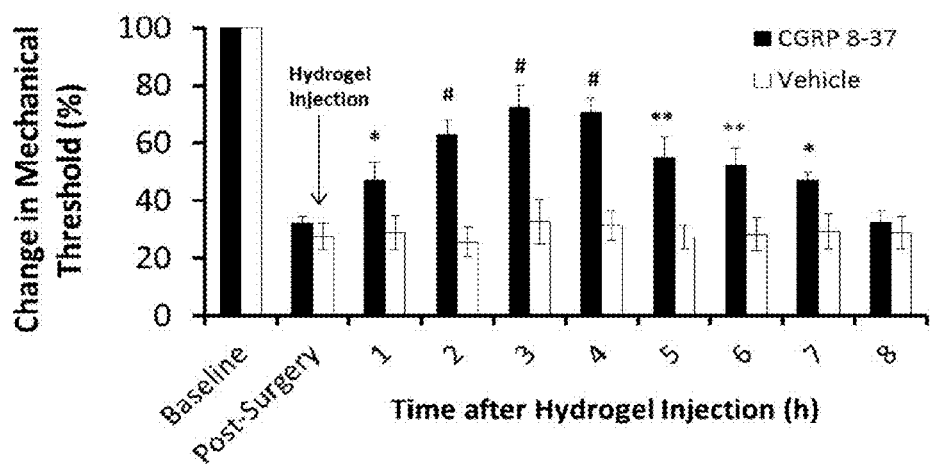

In the same cohort of rats, mechanical nociceptive thresholds were measured on the ipsilateral hindpaws using von Frey monofilaments. The rats were tested once every hour for the initial 1-7 hours and then 24 hours after microneedle application. Rats that received CGRP 8-37 microneedles exhibited a ~25% return toward baseline mechanical sensitivity. The observed anti-allodynic effect lasted for up to 6 hours, reaching a maximal effect at 3 hours post-microneedle application (FIG. 6B). As reported in Table 2 below and plotted in FIG. 6A and FIG. 6B, CGRP 8-37 microneedle patch treatment fully reverses thermal hyperalgesia and reduces mechanical allodynia in the rat SNI model. Thus, local peripheral application of CGRP 8-37 using microneedles delivery to transdermal tissue clearly alleviated chronic pain induced by injury to the peripheral nerve.

thermal and mechanical pain thresholds were then measured every 1 hour up to 8 hours post-injection. CGRP 8-37 hydrogel produced significant analgesic effects lasting up to 6 hours in thermal pain and 7 hours in mechanical pain post-injection (FIG. 7A and FIG. 7B).

Example 5. Tibial Neuroma-Induced Neuropathic Pain Model

CGRP in sensory neurons has been shown to be critical in the development and maintenance of neuropathic pain in rodent models (Maddula et al., 2012) and high concentrations of CGRP have been localized to experimental neuromas and appears to be released from those neuromas. Furthermore intrathecal injection of $CGRP_{8-37}$ was shown to reverse mechanical allodynia in rat neuropathic models (Zochodne et al., 1995). Thus, the novel AFA-peptide 3 was intradermally injected to the neurom site in the tibial neuroma transposition model and tested whether local anti-CGRP could be effective in relieving the neuroma-induced pain.

Figure 8A:
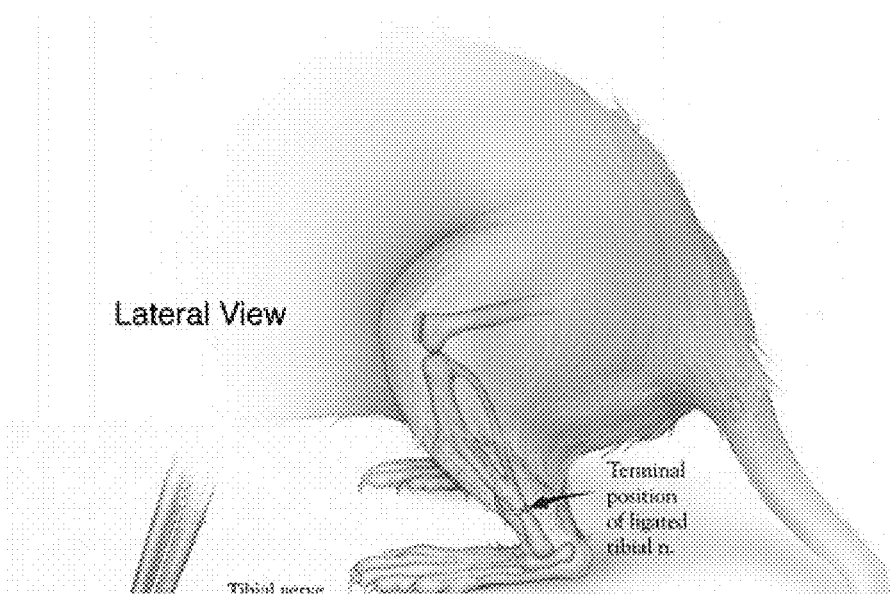
FIG. 8A and FIG. 8B. Local injection of AFA-peptide-3 reduces neuroma tenderness, an indicator of neuropathic pain responses.

Sprague Dawley rats (male, approximately 400 g) were undergone surgery as described by Dorsi et al., briefly, a 2-3 cm incision was made through the skin and subcutaneous fascia of the ventral surface of the pelvic leg extending from the tarsometatarsal joint to approximately 1 cm distal to the level of the stifle the nerve was isolated and the posterior tibial branch was ligated and then sharply transected approximately 2 mm distal to the ligature, as illustrated in FIG. 8A. After the medial skin incision closure, the rat was transferred to a recovery cage devoid of bedding and placed halfway upon a recirculating hot water pad until standing;

TABLE 2

| | | Post SNI Operation and Therapy Average Response Latency | | | | | | | |
|---|---|---|---|---|---|---|---|---|---|
| | BL/ Pre- SNI | Post-SNI/ Pre- treatment | Time post-treatment with CGRP 8-37 (hour) | | | | | | |
| | | | 1 | 2 | 3 | 4 | 5 | 6 | 7 | 24 |
| Mean (sec) | 100 | 48.4 | 100.3 | 102.3 | 97.8 | 80.5 | 74.4 | 58.4 | 54.0 | 48.4 |
| ±SEM (sec) | 0 | 1.97 | 6.22 | 7.20 | 7.98 | 11.04 | 13.04 | 8.83 | 6.71 | 1.97 |

BL: baseline;
SNI: spared nerve injury

Anti-CGRP Peptide in Hydrogel Delivered by Local Injection to Nerve Injury Site Reduces Neuropathic Pain In the same in another embodiment, the invention delivered anti-CGRP peptide formulated in hydrogel to achieve a sustained or slow release which can enhance the magnitude and prolong duration of the analgesic effect. Using the same SNI model in a different cohort of rats, an anti-CORP peptide formulated in hydrogel was directly injected to around the nerve injury site (instead of the ipsilateral hindpaws) and the analgesic effects were tested on the ipsilateral hindpaws using the thermal and mechanical pain thresholds measurements. CGRP 8-37 was first dissolved in phosphate buffer solution (pH 7.4) and then mixed in the water-soluble block copolymer of polyethylene oxides (PEO) and propylene oxides (PPO) (Sigma) to form CGRP 8-37 hydrogel. Local injection of a unit dose of CGRP 8-37 hydrogel (final concentration at 1 μM, 100 μL) to the nerve injury site, the once recovered, the rat was returned to its home cage and monitored daily for signs of pain and wound dehiscence.

Figure 8B:
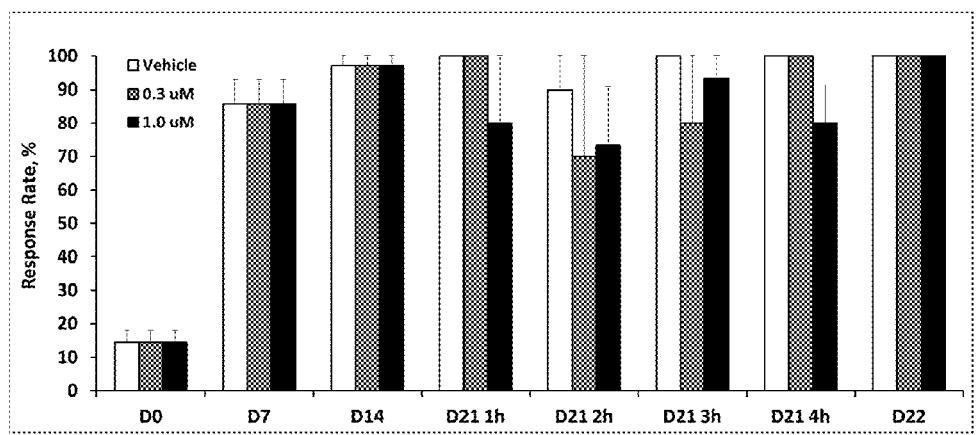

The rats were allowed to recover from the surgical procedure before beginning behavioral testing to assess neuroma development. On post-operative days 7 and 14, rats were were assessed for mechanical pain using the "up-down" method of Von Frey mechanical testing and direct mechanical stimulation of the neuroma (referred to as neuroma tenderness testing). Neuroma tenderness was tested by applying the 15 g filament to the neuroma site up to five times in a series with a three second break between applications; the series was completed and scored as a positive as soon as a positive withdrawal response is seen. Five repetitions of the series were performed three minutes apart. The neuroma tenderness was calculated as the number of positive series scored out of the five repetitions of series. Around postoperation day (POD) 22, AFA-Peptide-3 (0.3 μM, 50

µL) or 50 of vehicle were injected ("infiltrated") into the skin over the neuroma site, indicated by the characteristic nodule under skin surface. As shown in FIG. 8B, AFA-peptide 3 reduced neuroma tenderness in dose-related manner and the duration of analgesic lasted for 3-4 hours.

Example 6. Diabetes-Induced Neuropathic Pain Model

Anti-CGRP Peptide Delivered by Microneedles Reduces Diabetic Neuropathic Pain

Figure 9A:
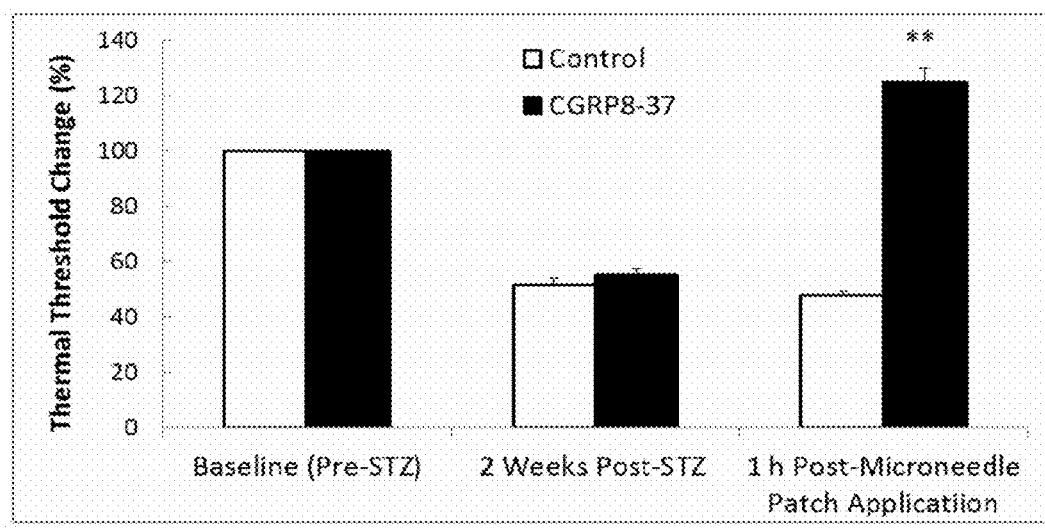
FIG. 9A and FIG. 9B. Local intradermal application of CGRP 8-37 via microneedle delivery reduces streptozotocin (STZ)-induced diabetic pain in rats.

Painful peripheral neuropathy is a common secondary complication of diabetes mellitus. Streptozotocin (STZ)-induced diabetic polyneuropathy causes more broad pain and has neurogenic inflammation component in rodents (Bishnoi et al., 2011). Prior to STZ administration, each rat's baseline of thermal and mechanical thresholds on their individual hindpaws were assessed using the Hargreaves thermal pain test, and von Frey mechanical pain test, respectively. In a naïve rat, the average paw withdrawal latency using the Hargreaves thermal stimulator was approximately 15 s. Once these baseline values were recorded, a dose of STZ (50 mg/kg, i.p.) was administered to each rat (n=6 per group). Two weeks post-STZ administration, the rats' average withdrawal latency dropped by 45% (withdrawal latency around 8.5 s, FIG. 9A). In addition, each rats' blood glucose levels were measured using a basic glucose level monitor and verified hyperglycemia status (baseline 115±17 mg/100 mL vs. post-STZ 405±25/100 mL), confirming that diabetic model was established.

Figure 9B:
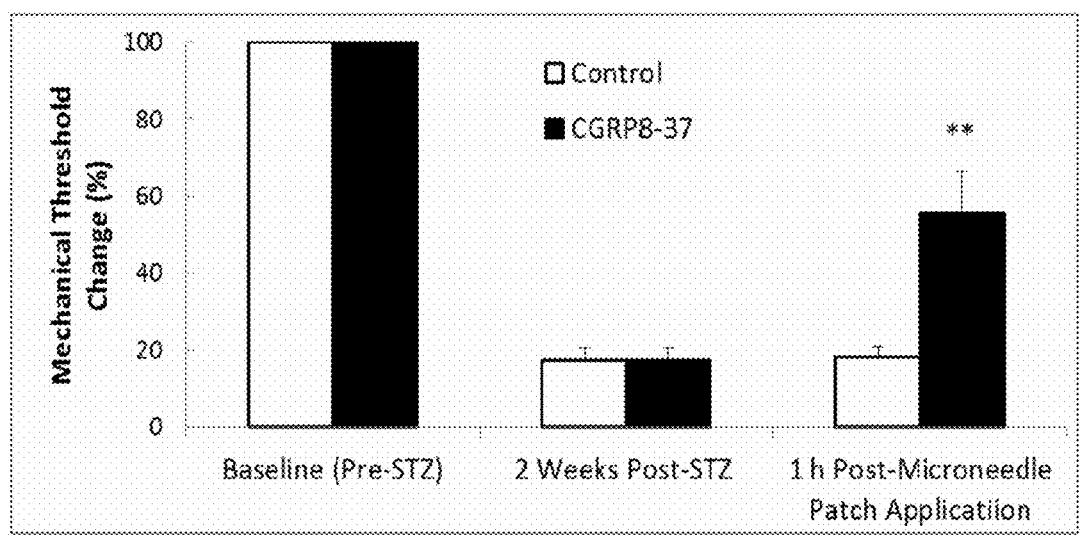

For the rats that displayed a decrease in thermal pain thresholds, analgesic treatments via microneedle patch delivery of CGRP 8-37 or ibuprofen as a positive control were evaluated in comparison with control patches. Microneedle patches containing CGRP 8-37 (44 needles/patch, 11.3 µg/patch, 1.5 mm needle length) were patched on the rat hind paw for 20 min. After removing the patches, hindpaw withdrawal latencies induced by continuous and noxious heat (Hargreaves) were assessed at 1 hour post-microneedle application. The paws that received CGRP 8-37 microneedles showed a full return to their baseline thermal thresholds (FIG. 9A); while exhibited a 35% return to their mechanical pain baseline values (showing an ability to withstand 55% of mechanical stimulation as they had prior to STZ injection). For the rats that received control microneedle patches, the hyperalgesia and allodynia persisted (FIG. 9B).

Example 7. Ultraviolet B Radiation-Induced Inflammatory Pain Model

Anti-CGRP Peptide Delivered by Microneedles Mitigates Radiation-Induced Inflammatory Pain in the Rat Cheek To further confirm the peripheral action of anti-CGRP in anti-inflammatory pain effects, a well-defined inflammatory pain model in rats was employed. Ultraviolet B (UVB) radiation causes cutaneous inflammation in humans and animals. One important clinical consequence of UVB-induced inflammation is causing hyperalgesia. Changes in thermal sensitivities in the area of primary UVB irradiation are well documented both in humans and in the animal models (Zhang et al., 2009). Maximal pH decrease, coupled with peak hyperalgesia, occurred 48 hours after UVB-irradiation is likely involved in CGRP released from peripheral sensory neuron terminals. This model provides an experimental model of post radiation pain and can mimic one type of burn pain. To determine the magnitude of anti-inflammatory pain effects for a given drug transdermally delivered by way of microneedle delivery, the depilated rat's cheeks were exposed to an inflammatory dosage of Ultraviolet B radiation (Zhang et al., 2009).

Figure 10:
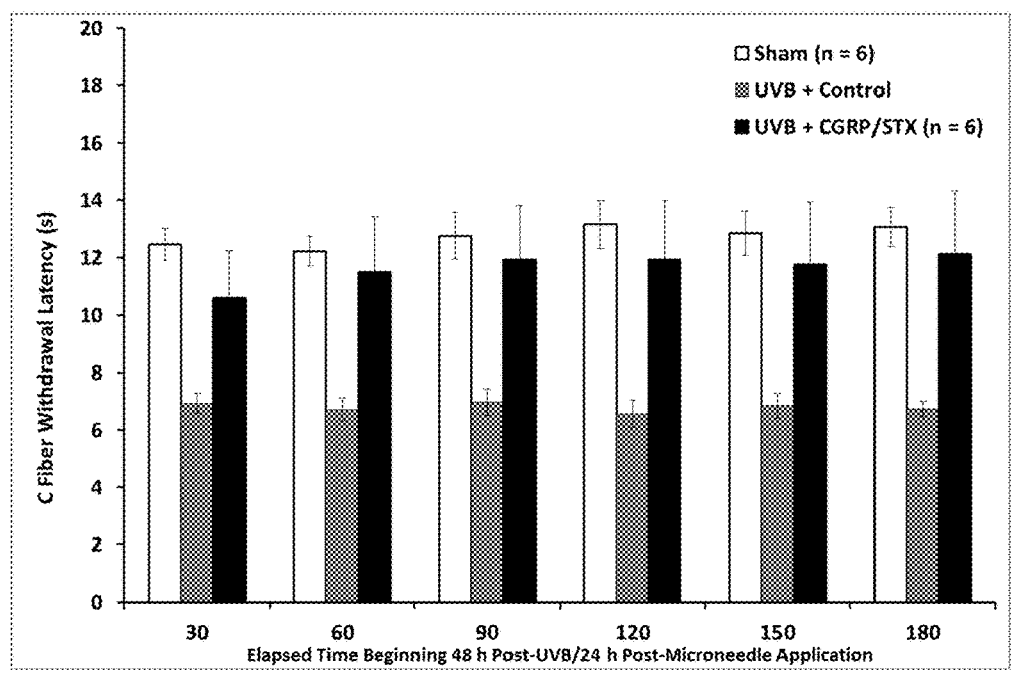
FIG. 10. Local intradermal application of a combination of CGRP 8-37 and saxitoxin (STX) via microneedle delivery normalizes C-fiber stimulation-evoked withdrawal latency to sham control in a UVB radiation-induced neurogenic inflammatory pain model in rats.

With the skin of a rat's cheek was stretched, the circular (8 mm in diameter) fiberglass applicator of the UV Curing Device (Dymax Bluewave 200) was applied to the center of the rat's cheek. To produce an appropriate inflammation, a total dose of 1200 mJ/cm$^2$ UVB was administered to one rat cheek for 25 seconds. The same procedure was performed on the rat's contralateral cheek. Upon completion of UVB irradiation, all rats were returned to their home cages and were assessed for thermal pain between 24-48 hours later. At this period, persistent UVB-inflammation could be induced. The rats were lightly anesthetized with urethane (800 mg/kg, IP) and heat-induced withdrawal latencies of the cheeks (an indicator of C fiber stimulation responses) were measured. Twenty-four hours post-UVB, rats exhibited hypersensitivity to thermal stimuli and cheek withdrawal latencies decreased from 12.5±0.7 s to 6.7±0.3 s (n=6) with control microneedle patches. A sham control group (n=6) were only completely depilated and cleansed with ethanol wipes but without UVB challenge. The cheek withdrawal latencies in the sham group were no significant changes throughout the entire experiment Microneedle patches containing CGRP 8-37 at 0.113 and 11.3 µg/patch (44 needles/patch, 1.5 mm needle length) were applied to UVB-radiated rats for 20 minutes. After removing patches, cheek withdrawal latencies induced by continuous and noxious heat were assessed at different time points from the end of the 20 minute treatment period up to 3 hours post treatment. Likewise, the same application process and test were carried out on the contralateral cheek with a control patch that had no drugs within the microneedles as negative control. Only at the higher dose CGRP 8-37 produced significant anti-thermal analgesic effects compared to negative control Patches (FIG. 10), while the lower dose caused an insignificant increase in the cheek withdrawal latency (data not shown).

As shown in Table 3, CGRP 8-37 produces potent anti-inflammatory thermal pain effect in rat cheeks with UVB-induced inflammation (24 h post-UVB stimulation, n=6).

TABLE 3

UVB Model

| Post patch removal (min) | Average Reduced Latency for Inflammation | | | |
|---|---|---|---|---|
| | Control | | CGRP 8-37 | |
| | Mean (sec) | SEM (±sec) | Mean (sec) | SEM (±sec) |
| 0 | 6.5 | 0.9 | 8.0 | 0.5 |
| 15 | 7.2 | 0.7 | 9.1 | 0.6 |
| 30 | 7.8 | 0.4 | 9.9 | 0.6 |
| 45 | 7.4 | 1.0 | 10.5 | 1.5 |
| 60 | 7.8 | 0.5 | 11.2 | 1.0 |
| 90 | 8.6 | 0.6 | 11.0 | 0.5 |
| 120 | 7.2 | 0.2 | 11.2 | 0.8 |
| 150 | 8.0 | 0.5 | 11.0 | 0.4 |
| 180 | 8.6 | 0.4 | 12.2 | 1.0 |

To compare the anti-CGRP effects with sodium channel blockade effects, the most potent sodium channel blocker, saxitoxin was fabricated in microneedles (3.2 µg/patch, 44 needles/patch, 1.5 mm needle length) and applied to the same UVB-induced inflammation pain model in rats (n=6). The patches were applied on the rat cheek for 20 minutes.

After removing the patches, cheek withdrawal latencies induced by continuous and noxious heat were assessed at different time points up to 3 hours as described above. As shown in Table 4, Saxitoxin treated rats exhibited a produced gradual onset of an anti-inflammatory effect in rat cheeks having UVB-induced inflammation (24-h post-UVB stimulation, n=6).

TABLE 4

| UVB Model Average Cheek Withdrawal Latency | | | | | | |
|---|---|---|---|---|---|---|
| | Sham | | UVB + Control | | UVB + Saxitoxin | |
| | Mean (sec) | SEM (±sec) | Mean (sec) | SEM (±sec) | Mean (sec) | SEM (±sec) |
| 24 hours Post-UVB Baseline Post patch removal (min) | 12.4 | 0.6 | 6.6 | 0.6 | 6.3 | 1.0 |
| 15 | 12.6 | 0.5 | 6.4 | 0.4 | 7.1 | 0.6 |
| 30 | 12.4 | 0.4 | 6.3 | 0.5 | 7.9 | 0.3 |
| 45 | 13.0 | 0.4 | 6.9 | 0.8 | 8.3 | 0.5 |
| 60 | 13.0 | 0.6 | 6.6 | 0.6 | 8.5 | 0.5 |
| 90 | 12.8 | 0.6 | 6.9 | 0.8 | 9.1 | 0.8 |
| 120 | 12.5 | 0.4 | 6.0 | 0.8 | 9.0 | 0.8 |
| 150 | 11.9 | 0.6 | 6.0 | 0.5 | 8.9 | 0.9 |
| 180 | 11.4 | 0.8 | 6.4 | 0.5 | 9.7 | 1.4 |

In an exemplary therapeutic method, the intradermal injection is made using a microneedle patch incorporating a combination of CGRP 8-37 or an active AFA-peptide with a sodium channel blocker that may be in admixture with one another in a therapeutic composition or may be each located within distinct portions of the microneedle therapeutic dose patch. The sodium channel blocker may be selected from a lidocaine or saxitoxin derivative.

Table 5 reports data for combination treatment therapeutics compared to single compound and control treatments. Microneedle patches (44 needles/patch, 1.5 mm needle length) containing a combination of CGRP 8-37 (7.8 μg/patch,) and saxitoxin (1.6 μg/patch) were patched on each rat cheek for 20 minutes. After removing the patches, cheek withdrawal latencies induced by continuous and noxious heat were assessed at different time points up to 3 hours. The combination of CGRP 8-37 (7.8 μg/patch,) and saxitoxin (1.6 μg/patch) in patches produced more potent anti-inflammatory and thermal analgesic effect in rat cheeks with the UVB-induced inflammation (24 h post-UVB stimulation, n=6) conditions, compared with either of the individual compounds or the control (compare results shown in Tables 3 and 4).

TABLE 5

| UVB Model | | | | |
|---|---|---|---|---|
| | Reduced Latency for Combination Therapeutics | | | |
| Post patch | Control | | CGRP 8-37 + Saxitoxin | |
| removal (min) | Mean (sec) | SEM (±sec) | Mean (sec) | SEM (±sec) |
| 0 | 7.5 | 0.8 | 9.3 | 2.0 |
| 10 | 7.3 | 1.3 | 9.1 | 1.6 |
| 20 | 7.3 | 0.7 | 7.6 | 0.6 |
| 30 | 7.2 | 0.9 | 8.6 | 0.6 |
| 60 | 6.2 | 0.5 | 9.3 | 1.7 |
| 90 | 5.6 | 0.6 | 11.6 | 1.6 |
| 120 | 5.6 | 0.6 | 11.1 | 1.3 |

TABLE 5-continued

| UVB Model | | | | |
|---|---|---|---|---|
| | Reduced Latency for Combination Therapeutics | | | |
| Post patch | Control | | CGRP 8-37 + Saxitoxin | |
| removal (min) | Mean (sec) | SEM (±sec) | Mean (sec) | SEM (±sec) |
| 150 | 5.7 | 0.4 | 13.3 | 1.0 |
| 180 | 5.5 | 0.4 | 13.0 | 0.9 |

Table 6, reports data showing that the effect of CGRP 8-37+saxitoxin is still evident even after as long as more than 47 hours post dosing, which are unexpected results. The UVB-induced inflammation condition will last up to 48-72 hours in rats and the therapeutic effects observed with treating anti-inflammatory pain by the combination of CGRP 8-37 and saxitoxin were assessed only up to 27-hour post-UVB without reaching plateau. Accordingly, anti-inflammatory effects were examined 48 hours post-UVB and after the application of the patch. Twelve rats were subjected to UVB radiation (1200 mJ/cm$^2$). Immediately thereafter, each rat was randomly assigned to receive a microneedle patch (44 needles/patch, 1.5 mm needle length) containing a combination therapeutic composition of CGRP 8-37 (7.8 μg/patch,) and saxitoxin (1.6 μg/patch) or a control patch. The patch was placed over the inflamed area for a period of 20 minutes. UVB-treated rats received either CGRP 8-37+saxitoxin patches or control patches (n=6 each group). Sham control group rats (n=6) were completely depilated and cleansed with ethanol wipes but without any other treatment. The rats were returned to their home cages, and assessed for thermal pain responses 48 hours later. As usual, cheek withdrawal latencies in response to continuous and noxious heat were recorded over a 3-hour time period (hours 49-51 post-UVB).

TABLE 6

| UVB Model | | | | | | |
|---|---|---|---|---|---|---|
| | Combination Therapeutics Reduced Latency Post 48 Hrs. | | | | | |
| | Sham | | UVB + Control | | UVB + CGRP8-37 + Saxitoxin | |
| Post patch removal (min) | Mean (sec) | SEM (±sec) | Mean (sec) | SEM (±sec) | Mean (sec) | SEM (±sec) |
| 30 | 12.6 | 0.6 | 6.8 | 0.4 | 10.7 | 1.7 |
| 60 | 12.2 | 0.4 | 6.7 | 0.4 | 11.5 | 1.8 |
| 90 | 12.8 | 1.0 | 7.0 | 0.4 | 12.0 | 1.8 |
| 120 | 13.2 | 0.8 | 6.6 | 0.4 | 12.0 | 2.0 |
| 150 | 13.0 | 0.7 | 7.0 | 0.4 | 11.8 | 2.2 |
| 180 | 13.1 | 0.7 | 6.7 | 0.3 | 12.2 | 2.2 |

In still another therapeutic method embodiment as described above, an intradermal injection is made using a microneedle patch incorporating a combination of CGRP 8-37 or an active AFA-peptide with a steroid, such as dexamethasone or an NSAID, such as ibuprofen, that may be in admixture with one another in a therapeutic composition or may each be located separately and independently within distinct portions of the microneedle therapeutic dosing patch, and a preferred patient is a human patient. One preferred method for such treatment is wherein the pain being treated is neurogenic inflammatory pain selected from one or more of the group consisting of migraine pain, tension headache pain, burn pain, radiation pain, diabetic neuropathic pain or cancer pain.

Table 7 reports data showing local application of steroidal anti-inflammatory drugs, e.g. dexamethasone in combination with CGRP 8-37 (7.8 µg/patch) and dexamethasone (DEX, e.g., 65 µg/patch) as microneedle patches (44 needles/patch, 1.5 mm needle length) or control patches (n=6 each group). The combination therapeutic patch produced potent anti-inflammatory and thermal analgesic effects in rat cheeks with UVB-induced inflammation (24 h post-UVB stimulation, n=6) compared with control patches. The application protocol described above for other applications of drugs using the microneedle patches according to the invention was followed but patches containing the dosing amount of CGRP 8-37 with dexamethasone (65 µg/patch) on rat cheeks for 20 minutes. After removing the patches, cheek withdrawal latencies induced by continuous and noxious heat were assessed at different time points up to 3 hours.

TABLE 7

UVB Model

Steroid Combination on Cheek Withdrawal Latency

| Post patch removal (min) | UVB + Control | | UVB + CGRP8-37/DEX | |
|---|---|---|---|---|
| | Mean (sec) | SEM (±sec) | Mean (sec) | SEM (±sec) |
| 0 | 6.3 | 0.5 | 8.9 | 1.2 |
| 10 | 5.4 | 0.2 | 9.7 | 1.2 |
| 20 | 5.7 | 1.1 | 9.7 | 1.1 |
| 30 | 4.9 | 0.5 | 8.9 | 1.3 |
| 60 | 4.3 | 0.3 | 7.3 | 0.7 |
| 90 | 4.9 | 0.4 | 7.2 | 0.6 |
| 120 | 4.5 | 0.4 | 7.4 | 1.1 |
| 150 | 5.0 | 0.4 | 7.8 | 1.2 |
| 180 | 5.2 | 0.4 | 7.7 | 0.8 |

Table 8 reports data showing local application of non-steroidal anti-inflammatory drugs, e.g. ibuprofen in combination with a lower dose of CGRP 8-37 (7.8 µg/patch) and ibuprofen (e.g., 260 µg/patch) in microneedle patches (44 needles/patch, 1.5 mm needle length) or control patches (n=6 each group). The combination therapeutic patch produces potent anti-inflammatory and thermal analgesic effects in rat cheeks with UVB-induced inflammation (24 h post-UVB stimulation, n=6) compared with control patches. The therapeutic protocol for the application of compositions described above for other applications of drugs using the microneedle patches according to the invention was followed but patches containing the dosing amount of CGRP 8-37 therapeutic with the non-steroidal anti-inflammatory drugs ibuprofen (260 µg/patch) on rat cheeks for 20 minutes. After removing the patches, cheek withdrawal latencies induced by continuous and noxious heat were assessed at different time points from 20 minutes post administration up to 3 hours.

TABLE 8

UVB Model

NSAID Combination on Cheek Withdrawal Latency

| Post patch removal (min) | UVB + Control | | UVB + CGRP/Ibuprofen | |
|---|---|---|---|---|
| | Mean (sec) | SEM (±sec) | Mean (sec) | SEM (±sec) |
| 0 | 4.4 | 0.3 | 8.9 | 0.8 |
| 10 | 5.4 | 0.4 | 9.1 | 1.4 |
| 20 | 5.8 | 0.5 | 10.8 | 1.5 |
| 30 | 5.7 | 0.5 | 10.1 | 0.9 |
| 60 | 6.9 | 0.6 | 9.0 | 0.6 |
| 90 | 6.4 | 0.9 | 9.3 | 1.9 |
| 120 | 6.1 | 0.9 | 9.4 | 1.1 |
| 150 | 6.9 | 1.2 | 8.6 | 2.8 |
| 180 | 7.6 | 1.4 | 9.6 | 3.0 |

Ideal therapeutics of anti-inflammatory pain or anti-hypersensitivity (occurred in neuropathic pain) should not interfere with normal physiological pain sensations. As shown in Table 9, normal rats (without any ongoing inflammation or other physiological pain sensitivity conditions) were tested. Microneedle patches containing CGRP 8-37 (44 needles/patch, 11.3 µg/patch, 1.5 mm needle length for 20 minutes) were applied to rat cheeks (n=6) as described above. After removing the patches, cheek withdrawal latencies (mean±SEM) were assessed using continuous and noxious heat at different time points within the initial 3 hours test period. CGRP 8-37 did not produce any measurable analgesic effect. These test results indicate that CGRP 8-37 does not alter physiological pain sensation. In contract microneedle patch containing 5% lidocaine produced analgesic effect on normal nociceptive pain as expected (data not shown).

TABLE 9

Normal Rats Average Pain Response Latency

| Post patch removal (min) | Control | | CGRP 8-37 | |
|---|---|---|---|---|
| | Mean (sec) | SEM (±sec) | Mean (sec) | SEM (±sec) |
| 0 | 8.9 | 0.4 | 9.6 | 0.4 |
| 10 | 9.1 | 0.2 | 10.1 | 0.4 |
| 20 | 9.1 | 0.2 | 10.2 | 0.4 |
| 30 | 8.8 | 0.5 | 10.3 | 0.6 |
| 60 | 9.7 | 0.6 | 11.0 | 0.6 |
| 90 | 10.2 | 0.4 | 11.2 | 0.4 |
| 120 | 10.2 | 0.2 | 11.0 | 0.4 |
| 150 | 10.0 | 0.4 | 10.6 | 0.4 |
| 180 | 10.0 | 0.5 | 10.5 | 0.4 |

Figure 11A:
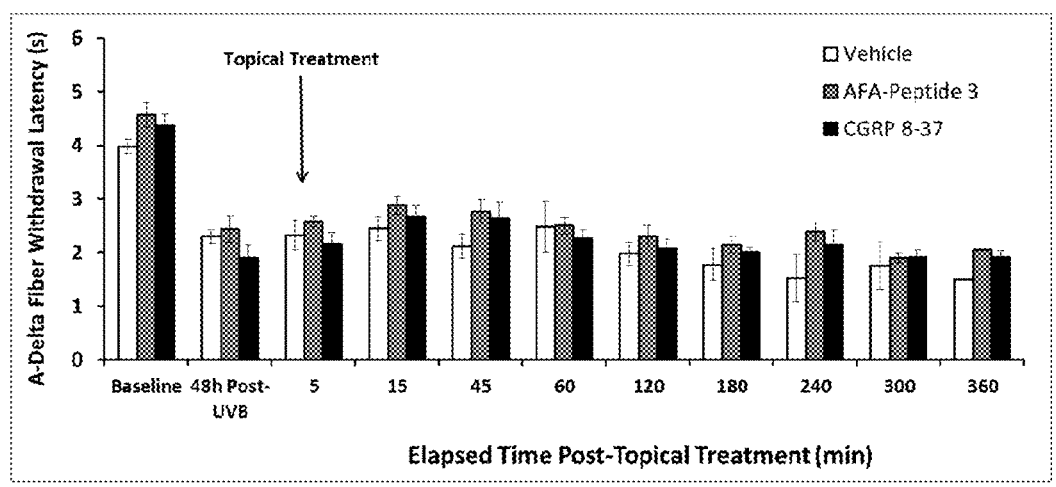
FIG. 11A and FIG. 11B. Topical application of AFA-peptide-3 or CGRP 8-37 on an Ultraviolet B (UVB) radiation-induced inflammatory pain in rats.
Figure 11B:
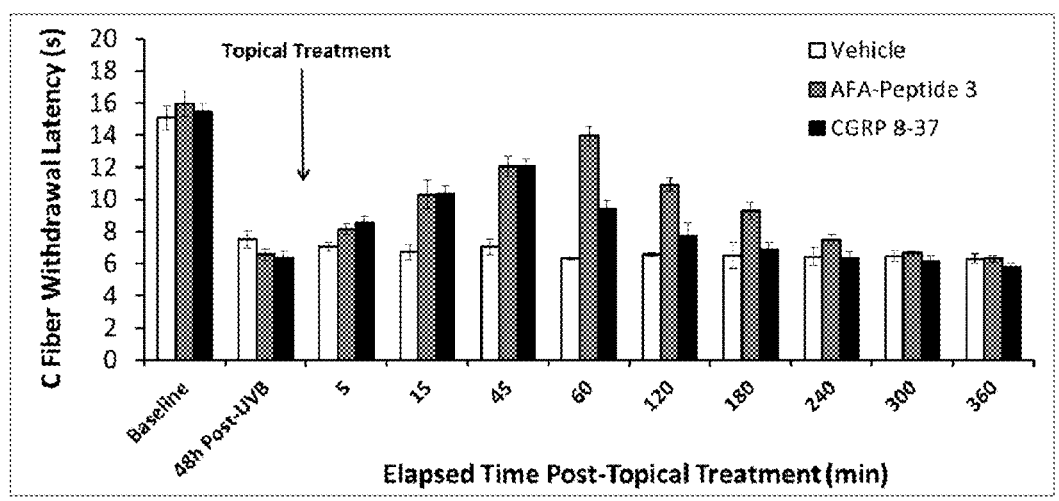

Anti-CGRP Peptide Delivered by Topical Application Mitigates Radiation-Induced Inflammatory Pain Because UVB-irradiation may increase skin permeability, a topical formulation, but not limited to the sample shown here, was made. The AFA-peptide-3 or CGRP 8-37 were dissolved in pure propylene glycol and then diluted with 0.9% NaCl to a final concentration at 10 µM for each peptide containing 2% propylene glycol. The topical application of AFA-peptide-3 or CGRP 8-37 (each 100 µL application) on the UVB-irradiated left rat cheek, caused little effects on A-delta-fiber-mediated responses (FIG. 11A), but produced a significant and substantial increase in C-fiber-mediated thermal pain thresholds compared to vehicle-treated rats under the same UVB conditions (FIG. 11B). The onset of analgesic effect was observed as early as 5 min post-topical application (the first timepoint assessed) and its duration of action lasted for 2 hours.

Example 8. Electrocutaneous Stimulation-Induced Facial Inflammatory Pain Model

Figure 12A:
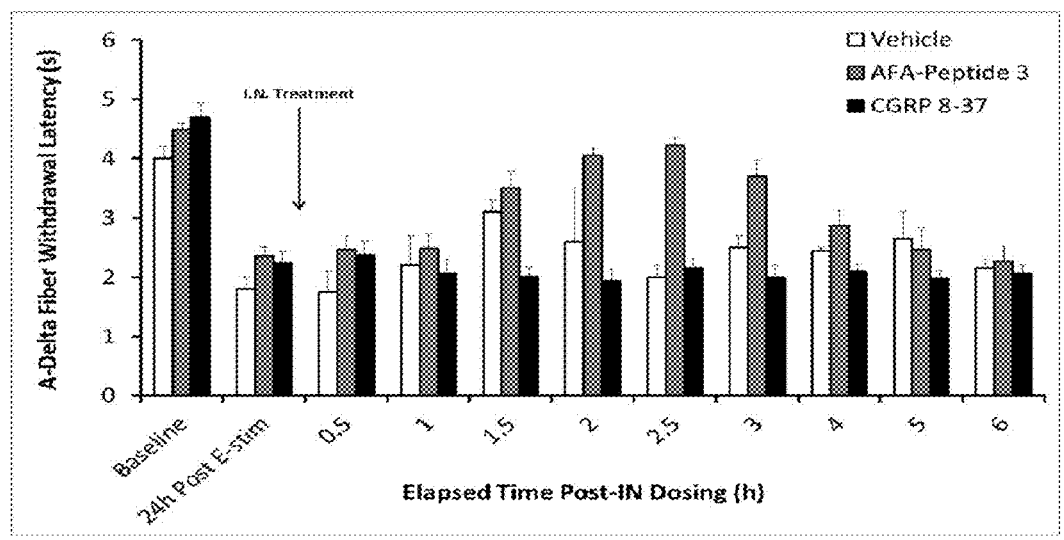
FIG. 12A and FIG. 12B. Intranasal (I.N.) administration of AFA-peptide 3 prolongs paw withdrawal latencies induced by A-delta and C fiber-mediated pain in an electric stimulation-induced facial pain model in rats.
Figure 12B:
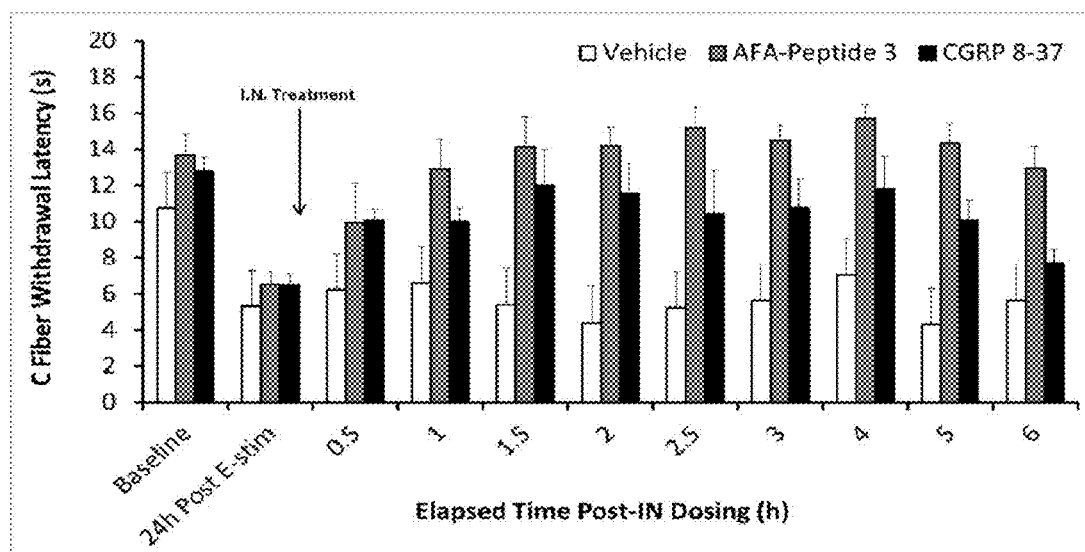

Anti-CGRP Peptide Delivered by Intranasal Administration Mitigates Electrocutaneous Stimulation-Induced Facial Inflammatory Pain In humans electrocutaneous stimulation elicited vasodilatation in the cheek (Vassend and Knardahl, 2005). Repeated electrocutaneous pain stimulation of the animal cheek could be used as an experimental model of facial inflammatory pain and is plausibly involved in CGRP receptor activation. Baseline facial thermal thresholds of rats (Sprague-Dawley, male, 260-300 g) were assessed on the rats' depilated left cheek and then each rat received 1 hour of electrocutaneous facial stimulation using WPI ISOSTIM™ A320 (World Precision Instruments, 0.4 mA intensity, 10 ms duration, Is inter-pulse interval). 24 hr after stimulation (Day 1), each rat's thermal pain threshold mediated by A-delta fiber and C fiber were separately measured using a thermal nociception lamp (variable voltage regulator model: No. SC-3M) to evoke A-delta and C nerve fiber-mediated cheek withdrawal. As FIG. 12A and FIG. 12B show those rats post electrocutaneous stimulation (Post E-stim) exhibited facial hyperalgesia. Each rat was then treated with either AFA-Peptide 3 (1 μM), CGRP 8-37 (1 μM) or vehicle (0.9% NaCl), via local intranasal (I.N.) administration (n=6 rats/group). Thermal thresholds were measured once every 0.5 hour for the first 3 hours post-I.N. dosing, and then 4, 5, and 6 hour post-I.N. dosing. Voltage regulator set to 90V for A-delta fiber testing and 45V for C fiber testing. Cutoff set at 6 seconds and 20 seconds for A-delta fiber and C fiber testing, respectively. As FIG. 12A shows, local intranasally administered AFA-peptide 3 significantly prolonged A-delta fiber-mediated pain induced paw withdrawal latencies compared to vehicle. C-fiber-mediated pain induced paw withdrawal latencies were even more substantial and significantly prolonged by I.N. admonition of AFA-peptide 3 or CGRP 8-37 compared to vehicle (FIG. 12B). In contrast, both CGRP 8-37 and AFA-peptide 3 (I.N.) did not alter thermal pain thresholds in naïve, non-facial stimulation rats (data not shown).

Example 9. Paw Incision-Induced Postoperative Pain Model

Anti-CGRP Peptide Delivered by Local Injection Mitigates Postoperative Pain

In another embodiment, the invention provides a pharmaceutical composition comprising a therapeutically effective amount of an active AFA-peptide or CGRP 8-37 in carrier vehicle suitable for intradermal administration by injection at the peripheral site in a patient experiencing postoperative pain with a neurogenic inflammatory condition that is in need of therapeutic treatment.

A clinically applicable incision model in rodents is a hind-paw deep incision that produces a robust mechanical and cold allodynia, and thermal hyperalgesia (Pogatzki et al., 2003; Xu and Brennan, 2010). Male rats (Sprague-Dawley, 250-260 g, Harlan) used (n=8/group) were anesthetized with 2.5% isoflurane and the skin of the dorsolateral hindpaw surface were prepped by first depilitating it (using Nair), followed by rinsing and application of povidone-iodine. Afterwards, a 5 mm longitudinal incision was made near the hairy/glabrous border though the skin and subcutaneous fascia of the left hindpaw as described by (Pogatzki et al., 2003; Xu and Brennan, 2010). After briefly elevating the underlying muscle with curved forceps the wound is closed with a single nylon (8-0) mattress stitch.

Figure 13:
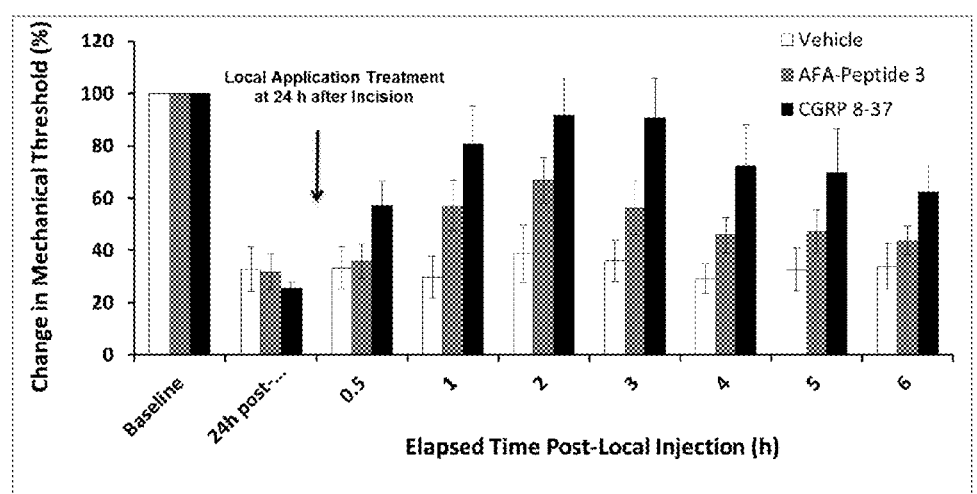
FIG. 13. Local injection of AFA-peptide-3 or CGRP8-37 in vehicle solutions (0.5% hydroxyl propyl cellulose containing 2% DMSO) treats and prevents neurogenic inflammatory pain following incision in rat paws. A bar graph of mechanical pain threshold assessment data showing local injection of AFA-peptide-3 or CGRP8-37 solutions 24 hours after the incision in rat paws reduce the allodynia as indicated by an increase in mechanical pain threshold.

Pre-surgery (baseline) and 24 hours after the surgery, the mechanical allodynia of the incision hindpaws of the rats were assessed using von Frey monofilaments with an up/down procedure (Chaplan et al., 1994). After the presence of mechanical allodynia in each postoperative rat was confirmed, local intradermal injection of a solution containing AFA-peptide-3 or CGRP 8-37 (each at 1 μM, 50 μL) or vehicle (0.5% hydroxyl propyl cellulose containing 2% DMSO). Mechanical pain thresholds were measured at 0.5, 1, 2, 3, 4, 5 and 6 hours post-intradermal injection. Compared to vehicle the analgesic effect of AFA-peptide-3 or CGRP 8-37 was observed in the first timepoint 0.5 hour post-treatment assessed and its duration of action lasted for around 6 hours. The mechanical pain threshold also significantly increased with the treatment of AFA-peptide-3 (FIG. 13).

Figure 14:
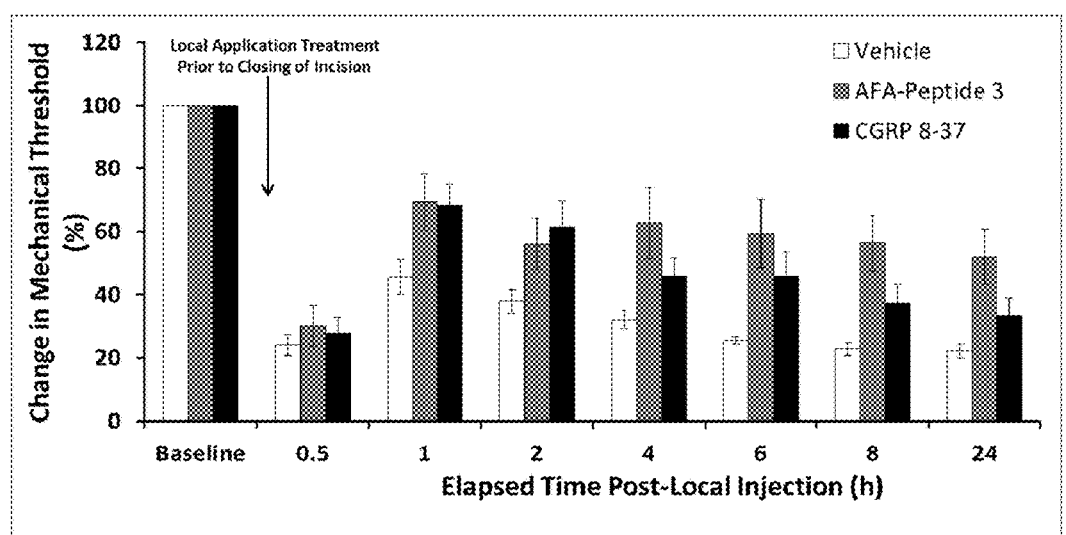
FIG. 14. Local injection of AFA-peptide-3 or CGRP8-37 prevents neurogenic inflammatory pain following incision in rat paws. A bar graph of mechanical pain threshold assessment data showing local injection of AFA-peptide-3 or CGRP8-37 solutions immediately prior to closing of an incision in rat paws. Local peripheral application of the CGRP antagonists prevents the development of hyperalgesia and allodynia induced by incision.

In a prevention of neurogenic inflammation test, the injection of AFA-peptide-3 or CGRP 8-37 (each 1 μM, 50 μL) was made just prior to the closing of the wound (incision cut). Both peptides produced longer analgesic effects compared to treatment method described above. As shown in FIG. 14, AFA-peptide-3 and CGRP 8-37 significantly increased mechanical pain thresholds compared to vehicle in the incision pain model. The onset of analgesic effect was observed in 1 hour post treatment, the second timepoint assessed and its duration of action lasted even for 24 hours for AFA-Peptide 3, and 8 hours for CGRP 8-37.

Although the foregoing invention has been described in some detail by way of illustration and example for purposes of clarity of understanding, one of skill in the art will appreciate that certain changes and modifications may be practiced within the scope of the appended claims.

All publications, accession numbers, and patent applications cited in this specification are herein incorporated by reference as if each individual publication or patent application were specifically and individually indicated to be incorporated by reference.

PATENT CITATIONS

| Cited patent | Filling date | Publication date | Applicant | Title |
| --- | --- | --- | --- | --- |
| U.S. Pat. No. 4,549,986 | Dec. 23, 1983 | Oct. 29, 1985 | The Salk Institute for Biological Studies | Human CGRP |
| U.S. Pat. No. 6,268,474 | Apr. 30, 1998 | Jul. 31, 2001 | Creighton University | Peptide antagonists of CGRP-receptor superfamily and methods of use |

-continued

| Cited patent | Filling date | Publication date | Applicant | Title |
| --- | --- | --- | --- | --- |
| WO 2007048026 A2 | Oct. 20, 2006 | Apr. 20, 2007 | Amgen, Inc. | CGRP peptide antagonists and conjugates |
| WO 2009/109911 | Mar. 3, 2009 | Sep. 11, 2009 | Pfizer Limited | Methods of treating chronic pain |
| US 20110054150 A1 | Mar. 4, 2008 | Mar. 3, 2011 | Pfizer Limited | Methods of treating inflammatory pain |
| US6908453 B2 | Jan. 15, 2002 | Jun. 21, 2005 | 3M Innovative Properties Company | Microneedle devices and methods of manufacture |
| US 20040199103 A1 | Jan. 28, 2004 | Oct. 7, 2004 | TheraJect, Inc. | Solid solution perforator for drug delivery and other applications |

OTHER REFERENCES

Akimoto T, Masuda A, Yotsu-Yamashita M, Hirokawa T, Nagasawa K (2013) Synthesis of saxitoxin derivatives bearing guanidine and urea groups at C13 and evaluation of their inhibitory activity on voltage-gated sodium channels. Org Biomol Chem 11:6642-6649.

Amara S G, Jonas V, Rosenfeld M G, Ong E S, Evans R M (1982) Alternative RNA processing in calcitonin gene expression generates mRNAs encoding different polypeptide products. Nature 298:240-244.

Benemei S, Nicoletti P, Capone J G, Geppetti P (2009) CGRP receptors in the control of pain and inflammation. Curr Opin Pharmacol 9:9-14.

Bishnoi M, Bosgraaf C A, Abooj M, Zhong L, Premkumar L S (2011) Streptozotocin-induced early thermal hyperalgesia is independent of glycemic state of rats: role of transient receptor potential vanilloid 1 (TRPV1) and inflammatory mediators. Mol Pain 7:52.

Boulanger Y, Khiat A, Chen Y, Senecal L, Tu Y, St-Pierre S, Foumier A (1995) Structure of human calcitonin gene-related peptide (CGRP) and of its antagonist CGRP 8-37 as determined by NMR and molecular modeling. Pept Res 8:206-213.

Chaplan S R, Bach F W, Pogrel J W, Chung J M, Yaksh T L (1994) Quantitative assessment of tactile allodynia in the rat paw. J Neurosci Methods 53:55-63.

Chiba T, Yamaguchi A, Yamatani T, Nakamura A, Morishita T, Inui T, Fukase M, Noda T, Fujita T (1989) Calcitonin gene-related peptide receptor antagonist human CGRP-(8-37). Am J Physiol 256:E331-335.

Cheng, Y-C, Prusoff, W H (1973) Relationship between the inhibition constant (Ki) and the concentration of inhibitor which causes 50 percent inhibition (I50) of an enzymatic reaction. Biochem. Pharmacol. 22: 3099-3108.

Chong R H, Gonzalez-Gonzalez E, Lara M F, Speaker T J, Contag C H, Kaspar R L, Coulman S A, Hargest R, Birchall J C (2013) Gene silencing following siRNA delivery to skin via coated steel microneedles: In vitro and in vivo proof-of-concept. J Control Release 166:211-219.

Decosterd I, Woolf C J (2000) SNI: an animal model of persistent peripheral neuropathic pain. Pain 87:149-158.

Dorsi M J, Chen L, Murinson B B, Pogatzki-Zahn E M, Meyer R A, Belzberg A J (2008) The tibial neuroma transposition (TNT) model of neuroma pain and hyperalgesia. Pain 134(3): 320-334.

Edvinsson L, Warfvinge K (2013) CGRP receptor antagonism and migraine therapy. Curr Protein Pept Sci 14:386-392.

Farinelli I, De Filippis S, Coloprisco G, Missori S, Martelletti P (2009) Future drugs for migraine. Intern Emerg Med 4:367-373.

Hargreaves K, Dubner R, Brown F, Flores C, Joris J (1988) A new and sensitive method for measuring thermal nociception in cutaneous hyperalgesia. Pain 32:77-88.

Herbert M K, Holzer P (2002) [Neurogenic inflammation. I. Basic mechanisms, physiology and pharmacology]. Anasthesiol Intensivmed Notfallmed Schmerzther 37:314-325.

Hostetler E D et al. (2013) In vivo quantification of calcitonin gene-related peptide receptor occupancy by telcagepant in rhesus monkey and human brain using the positron emission tomography tracer [11C]MK-4232. J Pharmacol Exp Ther 347:478-486.

Jurynczyk M, Walczak A, Jurewicz A, Jesionek-Kupnicka D, Szczepanik M, Selmaj K (2010) Immune regulation of multiple sclerosis by transdermally applied myelin peptides. Ann Neurol 68:593-601.

Martelli P, Saleri R, Cavalli V, De Angelis E, Ferrari L, Benetti M, Ferrarini G, Merialdi G, Borghetti P (2014) Systemic and local immune response in pigs intradermally and intramuscularly injected with inactivated Mycoplasma hyopneumoniae vaccines. Vet Microbiol 168:357-364.

Malon J T, Maddula S, Bell H, Cao L (2012). Involvement of calcitonin gene-related peptide and CCL2 production in CD40-mediated behavioral hypersensitivity in a model of neuropathic pain. Neuron Glia Biol. 7(2-4):117-28.

Nassini R, Materazzi S, Benemei S, Geppetti P (2014) The TRPA1 Channel in Inflammatory and Neuropathic Pain and Migraine. Rev Physiol Biochem Pharmacol.

Nieber K (2009) [CGRP antagonists: novel concept for treatment of migraine]. Med Monatsschr Pharm 32:182-185.

Plourde V, St-Pierre S, Quirion R (1997) Calcitonin gene-related peptide in viscerosensitive response to colorectal distension in rats. Am J Physiol 273:G191-196.

Pogatzki E M, Niemeier J S, Sorkin L S, Brennan T J (2003) Spinal glutamate receptor antagonists differentiate primary and secondary mechanical hyperalgesia caused by incision. Pain 105:97-107.

Rist B, Lacroix J S, Entzeroth M, Doods H N, Beck-Sickinger A G (1999) CGRP 27-37 analogues with high affinity to the CGRP1 receptor show antagonistic properties in a rat blood flow assay. Regul Pept 79:153-158.

Shinohara R, Akimoto T, Iwamoto O, Hirokawa T, Yotsu-Yamashita M, Yamaoka K, Nagasawa K (2011) Synthesis of skeletal analogues of saxitoxin derivatives and evaluation of their inhibitory activity on sodium ion channels Na(V)1.4 and Na(V)1.5. Chemistry 17:12144-12152.

Trevisan G, Hoffmeister C, Rossato M F, Oliveira S M, Silva M A, Silva C R, Fusi C, Tonello R, Minocci D, Guerra G P, Materazzi S, Nassini R, Geppetti P, Ferreira J (2014) TRPA1 receptor stimulation by hydrogen peroxide is critical to trigger hyperalgesia and inflammation in a model of acute gout. Free Radic Biol Med 72:200-209.

Troconiz I F, Wolters J M, Tillmann C, Schaefer H G, Roth W (2006) Modelling the anti-migraine effects of BIBN 4096 BS: a new calcitonin gene-related peptide receptor antagonist. Clin Pharmacokinet 45:715-728.

Tzabazis A Z, Pirc G, Votta-Velis E, Wilson S P, Laurito C E, Yeomans D C (2007) Antihyperalgesic effect of a recombinant herpes virus encoding antisense for calcitonin gene-related peptide. Anesthesiology 106:1196-1203.

Uhl R L, Roberts T T, Papaliodis D N, Mulligan M T, Dubin A H (2014) Management of chronic musculoskeletal pain. J Am Acad Orthop Surg 22:101-110.

Vassend O, Knardahl S (2005) Effects of repeated electrocutaneous pain stimulation on facial blood flow. Biol Psychol 68:163-178.

Xu J, Brennan T J (2010) Guarding pain and spontaneous activity of nociceptors after skin versus skin plus deep tissue incision. Anesthesiology 112:153-164.

Yeomans, D C Pirec, V, and Proudfit, H K (1996) Nociceptive responses to high or low rates of noxious cutaneous heating are mediated by different nociceptors in the rat: behavioral evidence. Pain, 68: 133-140.

Zhang Q, Sitzman L A, Al-Hassani M, Cai S, Pollok K E, Travers J B, Hingtgen C M (2009) Involvement of platelet-activating factor in ultraviolet B-induced hyperalgesia. J Invest Dermatol 129:167-174.

Zochodne D W, Allison J A, Ho W, Ho L T, Hargreaves K, Sharkey K A (1995) Evidence for CGRP accumulation and activity in experimental neuromas. Am J Physiol. 268(2):H584-90

What is claimed is:

1. A method of treating neurogenic inflammatory pain that is not migraine pain in a subject in need of such treatment with the proviso that treating said neurogenic inflammatory pain does not include prophylaxis of the specific disorder or condition, said method comprising administering to said subject a therapeutically effective amount of the isolated or synthesized polypeptide selected from the group consisting of:

```
(MP-3; SEQ. ID. NO.: 35):
NH2-N-F-V-P-T-N-V-G-P-F-A-F-CONH2;

(MP-5; SEQ. ID. NO.: 37):
NH2-D-N-F-V-P-T-N-V-G-P-F-A-F-CONH2;

(MP-6; SEQ. ID. NO.: 38):
NH2-N-F-I-P-T-N-V-G-P-F-A-F-CONH2;

(MP-7; SEQ. ID. NO.: 39):
NH2-N-F-L-P-T-N-V-G-P-F-A-F-CONH2;
and (MP-10; SEQ. ID. NO.: 42):
NH2-N-F-A-P-T-N-V-G-P-F-A-F-CONH2.
```

2. The method of claim 1, wherein said administering comprises injecting said isolated or synthesized polypeptide in to the dermis of said subject.

3. The method of claim 1, wherein said administering is via a patch comprising at least one microneedle, said patch temporarily fixed to the outer surface of the skin of said subject.

4. The method of claim 1, wherein said administering is at a site including or adjacent to a locus of said pain.

5. The method of claim 1, wherein said administering is using conventional metal needle injection or microneedle delivery subcutaneously, transdermally; or topical application in the pain area or at adjacent to an acupuncture point or a trigger point; or intranasal administration.

6. The method of claim 1, wherein said neurogenic inflammatory pain that is not migraine pain is selected from the group consisting of dental pain, root canal pain, trigeminal inflammatory pain, temporomandibular joint (TMJ) disorder, burn pain, radiation pain, erythromelalgia, complex regional pain syndrome, and cancer pain.

7. A method of reducing neurogenic inflammatory pain that is not migraine pain in a subject experiencing said neurogenic inflammatory pain, said method comprising administering to said subject an amount of the isolated or synthesized polypeptide sufficient to reduce said neurogenic inflammatory pain, wherein the polypeptide is selected from the group consisting of:

```
(MP-3; SEQ. ID. NO.: 35):
NH2-N-F-V-P-T-N-V-G-P-F-A-F-CONH2;

(MP-5; SEQ. ID. NO.: 37):
NH2-D-N-F-V-P-T-N-V-G-P-F-A-F-CONH2;

(MP-6; SEQ. ID. NO.: 38):
NH2-N-F-I-P-T-N-V-G-P-F-A-F-CONH2;

(MP-7; SEQ. ID. NO.: 39):
NH2-N-F-L-P-T-N-V-G-P-F-A-F-CONH2;
and (MP-10; SEQ. ID. NO.: 42):
NH2-N-F-A-P-T-N-V-G-P-F-A-F-CONH2.
```

8. A method of reducing neurogenic inflammatory pain that is not migraine pain in a subject experiencing said neurogenic inflammatory pain, said method comprising administering to said subject an amount of the isolated polypeptide having a sequence consisting of SEQ ID NO:35 (NH2-N-F-V-P-T-N-V-G-P-F-A-F-CONH2) sufficient to reduce said neurogenic inflammatory pain.

* * * * *